United States Patent
Greaves

(10) Patent No.: US 9,730,876 B2
(45) Date of Patent: Aug. 15, 2017

(54) PROCESS FOR DYEING KERATIN FIBRES COMPRISING A DYE-PIGMENT, A PHOTOACTIVE COMPOUND AND A LIGHT SOURCE

(71) Applicant: L'OREAL, Paris (FR)

(72) Inventor: Andrew Greaves, Magny-le-hongre (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/403,022

(22) PCT Filed: May 22, 2013

(86) PCT No.: PCT/EP2013/060522
§ 371 (c)(1),
(2) Date: Nov. 21, 2014

(87) PCT Pub. No.: WO2013/174871
PCT Pub. Date: Nov. 28, 2013

(65) Prior Publication Data
US 2015/0224041 A1   Aug. 13, 2015

Related U.S. Application Data

(60) Provisional application No. 61/660,009, filed on Jun. 15, 2012.

(30) Foreign Application Priority Data

May 23, 2012   (FR) ..................................... 12 54703

(51) Int. Cl.
*A61Q 5/10* (2006.01)
*A61K 8/49* (2006.01)
*A61Q 5/06* (2006.01)

(52) U.S. Cl.
CPC ............ *A61K 8/4926* (2013.01); *A61Q 5/065* (2013.01); *A61Q 5/10* (2013.01); *A61K 2800/43* (2013.01); *A61K 2800/81* (2013.01); *A61K 2800/95* (2013.01)

(58) Field of Classification Search
CPC ...... A61Q 5/10; A61Q 5/065; A61K 2800/43; A61K 2800/81; A61K 2800/95
USPC ..................................... 8/405; 132/202, 208
See application file for complete search history.

(56) References Cited

U.S. PATENT DOCUMENTS

| | | | |
|---|---|---|---|
| 5,645,609 A | 7/1997 | Andrean et al. | |
| 5,708,151 A | 1/1998 | Mockli | |
| 5,944,360 A | 8/1999 | Crapart | |
| 7,641,703 B2 | 1/2010 | Guerin et al. | |
| 7,717,964 B2 | 5/2010 | Daubresse et al. | |
| 7,744,657 B2 | 6/2010 | Greaves et al. | |
| 7,744,658 B2 | 6/2010 | Greaves et al. | |
| 7,780,743 B2 | 8/2010 | Greaves et al. | |
| 8,038,731 B2 | 10/2011 | Daubresse et al. | |
| 8,328,880 B2 | 12/2012 | Daubresse et al. | |
| 2006/0080791 A1 | 4/2006 | Daubresse et al. | |
| 2008/0244838 A1 | 10/2008 | Guerin et al. | |
| 2009/0089939 A1 | 4/2009 | Greaves et al. | |
| 2009/0126125 A1 | 5/2009 | Greaves et al. | |
| 2009/0172897 A1 | 7/2009 | Daubresse et al. | |
| 2009/0313769 A1* | 12/2009 | Daubresse | A61K 8/49 8/406 |
| 2009/0320216 A1 | 12/2009 | Greaves et al. | |
| 2010/0287714 A1 | 11/2010 | Greaves et al. | |
| 2011/0011417 A1 | 1/2011 | Greaves et al. | |
| 2011/0017227 A1 | 1/2011 | Samain | |

FOREIGN PATENT DOCUMENTS

| | | | | |
|---|---|---|---|---|
| DE | 4119591 | A1 | 12/1992 | |
| DE | 4319035 | A1 | 12/1994 | |
| DE | 4427888 | A1 | 2/1996 | |
| DE | 102005052139 | A1 | 5/2007 | |
| DE | 102007018380 | A1 | 10/2008 | |
| DE | 102009001687 | A1 | 1/2010 | |
| DE | 102009002317 | A1 | 2/2010 | |
| DE | 102009002317 | A1 * | 11/2010 | ............... A61K 8/81 |
| EP | 0714954 | A2 | 6/1996 | |
| EP | 0860636 | A1 | 8/1998 | |
| EP | 1133975 | A2 | 9/2001 | |

(Continued)

OTHER PUBLICATIONS

English translation (Oct. 7, 2015) of the Patent No. DE 102009002317 A1.*
STIC Search Report dated Sep. 20, 2016.*
International Search Report for PCT/EP2013/060522.
English abstract of DE 4119591A1 (Dec. 17, 1992).
English abstract of DE 4427888A1 (Feb. 15, 1996).
English abstract of DE 102005052139A1 (May 3, 2007).
English abstract of DE 102007018380A1 (Oct. 30, 2008).
English abstract of DE 102009001687A1 (Jan. 14, 2010).
English abstract of DE 102009002317A1 (Feb. 11, 2010).
English abstract of EP 1537853A1 (Jun. 8, 2005).
English abstract of EP 1944010A2 (Jul. 16, 2008).

(Continued)

*Primary Examiner* — Eisa Elhilo
(74) *Attorney, Agent, or Firm* — The Marbury Law Group, PLLC.

(57) ABSTRACT

The invention relates to a process for dyeing and/or lightening keratin fibers using i) particular dye(s) and/or pigment(s), ii) photoactive compound(s) and iii) light source(s); a cosmetic composition comprising the ingredients i) and ii); the use of ii) for improving the fastness and/or dyeing and/or lightening of keratin materials in the presence of the ingredients i) and iii) of light source(s), and a multi-compartment device comprising i), ii) and iii). The implementation process and the use i) of particular dye(s) and/or pigment(s) combined with ii) the photoactive compounds and iii) with a light source make it possible especially to obtain lasting coloration on keratin fibers without the use of a reducing agent, and without odor.

13 Claims, No Drawings

(56) References Cited

FOREIGN PATENT DOCUMENTS

| | | |
|---|---|---|
| EP | 1166754 A2 | 1/2002 |
| EP | 1184426 A2 | 3/2002 |
| EP | 1537853 A1 | 6/2005 |
| EP | 1647580 A1 | 4/2006 |
| EP | 1944010 A2 | 7/2008 |
| EP | 1972327 A1 | 9/2008 |
| EP | 2004759 A2 | 12/2008 |
| EP | 2039724 A1 | 3/2009 |
| EP | 2070988 A2 | 6/2009 |
| EP | 2075288 A1 | 7/2009 |
| EP | 2075289 A1 | 7/2009 |
| FR | 2679771 A1 | 2/1993 |
| FR | 2920779 A1 | 3/2009 |
| FR | 2920780 A1 | 3/2009 |
| FR | 2920781 A1 | 3/2009 |
| FR | 2921375 A1 | 3/2009 |
| FR | 2921380 A1 | 3/2009 |
| FR | 2924597 A1 | 6/2009 |
| FR | 2953397 A1 | 6/2011 |
| FR | 2954118 A1 | 6/2011 |
| FR | 2967683 A1 | 5/2012 |
| JP | 56-161466 A | 12/1981 |
| JP | 61-036363 A | 2/1986 |
| JP | 2002-060642 A | 2/2002 |
| JP | 2002-060643 A | 2/2002 |
| JP | 2002-060645 A | 2/2002 |
| JP | 2002-148801 A | 5/2002 |
| WO | 94/29387 A1 | 12/1994 |
| WO | 95/01772 A1 | 1/1995 |
| WO | 95/15144 A1 | 6/1995 |
| WO | 03/029359 A1 | 4/2003 |
| WO | 2007/110531 A2 | 10/2007 |
| WO | 2007/110532 A2 | 10/2007 |
| WO | 2007/110533 A2 | 10/2007 |
| WO | 2007/110534 A2 | 10/2007 |
| WO | 2007/110535 A2 | 10/2007 |
| WO | 2007/110536 A2 | 10/2007 |
| WO | 2007/110537 A2 | 10/2007 |
| WO | 2007/110539 A2 | 10/2007 |
| WO | 2007/110540 A2 | 10/2007 |
| WO | 2007/110541 A2 | 10/2007 |
| WO | 2007/110542 A2 | 10/2007 |
| WO | 2009/034059 A2 | 3/2009 |
| WO | 2009/037324 A2 | 3/2009 |
| WO | 2009/037325 A2 | 3/2009 |
| WO | 2009/037348 A1 | 3/2009 |
| WO | 2009/040354 A1 | 4/2009 |
| WO | 2009/103798 A1 | 8/2009 |
| WO | 2009/124800 A1 | 10/2009 |
| WO | 2010/093210 A2 | 8/2010 |
| WO | 2011/054966 A2 | 5/2011 |
| WO | 2011/067707 A2 | 6/2011 |
| WO | 2011/086283 A1 | 7/2011 |
| WO | 2012/069476 A1 | 5/2012 |

OTHER PUBLICATIONS

English abstract of FR 2920779A1 (Mar. 13, 2009).
English abstract of FR 2920780A1 (Mar. 13, 2009).
English abstract of FR 2920781A1 (Mar. 13, 2009).
English abstract of FR 2921375A1 (Mar. 27, 2009).
English abstract of FR 2921380A1 (Mar. 27, 2009).
English abstract of JP 56-161466A (Dec. 11, 1981).
English abstract of JP 61-036363A (Feb. 21, 1986).
English abstract of JP 2002-060642A (Feb. 26, 2002).
English abstract of JP 2002-060643A (Feb. 26, 2002).
English abstract of JP 2002-060645A (Feb. 26, 2002).
English abstract of JP 2002-148801A (May 22, 2002).
English abstract of WO 94/29387A1 (Dec. 22, 1994).
English abstract of WO 2009/103798A1 (Aug. 27, 2009).
English abstract of WO 2009/124800A1 (Oct. 15, 2009).
English abstract of WO 2010/093210A2 (Aug. 19, 2010).
English abstract of WO 2011/086283A1 (Jul. 21, 2011).

* cited by examiner

PROCESS FOR DYEING KERATIN FIBRES COMPRISING A DYE-PIGMENT, A PHOTOACTIVE COMPOUND AND A LIGHT SOURCE

CROSS REFERENCE TO RELATED APPLICATIONS

This is a national stage application of PCT/EP2013/060522, filed internationally on May 22, 2013, which claims priority to U.S. Provisional Application No. 61/660,009, filed on Jun. 15, 2012, as well as French Application No. 1254703, filed May 23, 2012.

The invention relates to a process for dyeing and/or lightening keratin fibres using i) particular dye(s) and/or pigment(s), ii) photoactive compound(s) and iii) light source(s); a cosmetic composition comprising the ingredients i) and ii); the use of ii) for improving the fastness and/or dyeing and/or lightening of keratin materials in the presence of the ingredients i) and iii) of light source(s), and a multi-compartment device comprising i), ii) and iii).

The implementation process, the use i) of dye(s) and/or pigment(s) combined with the ii) photoactive compound(s) and iii) with one or more light source(s) make it possible especially to obtain lasting coloration on keratin fibres without the necessary use of a reducing agent, and/or of a chemical oxidizing agent, and of doing so without odour. The combination also makes it possible to obtain better dyeing properties in terms of colours, or of lightening.

It is known practice to obtain "permanent" colorations with dye compositions comprising oxidation dye precursors, generally known as oxidation bases, such as ortho- or para-phenylenediamines, ortho- or para-aminophenols and heterocyclic compounds. These oxidation bases are colourless or weakly coloured compounds which, in combination with oxidizing products, can give rise to coloured compounds by an oxidative condensation process. It is also known that the shades obtained can be varied by combining these oxidation bases with couplers or coloration modifiers, the latter being chosen in particular from aromatic meta-diamines, meta-aminophenols, meta-diphenols and certain heterocyclic compounds. This oxidation dyeing process consists in applying to the keratin fibres bases and optionally couplers with hydrogen peroxide as oxidizing agent, in leaving it to diffuse, and then in rinsing the fibres. Commercial hair dyes which comprise them can have drawbacks, such as staining, and problems of odour, comfort and damage to the keratin fibres.

It is also known practice to dye keratin fibres by direct dyeing or semi-permanent dyeing. Direct dyeing or semi-permanent dyeing consists in introducing colour via a coloured molecule that becomes adsorbed onto the surface of the hair or that penetrates into the hair. Thus, the process conventionally used in direct dyeing consists in applying to keratin fibres direct dyes, which are coloured and colouring molecules that have affinity for the fibres, leaving the fibres in contact with the colouring molecules and then optionally rinsing the fibres. Generally, this technique leads to chromatic colorations.

Scientific research has been conducted for several years to modify the colour of keratin materials, especially keratin fibres, and in particular to mask white fibres, to modify the colour of the fibres permanently or temporarily, to obtain colours that are less selective between the root and the end and to satisfy new desires and needs in terms of colours and durability.

In fields other than the dyeing of keratin fibres, use has been made of reactive dyes bearing a branched sulfonoalkenyl group which may especially contain four carbon atoms (DE 41 19 591), azo dyes of pyrazolone, indolidine or thiophene type which may comprise an alkenyl group containing three carbon atoms (JP 61 036 363, JP 2002 148 801 and JP 56 161 466). Dicyanophenylazoimidazole dyes of formula (A) as defined below have also been listed as being used in inks (JP 2002 060 642, JP 2002 060 643, JP 2002 060 645) and the synthesis of cyanine heptamethine benzazoliums of formulae (B) to (K) as defined below (M. J. Nunes et al., *Tetrahedron Lett.*, 48, 5137-5142 (2007)). It is also known practice to dye wool with 1,8-naphthalimide dyes bearing an allylic unit ($CH_2$—CH=$CH_2$) (*Dyes and Pigments* (2000), 45(2), 125-129).

In the field of hair dyeing, it is known practice to use cationic direct dyes bearing an allylic unit. Mention may be made of dyes of the benz[c,d]indolium type (DE 102009001687) type, cationic direct dyes of chromene, acridium or aza (WO 2009124800, WO 2009103798, DE 10 2007 018 380 and EP 1 166 754) and anthraquinone and spiro dyes (DE 43 19 035, EP 1 972 327 and EP 1 537 853). It is also known practice to treat the hair with dyes derived from acrylic acid (EP 1 944 010). These dyes are of the azo type and alkenyl ethylenyl group comprising two carbon atoms.

Moreover, photoactive compounds exist, which are also known as PACs or photoinitiators, which are known for absorbing light and for becoming transformed by generating atoms or molecules comprising chemical reactivity (*Encyclopedia of Polymer Science and Technology*, "photopolymerisation free radical" http:onlinelibrary.wiley.com/doi/10.10020471440264.pst490pdf; C. Decker, *Macromol. Rapid Commun.* 23, 1067-1093 (2002). The latter dyes have been used in compositions containing photosensitive resins, etc., in particular, PACs which generate radicals to enable or initiate the radical polymerization of certain polymers (photopolymerization initiator) (see, for example, WO 2010093210). Photoactive compounds have not, to date, been used in the dyeing of keratin materials, in particular keratin fibres.

The aim of the present invention is to provide novel hair dyeing systems for obtaining odourless or virtually odourless colorations, which are fast with respect to external agents, homogeneous and very strong, and/or which do not impair the cosmetic properties of keratin fibres, and to do so without the use of a reducing agent and/or of a chemical oxidizing agent.

Another aim of the invention is to provide a dyeing system for obtaining visible colorations on naturally or artificially dark keratin fibres, with lightening effects even in the absence of a chemical oxidizing agent, without degradation of the fibre, and/or whose coloration remains remanent with respect to external agents such as shampoos. Another aim of the invention is to obtain long-lasting lightening of dark keratin materials, even in the absence of a chemical oxidizing agent and/or a reducing agent.

These aims are achieved with the present invention, a first subject of which is a process for dyeing keratin materials, especially keratin fibres such as the hair, comprising the following steps:

applying to the fibres at least i) one dye and/or pigment;
applying to the fibres at least ii) one photoinitiator; and
subjecting said keratin fibres to at least iii) one light source (including light emitted by diodes) preferably emitting one or more electromagnetic wave(s) with a wavelength inclusively between 10 nm in the ultraviolet (UV) region and 100 μm in the infrared (IR) region, more particularly between 200 nm and 3 μm;

it being understood that:
the dye(s) or pigment(s) contain at least one photoreactive or photolabile group;
the steps may be performed together or separately, preferably i) and ii) are applied together, followed by iii), more particularly i), ii) and iii) are applied together; and
when i) the dye(s) or pigment(s) contain at least one alkenyl or alkynyl photoreactive group, the presence of ii) photoinitiator is optional, i.e. the step with ii) may be absent from the dyeing process.

A subject of the invention is also novel dyes comprising at least one alkenyl photoreactive group, or at least one alkynyl group of formula (I') below:

$$A_1(X_1)_p—R_{a1} \quad (I')$$

and also the organic or mineral acid or base salts, optical isomers and geometrical isomers thereof, and solvates thereof such as hydrates;

in which formula (I'):
$A_1$ represents a radical containing at least one anionic, cationic, zwitterionic or neutral chromophore;
$X_1$ represents:
a linear or branched, saturated or unsaturated $C_1$-$C_{30}$ hydrocarbon-based chain, optionally interrupted and/or optionally terminated at one or both of its ends with one or more divalent groups or combinations thereof chosen from:
—N(R)—; —N$^+$(R)(R')—, Q$^-$; —O—; —S—; —C(O)—; —S(O)$_2$— with R and R', which may be identical or different, chosen from a hydrogen atom and a ($C_1$-$C_4$)alkyl, hydroxy($C_1$-$C_4$)alkyl or amino($C_1$-$C_4$)alkyl radical and Q$^-$ represents an organic or mineral anionic counterion;
an aromatic or non-aromatic, saturated or unsaturated, fused or non-fused (hetero)cyclic radical optionally comprising one or more identical or different, optionally substituted heteroatoms;
a divalent group or a combination chosen from:
—N(R)—; —N$^+$(R)(R')—, Q$^-$; —O—; —S—; —C(O)—; —SO$_2$— with R, R' and Q$^-$ as defined previously;
p is 0 or 1; and)
$R_{a1}$ represents an optionally substituted ($C_4$-$C_{20}$)alkenyl or optionally substituted ($C_4$-$C_{20}$)alkynyl group, preferably alkenyl;
it being understood that:
when the alkenyl or alkynyl group of $R_{a1}$ comprises 4 carbon atoms, then said group is linear and preferably comprises an unsaturation at the other end of the alkenyl or alkynyl group via which it is attached to the rest of the molecule, and in particular the unsaturation is a double bond, and preferably said group is attached to the rest of the molecule via a group other than a sulfonyl group —S(O)$_2$—;
the dye of formula (I') is other than the dyes (A) to (K) below:

(A)

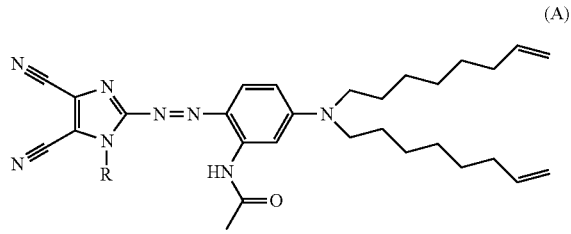

(B)

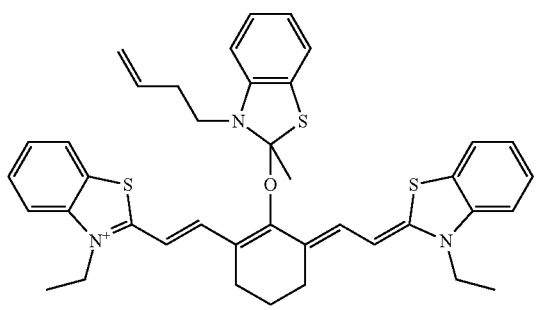

(C)

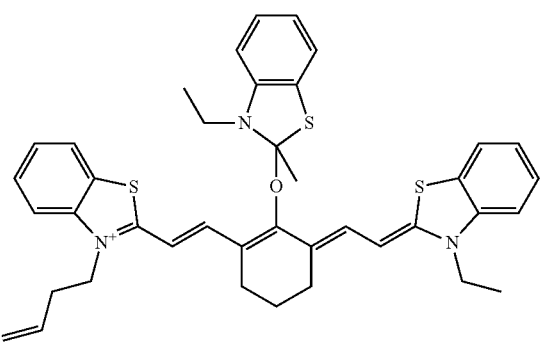

(D)

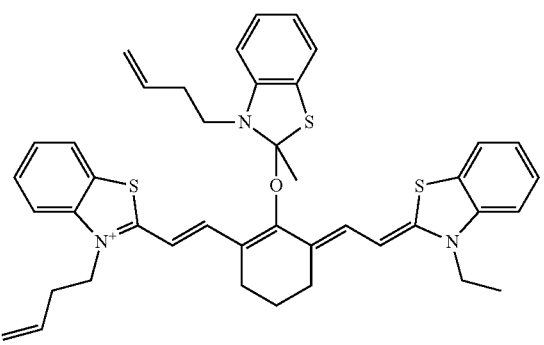

(E)

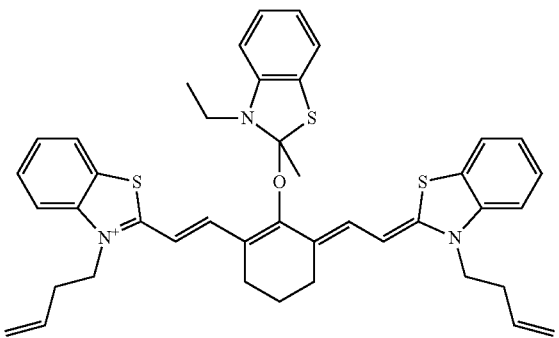

(F)

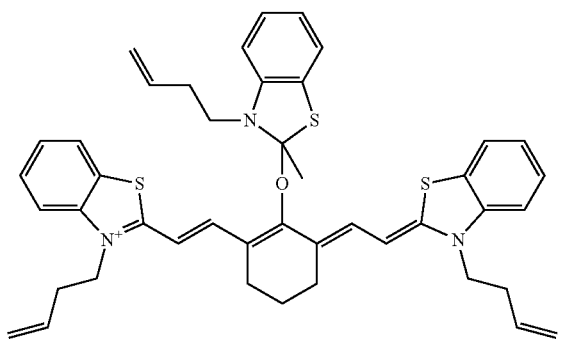

(G)

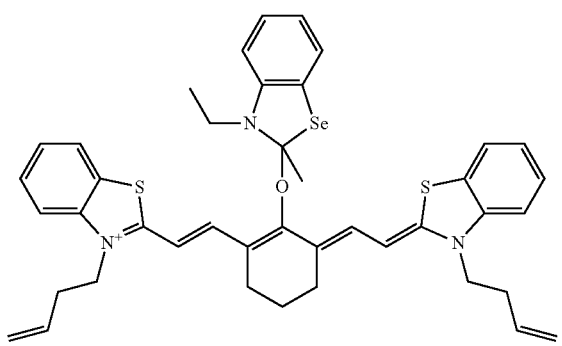

(H)

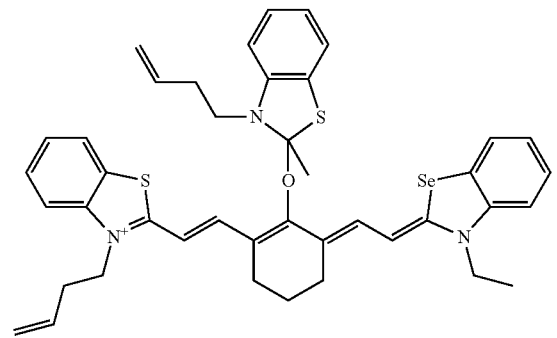

(I)

(J)

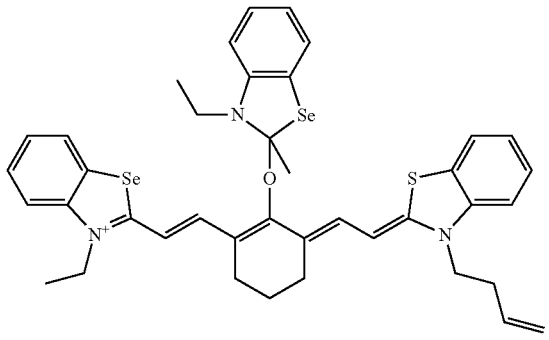

(K)

with R representing a hydrogen atom or a group chosen from: *—C(O)—O—(CH$_2$)$_3$—CH$_3$; *—C(O)—CH$_3$; *—C(O)—N(CH$_2$—CH$_3$)$_2$; and *—C(O)—N(CH$_2$—CH=CH$_2$)$_2$ A subject of the invention is also a cosmetic composition comprising:
- at least i) one dye and/or pigment as defined previously; and
- at least ii) one photoinitiator;

it being understood that:
- said composition does not comprise any photopolymerizable monomerspolymers; and
- when the dye or pigment comprises at least one alkenyl or alkynyl photoreactive group, then it is possible for said composition not to comprise ii) photoinitiator.

A subject of the invention is also the use of photoinitiator(s) for improving the dyeing and/or lightening of keratin materials, preferably keratin fibres, in the presence of at least one i) dye and/or pigment as defined previously and of at least iii) one light source preferably in the UV region; and the use of ii) photoinitiator(s) for improving the remanence of the dyeing and/or lightening of keratin materials, preferably keratin fibres, of i) dye(s) and/or pigment(s) as defined previously in the presence of at least iii) one light source preferably in the UV region or light from diodes.

A subject of the invention is also a multi-compartment kit or device comprising the ingredients i) and ii) as defined previously.

The dyeing process of the invention in particular makes it possible to dye in a remanent and odourless manner human keratin fibres such as the hair, while at the same time respecting the integrity of said fibres. The colorations performed using fluorescent dye(s) or pigment(s) make it possible to lighten keratin fibres even without the use of a chemical oxidizing agent such as hydrogen peroxide.

The colorations obtained are aesthetic, very strong and very fast with respect to common attacking factors such as sunlight, perspiration, sebum and other hair treatments such as successive shampooing. In addition, the colorations obtained according to the invention respect the cosmetic nature of the keratin materials. The intensity obtained is particularly noteworthy. This is likewise the case for the homogeneity of the colour from the root to the end or from one fibre to another.

For the purposes of the present invention, and unless otherwise indicated:

- a "dye" is a natural or synthetic, fluorescent or non-fluorescent, preferably coloured and/or fluorescent, compound, i.e. a compound comprising a chromophore which may be fluorescent. The term "dye" also means oxidation dyes (oxidation bases optionally combined with one or more couplers), and direct dyes that are soluble in cosmetically acceptable solvents, in particular aqueous or aqueous-alcoholic solvents;
- a "pigment" is a natural or synthetic, fluorescent or non-fluorescent coloured compound, which is sparingly soluble or insoluble in cosmetic solvents, i.e. especially insoluble in water or in aqueous-alcoholic solvents; Preferably, ingredient i) is one or more dyes, in particular direct dyes;
- a "chromophore" is a radical derived from a dye, i.e. a radical derived from a molecule that absorbs light in the visible radiation range that is visually and physiologically perceptible to the human eye, i.e. at an absorption wavelength $\lambda_{abs}$ inclusively between 400 and 800 nm; the chromophore may be fluorescent, i.e. it is capable of absorbing in the UV and visible radiation range at a wavelength $\lambda_{abs}$ of between 250 and 800 nm and capable of re-emitting in the visible range at an emission wavelength $\lambda_{em}$ of between 400 and 800 nm;
- a "chromophore" is said to be "cationic" if it comprises at least one cationic aryl or heteroaryl group as defined below;
- the dyes and/or pigments according to the invention contain one or more chromophores, and these dyes and/or pigments are capable of absorbing light at a wavelength $\lambda_{abs}$ particularly of between 400 and 700 nm inclusive;
- the "fluorescent" dyes and/or pigments according to the invention are dyes containing at least one fluorescent chromophore, and these compounds are capable of absorbing in the visible range at a wavelength $\lambda_{abs}$ particularly between 400 and 800 nm and of re-emitting in the visible range at a longer wavelength $\lambda_{em}$ than that absorbed, of between 400 and 800 nm. The difference between the absorption and emission wavelengths, also known as the Stoke's shift, is between 1 nm and 100 nm. More preferentially, fluorescent dyes are dyes that are capable of absorbing at a wavelength $\lambda_{abs}$ of between 420 nm and 550 nm and of re-emitting in the visible range at a wavelength $\lambda_{em}$ of between 470 and 600 nm;
- chromophores are said to be "different" when they differ in their chemical structure and may be chromophores derived from different families or from the same family on condition that they have different chemical structures: for example, the chromophores may be chosen from the family of azo dyes but differ in the chemical structure of the radicals constituting them or in the respective position of these radicals;
- a "cationic direct dye bearing a disulfide function" is a direct dye comprising one or more cationic chromophores that absorb light in the visible spectrum, and comprising one or more disulfide bonds: —S—S— between two carbon atoms and which is indirectly bonded to the chromophore(s) of the dye, i.e. between the chromophores and the —S—S— function(s) there is at least one methylene group;
- a "direct dye bearing a protected thiol function" is a direct dye comprising a chromophore, comprising a protected thiol function —SY in which Y is a protecting group known to those skilled in the art, for instance those described in the publications "*Protective Groups in Organic Synthesis*", T. W. Greene, John Wiley & Sons ed., NY, 1981, pp. 193-217; "*Protecting Groups*", P. Kocienski, Thieme, 3$^{rd}$ ed., 2005, chap. 5; and Ullmann's Encyclopedia, "*Peptide Synthesis*", pp. 4-5, 2005 Wiley-VCH Verlag GmbH & Co. KGaA, Weinheim 10.100214356007.a19 157; it being understood that said protected thiol function is indirectly bonded to the chromophore of the dye, i.e. between the chromophore and the function —SY there is at least one methylene group;
- a "direct dye bearing a thiol function" is a direct dye comprising a chromophore, and comprising a thiol function —SY' in which Y' is i) a hydrogen atom; ii) an alkali metal; iii) an alkaline-earth metal; iv) an ammonium group: $N^+R^\alpha R^\beta R^\gamma R^\delta$ or a phosphonium group: $P^+R^\alpha R^\beta R^\gamma R^\delta$ with $R^\alpha$, $R^\beta$, $R^\gamma$ and $R^\delta$, which may be identical or different, representing a hydrogen atom or a group $(C_1$-$C_4)$alkyl, preferentially comprising a thiol function —SH, it being understood that said thiol function is indirectly bonded to the chromophore of the dye, i.e. between the chromophore and the function —SY' there is at least one methylene group;
- a "disulfide heterocyclic radical" is a heterocyclic radical comprising in its ring, i.e. in the same ring and not in two different rings, a disulfide sequence —S—S— between two carbon atoms, said heterocycle possibly being substituted and preferentially not comprising in the ring an amido sequence: the heterocyclic radical may be illustrated by the following formula:

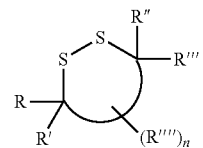

with R, R', R" and R'", which may be identical or different, representing substituents as defined for $R_5$, $R_6$, $R_9$ and $R_{10}$ previously, n representing an integer between 1 and 4, and R"", which may be identical or different, representing a substituent as defined for $R_7$ and $R_8$ previously;

- an "alkylene chain" represents a divalent $C_1$-$C_{20}$, particularly $C_1$-$C_6$ and more particularly $C_1$-$C_2$ chain when the chain is linear; optionally substituted with one or more identical or different groups chosen from hydroxyl, $(C_1$-$C_2)$alkoxy, (poly)hydroxy$(C_2$-$C_4)$alkoxy, (di)$(C_1$-$C_2)$ (alkyl)amino, $R^a$—$Z^a$—$C(Z^b)$—, and $R^a$—$Z^a$—S$(O)_t$— with $Z^a$, $Z^b$, which may be identical or different, representing an oxygen or sulfur atom, or a group $NR^{a'}$, $R^a$ representing an alkali metal, a hydrogen atom or an alkyl group, or alternatively is absent if another part of the molecule is cationic, and $R^{a'}$ representing a hydrogen atom or an alkyl group and t is equal to 1 or 2;
- an "optionally substituted saturated or unsaturated $C_1$-$C_{30}$ divalent hydrocarbon-based chain" represents a hydrocarbon-based chain, which is particularly a $C_1$-$C_8$ chain, optionally comprising one or more conjugated or unconjugated π double bonds, the hydrocarbon-based chain particularly being saturated; said chain is optionally substituted with one or more identical or different groups chosen from hydroxyl, ($C_1$-$C_2$)alkoxy, (poly) hydroxy($C_2$-$C_4$)alkoxy, (di)($C_1$-$C_2$) (alkyl)amino, $R^a$—$Z^a$—$C(Z^b)$—, and $R^a$—$Z^a$—$S(O)_t$— with $Z^a$, $Z^b$, which may be identical or different, representing an oxygen or sulfur atom, or a group $NR^{a'}$, $R^a$ representing an alkali metal, a hydrogen atom or an alkyl group, or alternatively is absent if another part of the molecule is cationic, and $R^{a'}$ representing a hydrogen atom or an alkyl group and t is equal to 1 or 2;

the "aryl" or "heteroaryl" radicals or the aryl or heteroaryl part of a radical may be substituted with at least one substituent borne by a carbon atom, chosen from:

a $C_1$-$C_{16}$ and preferably $C_1$-$C_8$ alkyl radical optionally substituted with one or more radicals chosen from hydroxyl, $C_1$-$C_2$ alkoxy, $C_2$-$C_4$ (poly)hydroxyalkoxy, acylamino, amino substituted with two $C_1$-$C_4$ alkyl radicals, which may be identical or different, optionally bearing at least one hydroxyl group, or the two radicals possibly forming, with the nitrogen atom to which they are attached, a saturated or unsaturated, optionally substituted 5- to 7-membered and preferably 5- or 6-membered heterocycle optionally comprising another nitrogen or non-nitrogen heteroatom;

a halogen atom;

a hydroxyl group;

a $C_1$-$C_2$ alkoxy radical;

a (poly)hydroxy($C_2$-$C_4$)alkoxy radical;

an amino radical;

a 5- or 6-membered heterocycloalkyl radical;

an optionally cationic 5- or 6-membered heteroaryl radical, preferentially imidazolium, optionally substituted with a ($C_1$-$C_4$)alkyl radical, preferentially methyl;

an amino radical substituted with one or two identical or different $C_1$-$C_6$ alkyl radicals, optionally bearing at least:
 i) one hydroxyl group,
 ii) one amino group optionally substituted with one or two optionally substituted $C_1$-$C_3$ alkyl radicals, it being possible for said alkyl radicals to form, with the nitrogen atom to which they are attached, a saturated or unsaturated and optionally substituted 5- to 7-membered heterocycle optionally comprising at least one other nitrogen or non-nitrogen heteroatom,
 iii) one quaternary ammonium group —$N^+R'R''R'''$, $M^-$ for which R', R'' and R''', which may be identical or different, represent a hydrogen atom, or a $C_1$-$C_4$ alkyl group; and $M^-$ represents the counterion of the organic or mineral acid or of the corresponding halide,
 iv) or an optionally cationic 5- or 6-membered heteroaryl radical, preferentially imidazolium, optionally substituted with a ($C_1$-$C_4$)alkyl radical, preferentially methyl;

an acylamino radical (—NR—C(O)—R') in which the radical R is a hydrogen atom, a $C_1$-$C_4$ alkyl radical optionally bearing at least one hydroxyl group and the radical R' is a $C_1$-$C_2$ alkyl radical; a carbamoyl radical (($R)_2$N—C(O)—) in which the radicals R, which may be identical or different, represent a hydrogen atom, a $C_1$-$C_4$ alkyl radical optionally bearing at least one hydroxyl group; an alkylsulfonylamino radical (R'—$S(O)_2$—N(R)—) in which the radical R represents a hydrogen atom, a $C_1$-$C_4$ alkyl radical optionally bearing at least one hydroxyl group and the radical R' represents a $C_1$-$C_4$ alkyl radical or a phenyl radical; an aminosulfonyl radical (($R)_2$N—$S(O)_2$—) in which the radicals R, which may be identical or different, represent a hydrogen atom or a $C_1$-$C_4$ alkyl radical optionally bearing at least one hydroxyl group, a carboxylic radical in acid form or salified form (preferably with an alkali metal or a substituted or unsubstituted ammonium);

a cyano group;

a nitro or nitroso group;

a polyhaloalkyl group, preferentially trifluoromethyl;

the cyclic or heterocyclic part of a non-aromatic radical may be substituted by at least one substituent chosen from the following groups:

hydroxyl, $C_1$-$C_4$ alkoxy or $C_2$-$C_4$ (poly)hydroxyalkoxy;

$C_1$-$C_4$ alkyl;

alkylcarbonylamino (R—C(O)—NR'—) in which the radical R' is a hydrogen atom or a $C_1$-$C_4$ alkyl radical optionally bearing at least one hydroxyl group, and the radical R is a $C_1$-$C_2$ alkyl radical or an amino radical optionally substituted with one or two $C_1$-$C_4$ alkyl groups, which may be identical or different, themselves optionally bearing at least one hydroxyl group, said alkyl radicals possibly forming, with the nitrogen atom to which they are attached, a saturated or unsaturated, optionally substituted 5- to 7-membered heterocycle optionally comprising at least one other nitrogen or non-nitrogen heteroatom;

alkylcarbonyloxy (R—C(O)—O—) in which the radical R is a $C_1$-$C_4$ alkyl radical or an amino group optionally substituted with one or two identical or different $C_1$-$C_4$ alkyl groups themselves optionally bearing at least one hydroxyl group, said alkyl radicals possibly forming with the nitrogen atom to which they are attached a saturated or unsaturated, optionally substituted 5- to 7-membered heterocycle, optionally comprising at least one other nitrogen or non-nitrogen heteroatom;

alkoxycarbonyl (R-G-C(O)—) in which the radical R is a $C_1$-$C_4$ alkoxy radical, G is an oxygen atom or an amino group optionally substituted with a $C_1$-$C_4$ alkyl group itself optionally bearing at least one hydroxyl group, said alkyl radical possibly forming with the nitrogen atom to which they are attached a saturated or unsaturated, optionally substituted 5- to 7-membered heterocycle, optionally comprising at least one other nitrogen or non-nitrogen heteroatom;

a cyclic or heterocyclic radical, or a non-aromatic part of an aryl or heteroaryl radical, may also be substituted with one or more oxo groups;

a "hydrocarbon-based chain" is "unsaturated" when it comprises one or more double bonds and/or one or more triple bonds;

an "aryl" radical represents a monocyclic or polycyclic, fused or non-fused carbon-based group containing from 6 to 22 carbon atoms, at least one ring of which is aromatic; preferentially, the aryl radical is a phenyl, biphenyl, naphthyl, indenyl, anthracenyl or tetrahydronaphthyl;

a "heteroaryl radical" represents an optionally cationic, 5- to 22-membered, monocyclic or polycyclic, fused or non-fused group, comprising from 1 to 6 heteroatoms chosen from nitrogen, oxygen, sulfur and selenium, at least one ring of which is aromatic; preferentially, a heteroaryl radical is chosen from acridinyl, benzimidazolyl, benzobistriazolyl, benzopyrazolyl, benzopyridazinyl, benzoquinolyl, benzothiazolyl, benzotriazolyl, benzoxazolyl, pyridinyl, tetrazolyl, dihydrothiazolyl, imidazopyridyl, imidazolyl, indolyl, isoquinolyl, naphthoimidazolyl, naphthoxazolyl, naphthopyrazolyl, oxadiazolyl, oxazolyl, oxazolopyridyl, phenazinyl, phenoxazolyl, pyrazinyl, pyrazolyl, pyrilyl, pyrazoyltriazyl, pyridyl, pyridinoimidazolyl, pyrrolyl, quinolyl, tetrazolyl, thiadiazolyl, thiazolyl, thiazolopyridinyl, thiazoylimidazolyl, thiopyrylyl, triazolyl, xanthyl and the ammonium salt thereof;

a "cyclic radical" is a non-aromatic, monocyclic or polycyclic, fused or non-fused cycloalkyl radical, containing from 5 to 22 carbon atoms, which may comprise one or more unsaturations;

a "heterocyclic radical" is a fused or non-fused, 5- to 22-membered monocyclic or polycyclic non-aromatic radical possibly containing one or two unsaturations, comprising from 1 to 6 heteroatoms chosen from nitrogen, oxygen, sulfur and selenium;

a "heterocycloalkyl radical" is a saturated heterocyclic radical;

a "cationic heteroaryl radical" is a heteroaryl group as defined previously, which comprises an endocyclic or exocyclic cationic group, when the charge is endocyclic, it is included in the electron delocalization via the mesomeric effect, for example it is a pyridinium, imidazolium or indolinium group:

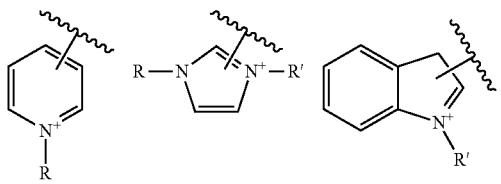

with R and R' being a heteroaryl substituent as defined previously and particularly a (hydroxy)($C_1$-$C_8$)alkyl group such as methyl;

when the charge is exocyclic, it is not included in the electron delocalization via the mesomeric effect, for example it is an ammonium or phosphonium substituent $R^+$ such as trimethylammonium, which is outside the heteroaryl such as pyridyl, indolyl, imidazolyl or naphthalimidyl in question:

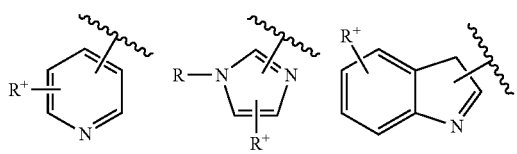

-continued

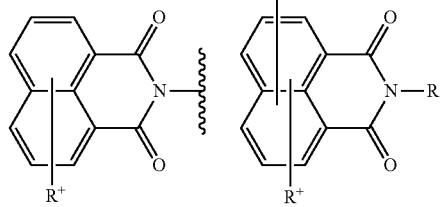

with R being a heteroaryl substituent as defined previously and $R^+$ an ammonium $R_aR_bR_cN^+$—, phosphonium $R_aR_bR_cP^+$— or ammonium $R_aR_bR_cN^+$—($C_1$-$C_6$) alkylamino group with $R_a$, $R_b$ and $R_c$, which may be identical or different, representing a hydrogen atom or a group ($C_1$-$C_8$)alkyl such as methyl;

a "cationic aryl bearing an exocyclic charge" is an aryl ring whose cationic group is outside said ring: it is especially an ammonium or phosphonium substituent $R^+$ such as trimethylammonium, which is outside the aryl such as phenyl or naphthyl:

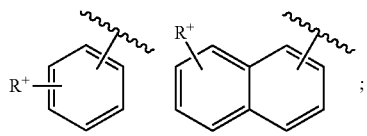

an "alkyl radical" is a linear or branched $C_1$-$C_{20}$ and preferably $C_1$-$C_8$ hydrocarbon-based radical;

an "alkenylene radical" is an alkyl radical as defined previously, which may contain from 1 to 4 conjugated or unconjugated double bonds —C=C—; the alkenylene group particularly contains 1 or 2 unsaturations;

the term "optionally substituted" applied to the alkyl, alkenyl or alkynyl radical implies that said alkyl, alkenyl or alkynyl radical may be substituted with one or more radicals chosen from the following radicals: i) hydroxyl, ii) $C_1$-$C_4$ alkoxy, iii) acylamino, iv) amino optionally substituted with one or two identical or different $C_1$-$C_4$ alkyl radicals, said alkyl radicals possibly forming with the nitrogen atom that bears them a 5- to 7-membered heterocycle optionally comprising another nitrogen or non-nitrogen heteroatom; v) or a quaternary ammonium group —$N^+R'R''R'''$, $M^-$ for which R', R'' and R''', which may be identical or different, represent a hydrogen atom or a $C_1$-$C_4$ alkyl group, or alternatively —$N^+R'R''R'''$ forms a heteroaryl such as imidazolium optionally substituted with a $C_1$-$C_4$ alkyl group, and $M^-$ represents the counterion of the organic or mineral acid or of the corresponding halide;

an "alkoxy radical" is an alkyl-oxy radical for which the alkyl radical is a linear or branched $C_1$-$C_{16}$ and preferentially $C_1$-$C_8$ hydrocarbon-based radical;

an "alkylthio radical" is an alkyl-S— radical for which the alkyl radical is a linear or branched $C_1$-$C_{16}$ and preferentially $C_1$-$C_8$ hydrocarbon-based radical;

when the alkoxy or alkylthio group is "optionally substituted", this implies that the alkyl group is optionally substituted as defined hereinabove;

the term "photolabile or photoreactive" group means a group which can generate at least one free radical from light source(s) such as the group $R_{a1}$ as defined in formula (Ia) below;

the "tone depth" is the unit known to hairstyling professionals, published in the book *Sciences des traitements capillaires* [Hair treatment sciences] by Charles Zviak, 1988, published by Masson, pp. 215 and 278; the tone depths range from 1 (black) to 10 (very light blonde), one unit corresponding to one tone; the higher the figure, the lighter the shade;

a "dark" keratin fibre is a keratin fibre whose lightness L* measured in the C.I.E. L*a*b* system is less than or equal to 45 and preferably less than or equal to 40, given that L*=0 is equivalent to black and L*=100 is equivalent to white;

"naturally or artificially dark hair" means hair whose tone depth is less than or equal to 6 (dark blonde) and preferably less than or equal to 4 (chestnut-brown). Artificially dyed hair is hair whose colour has been modified by a coloration treatment, for example a coloration with direct dyes or oxidation dyes;

the expression "at least one" means "one or more".

unless otherwise indicated, the limits delimiting the extent of a range of values are included in this range of values;

the term "optical lightening" means lightening that is visibly observable to the eye, obtained without the use of chemical oxidizing agents other than atmospheric oxygen, such as hydrogen peroxide or a system for generating hydrogen peroxide, or other chemical agents that may destroy the natural colour, especially the melanin of keratin fibres such as the hair.

One means for measuring the lightening effect given to the hair after application of the fluorescent dyes of the invention is to use the phenomenon of reflectance of the hair. Thus, for dark hair, more particularly hair whose tone depth is less than or equal to 6 (dark blonde), preferably less than or equal to 4 (chestnut-brown), it has been seen that there are regions for which the curve of reflectance as a function of the wavelength (between 500 and 700 nm) of hair treated with the composition comprising the fluorescent compound is higher than the curve corresponding to the untreated hair. Consequently, the hair appears lighter, without it being necessary to use a chemical oxidizing agent.

The fluorescent dyespigments are tested as follows:

What is concerned is the reflectance performance of the keratin fibres when they are irradiated with visible light in the wavelength range from 400 to 700 nanometers.

The curves of reflectance as a function of the wavelength, for hair treated with the composition of the invention and for untreated hair, are then compared.

The curve corresponding to the treated hair should show a reflectance in the wavelength range from 500 to 700 nanometers higher than the curve corresponding to the untreated hair. This means that, in the wavelength range from 500 to 700 nanometers, there is at least one "region" in which the reflectance curve corresponding to the treated keratin fibres is higher than the reflectance curve corresponding to the untreated keratin fibres. The term "higher" means a difference in reflectance of at least 0.05% and preferably of at least 0.1%. This does not prevent there from being, in the wavelength range from 500 to 700 nanometers, at least one region in which the reflectance curve corresponding to the treated hair is superposable on or lower than the reflectance curve corresponding to the untreated hair.

Preferably, the wavelength at which the difference is maximal between the reflectance curve for the treated keratin fibres and that for the untreated keratin fibres is in the wavelength range from 500 to 650 nanometers and preferably in the wavelength range from 550 to 620 nanometers.

The dyes of the invention especially containing alkenyl or alkynyl group(s) of formula (I') are moreover stable with respect to chemical oxidizing agents or atmospheric oxygen, and show satisfactory solubility in cosmetic dyeing media. These dyes extend the range of colours from yellows to violets. The dyes of the invention colour chromatically after application to keratin fibres, in a remanent manner with respect to external attacking factors, with little coloration selectivity between the root and the end, and on different types of fibres.

1. Dyes and/or Pigments:

1.a) Oxidation Dyes

According to one particular embodiment of the invention, ingredient i) is chosen from oxidation dyes.

The oxidation dyes may consist solely of oxidation bases. These bases may especially be chosen from para-phenylenediamines, bis(phenyl)alkylenediamines, para-aminophenols, ortho-aminophenols and heterocyclic bases, and the addition salts thereof.

In general, the concentration of the oxidation base(s) ranges from 0.0001% to 20% and preferably from 0.005% to 6% by weight, relative to the total weight of the composition.

The oxidation bases may be combined with couplers. Among these oxidation couplers mention may be made especially of meta-phenylenediamines, meta-aminophenols, meta-diphenols, naphthalene-based couplers and heterocyclic couplers, and the addition salts thereof.

In general, the concentration of the oxidation coupler(s) ranges from 0.0001% to 20% and preferably from 0.005% to 6% by weight, relative to the total weight of the composition.

In general, the addition salts with an acid that can be used for the oxidation bases and the couplers are chosen in particular from hydrochlorides, hydrobromides, sulfates, citrates, succinates, tartrates, lactates, tosylates, benzenesulfonates, phosphates and acetates.

1.b) Direct Dyes

According to one particular embodiment of the invention, the ingredient(s) i) as defined previously are direct dyes. Direct dyes comprise at least one photoreactive or photolabile group, i.e. a group which can generate at least one free radical from light source(s).

One particular embodiment of the invention concerns the ingredient(s) i) chosen from those comprising one or more photoreactive groups of formula (I) below:

$$A_1\text{-}(X_1)_p\text{—}R_{a1} \qquad (I)$$

the organic or mineral acid or base salts thereof, optical isomers thereof, geometrical isomers and tautomers thereof, and solvates thereof such as hydrates;

in which formula (I):)

$A_1$ represents a radical containing at least one anionic, cationic, zwitterionic or neutral coloured chromophore;

$R_{a1}$ represents a group chosen from:

i) optionally substituted $(C_4\text{-}C_{20})$alkenyl or optionally substituted $(C_4\text{-}C_{20})$alkynyl, particularly alkenyl, preferentially a $C_4\text{-}C_{10}$ alkenyl group, optionally substituted with an amino group and comprising at the end of said alkenyl group a double bond such as: —$CH_2$—$CH_2$—CH=$CH_2$;

ii) Asc or *—$C_{sat}(X'_1)_p$-Asc in which Asc represents a radical derived from ascorbic acid chosen from ascorbyl and dehydroascorbyl radicals, chosen from formulae (II-1) to (II-4), and which is linked to the rest of the molecule via one of the substituents $R_5$, $R_6$, $R_7$, $R_8$ or $R_9$, or alternatively said radical is linked to the rest of the molecule directly via one of the carbon atoms bearing the substituents $R_5$, $R_6$, $R_7$, $R_8$ or $R_9$, in which case one of these substituents is absent:

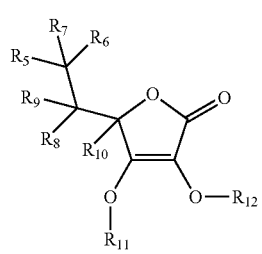

(II-1)

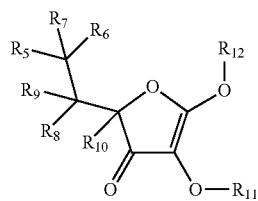

(II-2)

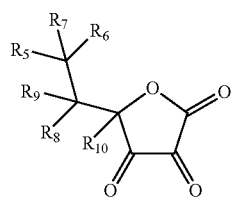

(II-3)

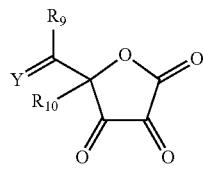

(II-4)

in which formulae (II-1) to (II-4):
$R_5$, $R_6$, $R_7$, $R_8$, $R_9$ and $R_{10}$, which may be identical or different, represent a hydrogen atom or a group chosen from: i) ($C_1$-$C_8$)alkyl, ii) hydroxyl, iii) carboxyl, iv) and —O-protected with a protecting group;
or alternatively $R_5$ and $R_9$ together form a divalent group —O—$(CR_aR_b)_n$—O— with $R_a$ and $R_b$, which may be identical or different, representing a hydrogen atom or a group ($C_1$-$C_8$)alkyl such as methyl or t-butyl, ($C_1$-$C_8$)alkoxy, aryl, (poly)halo($C_1$-$C_8$)alkyl such as trichloromethyl, and n being equal to 1, 2 or 3, and in particular $R_5$ and $R_9$ together form a divalent group —O—$CH_2$—$CH_2$—O— or —O—C($CH_3$)$_2$—O—;
$R_{11}$ and $R_{12}$, which may be identical or different, represent a hydrogen atom, an alkali metal, an alkaline-earth metal or a protecting group;
or alternatively $R_{11}$ and $R_{12}$ together form a divalent group —$(CR_aR_b)_n$— with $R_a$ and $R_b$ and n as defined previously;
Y represents an oxygen atom or a sulfur atom;
the asterisk * representing the point of attachment of the group $C_{sat}$ to the rest of the molecule;

iii) HET or *—$C_{sat}$—$(X'_1)_p$-HET in which HET represents a saturated or unsaturated, monocyclic or bicyclic 5- to 20-membered heterocyclic radical, comprising at least one nitrogen and sulfur atom, and may also comprise an oxygen atom, said oxygen atom possibly being on a carbonyl or non-carbonyl group;
more particularly, the nitrogen, sulfur and oxygen atoms being combined in the heterocycle according to the sequence: 1) —N—C(X)—X'—; 2) —X'—N—C(X)— and 3) —X'—N=C—X— with X and X', which may be identical or different, representing an oxygen or sulfur atom or a group N—R with R representing a hydrogen atom or a group ($C_1$-$C_6$) alkyl; and even more particularly the heterocycle is chosen from (a), (b), (c), (d), (e) and (f) below:

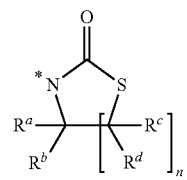

(a)

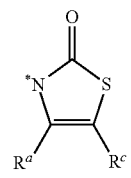

(b)

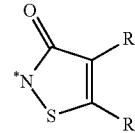

(c)

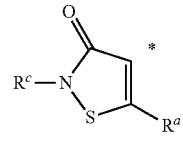

(d)

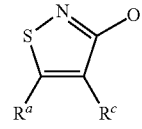

(e)

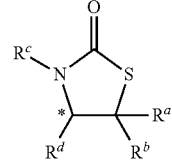

(f)

heterocycle (a), (b), (c), (d), (e) or (f) with:
n is 1 or 2;
$R_a$, $R_b$, $R_c$ and $R_d$, which may be identical or different, representing a hydrogen atom or a $C_1$-$C_4$ alkyl group, or alternatively $R_a$ and $R_c$ or two contiguous $R_c$ when n is 2, may form, together with the carbon atoms that bear them, a (hetero)cycloalkyl, heterocycloalkenyl or heteroaryl group, preferably a ($C_5$-$C_7$)cycloalkyl such as cyclopentyl or a ($C_5$-$C_7$)cycloalkenyl such as cyclopentenyl;

the asterisk * representing the point of attachment of the heterocycle to the rest of the molecule;

iv) HET' or *—$C_{sat}$—$(X'_1)_{p'}$-HET in which HET' represents a disulfide heterocyclic radical such as that of formula (g) linked to the rest of the molecule via one of the substituents $R_5$, $R_6$, $R_7$, $R_8$, $R_9$ or $R_{10}$, or alternatively said radical is linked to the rest of the molecule directly via one of the carbon atoms of the heterocyclic radical in the alpha or beta position or, when q is equal to 2 or 3, in the gamma position, in which case one of the substituents $R_5$, $R_6$, $R_7$, $R_8$, $R_9$ or $R_{10}$ is absent:

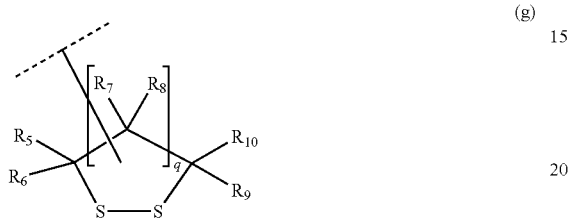
(g)

in which formula (g) $R_5$, $R_6$, $R_9$ and $R_{10}$, which may be identical or different, represent a hydrogen atom or a group chosen from: i) ($C_1$-$C_8$)alkyl, ii) aryl, iii) hydroxyl, iv) (di)($C_1$-$C_8$)(alkyl)amino, v) ($C_1$-$C_8$) alkoxy, vi) (poly)hydroxy($C_1$-$C_8$)alkyl, vii) (di)($C_1$-$C_8$) (alkyl)amino($C_1$-$C_8$)alkyl, viii) carboxyl, ix) carboxy ($C_1$-$C_3$)alkyl, x) (di)($C_1$-$C_8$)(alkyl)aminocarbonyl($C_1$-$C_8$)alkyl, and xii) ($C_1$-$C_8$)(alkyl)carbonyl($C_1$-$C_8$) (alkyl)amino($C_1$-$C_8$)alkyl;

$R_7$ and $R_8$, which may be identical or different, represent a hydrogen atom or a group chosen from: i) ($C_1$-$C_8$)alkyl, ii) aryl, iii) hydroxyl, iv) (di)($C_1$-$C_8$) (alkyl)amino, v) ($C_1$-$C_8$)alkoxy, vi) (poly)hydroxy ($C_1$-$C_8$)alkyl, vii) (di)($C_1$-$C_8$)(alkyl)amino($C_1$-$C_8$) alkyl, viii) carboxyl, ix) carboxy($C_1$-$C_8$)alkyl, x) (di)($C_1$-$C_8$)(alkyl)aminocarbonyl($C_1$-$C_8$)alkyl, and xii) ($C_1$-$C_8$)(alkyl)carbonyl($C_1$-$C_8$)(alkyl)amino($C_1$-$C_8$)alkyl; particularly, $R_7$ and $R_8$ are chosen from a hydrogen atom and a ($C_1$-$C_4$)alkyl group such as methyl;

q represents an integer between 1 and 3 inclusive and particularly between 1 and 2;

it being understood that when q is equal to 2 or 3, then the groups $R_7$ and $R_8$ may be identical or different; preferentially, q is 1; and more particularly all the substituents $R_1$ to $R_6$ represent a hydrogen atom;

v) *—$C_{sat}$—S—U in which formula:
U represents a radical chosen from a) *—S—$C'_{sat}$—$(X'_1)_{p'}$-$A'_1$, and b) *—Y;
Y represents i) a hydrogen atom; or ii) a thiol-function protecting group;
$A'_1$ represents a radical containing at least one anionic, cationic or neutral coloured chromophore;

vi) *—$C(Y_a)$—$Y_b$—$(Y_c)_n$—$R^a$; *—$(Y_c)_n$—$Y_b$—C $(Y_a)$—$R^a$; *—$S(O)_m$—$Y_b$—$(Y_c)_n$—$R^a$; *—$(Y_c)_n$—$Y_b$—$S(O)_m$—$R^a$; *—$P(O)[Y_b$—$(Y_c)_n$—$R^a]_q(R^c)_r$ or *—$(Y_c)_n$—$Y_b$—$P(O)[Y_b$—$(Y_c)_n$—$R^a]_q(R^c)_r\dot{R}^a$ in which formulae:

$Y_a$, $Y_b$ and $Y_c$, which may be identical or different, represent an oxygen or sulfur atom or a divalent amino group —$N(R^b)$—
$R^a$ and $R^c$, which may be identical or different, represent a hydrogen atom, an optionally substituted ($C_1$-$C_{10}$)alkyl group, an optionally substituted ($C_1$-$C_{10}$)alkoxy group, an optionally substituted ($C_1$-$C_{10}$) alkylthio group, a group (di)($C_1$-$C_{10}$)(alkyl)amino, the alkyl group(s) of the amino being optionally substituted, optionally substituted (hetero)aryl, optionally substituted (hetero)aryloxy, optionally substituted (hetero)arylthio;
$R^b$ represents a hydrogen atom or an optionally substituted ($C_1$-$C_{10}$)alkyl or optionally substituted (hetero) aryl group;
n is 0 or 1;
m is 1 or 2;
q is 1, 2, 3 and r is 0, 1, or 2 with q+r=3;
$X_1$ and $X'_1$, which may be identical or different, represent:
a linear or branched, saturated or unsaturated divalent $C_1$-$C_{30}$ hydrocarbon-based chain, optionally interrupted and/or optionally terminated at one or both of its ends with one or more divalent groups or combinations thereof chosen from:
—N(R)—; —$N^+$(R)(R')—, $Q^-$; —O—; —S—; —S(O)—, —$S(O)_2$—, —C(O)—; —$S(O)_2$— with R and R', which may be identical or different, chosen from a hydrogen atom and a $C_1$-$C_4$ alkyl, hydroxy($C_1$-$C_8$)alkyl or amino($C_1$-$C_8$)alkyl radical and $Q^-$ represents an organic or mineral anionic counterion;
an aromatic or non-aromatic, saturated or unsaturated, fused or non-fused (hetero)cyclic radical optionally comprising one or more identical or different, optionally substituted heteroatoms;
preferentially, the divalent group(s) or combinations thereof are chosen from —O—; —N(R)—; —C(O)— with R chosen from a hydrogen atom and a $C_1$-$C_4$ alkyl radical;
p and p', which may be identical or different, represent an integer equal to 0 or 1; and
$C_{sat}$ and $C'_{sat}$, which may be identical or different, represent an optionally cyclic, optionally substituted linear or branched $C_1$-$C_{18}$ alkylene chain.

The Cosmetically Acceptable Salts of Organic or Mineral Acid and Counterions of the Dyes and/or Pigments of the Invention:

The compounds of formula (I) according to the invention may be cationic, anionic, zwitterionic or neutral;
when the compound is cationic or anionic, then an organic or mineral counterion, or several counterions or a mixture of counterions, are present to ensure the electrical neutrality,
or alternatively one or more groups in the compound can ensure the electrical neutrality, for example if the rest of the compound is cationic, with groups —$O^-$ (oxalate), —$COO^-$ (carboxylate), $R_3N^+$— (ammonium), or $R_3P^+$— (phosphonium), it will then be referred to as a zwitterion;
when the compound is anionic, then the organic or mineral counterion(s) are cationic, preferentially chosen from mineral cations such as alkali metals or alkaline-earth metals such as Na, Mg, K and Ca, and organic cations such as ammonium $NH_4^+$ or (di/tri)($C_1$-$C_8$)alkylammonium,
when the compound is cationic, then the counterion(s) are anionic,
an "anionic counterion" means an anion or an anionic group derived from an organic or mineral acid salt which counterbalances the cationic charge of the dye; more particularly, the anionic counterion is chosen from: i) halides such as chloride or bromide; ii) nitrates; iii) sulfonates, including $C_1$-$C_6$ alkylsulfonates: Alk-S (O)₂O⁻ such as methanesulfonate or mesylate and ethanesulfonate; iv) arylsulfonates: Ar—S(O)₂O⁻ such as benzenesulfonate and toluenesulfonate or tosylate; v) citrate; vi) succinate; vii) tartrate; viii) lactate; ix) alkyl sulfates: Alk-O—S(O)O⁻ such as methyl sulfate and ethyl sulfate; x) aryl sulfates: Ar—O—S(O)O⁻ such as benzene sulfate and toluene sulfate; xi) alkoxy sulfates: Alk-O—S(O)₂O⁻ such as methoxy sulfate and ethoxy sulfate; xii) aryloxy sulfates: Ar—O—S(O)₂O⁻, xiii) phosphates O=P(OH)₂—O⁻, O=P(O⁻)₂—OHO=P(O⁻)₃, HO—[P(O)(O⁻)]$_w$—P(O)(O⁻)₂ with w being an integer; xiv) acetate; xv) triflate; and xvi) borates such as tetrafluoroborate, xvii) disulfate (O=)₂S(O⁻)₂ or SO₄²⁻ and monosulfate HSO₄⁻;

the anionic counterion, derived from an organic or mineral acid salt, ensures the electrical neutrality of the molecule; thus, it is understood that when the anion comprises several anionic charges, then the same anion may serve for the electrical neutrality of several cationic groups in the same molecule or else may serve for the electrical neutrality of several molecules; for example, a disulfide dye of formula (I) which contains two cationic chromophores may contain either two "singly charged" anionic counterions or a "doubly charged" anionic counterion such as (O=)₂S(O⁻)₂ or O=P(O⁻)₂—OH;

moreover, the addition salts that may be used in the context of the invention are especially chosen from addition salts with a cosmetically acceptable base such as basifying agents as defined below, for instance alkali metal hydroxides, such as sodium hydroxide or potassium hydroxide, aqueous ammonia, amines or alkanolamines;

an "organic or mineral acid salt" is more particularly chosen from a salt derived from an "organic or mineral acid" chosen from i) hydrochloric acid HCl, ii) hydrobromic acid HBr, iii) sulfuric acid H2SO4, iv) alkylsulfonic acids: Alk-S(O)₂OH such as methanesulfonic acid and ethanesulfonic acid; v) arylsulfonic acids: Ar—S(O)₂OH such as benzenesulfonic acid and toluenesulfonic acid; vi) citric acid; vii) succinic acid; viii) tartaric acid; ix) lactic acid; x) alkoxysulfinic acids: Alk-O—S(O)OH such as methoxysulfinic acid and ethoxysulfinic acid; xi) aryloxysulfinic acids such as tolueneoxysulfinic acid and phenoxysulfinic acid; xii) phosphoric acid H₃PO₄; xiii) acetic acid CH₃COOH; xiv) triflic acid CF₃SO₃H; and xv) tetrafluoroboric acid HBF₄, an "organic or mineral base salt" is chosen from a salt derived from an "organic or mineral" base such as the basifying agents as defined below, for instance alkali metal hydroxides such as sodium hydroxide or potassium hydroxide, aqueous ammonia, amines or alkanolamines, chosen in particular from hydroxides of alkali metals or alkaline-earth metals such as Na, Mg, K and Ca, and organic cations such as ammonium NH₄⁺ or (di/tri)(C₁-C₈)alkylammonium, and also other bases such as the basifying agents used below for adjusting the pH.

1.1 Chromophores A₁ and A'₁:

The radicals A₁ and/or A'₁ of formula (I) may contain one or more chromophores, which may be identical or different, it being understood that at least one chromophore is coloured.

As coloured chromophores useful in the present invention, mention may be made of those derived from the following dyes: acridines; acridones; anthranthrones; anthrapyrimidines; anthraquinones; azines; (poly)azos, hydrazono or hydrazones, in particular arylhydrazones; azomethines; benzanthrones; benzimidazoles; benzimidazolones; benzindoles; benzoxazoles; benzopyrans; benzothiazoles; benzoquinones; bisazines; bis-isoindolines; carboxanilides; coumarins; cyanins such as azacarbocyanins, diazacarbocyanins, diazahemicyanins, hemicyanins, or tetraazacarbocyanins; diazines; diketopyrrolopyrroles; dioxazines; diphenylamines; diphenylmethanes; dithiazines; flavonoids such as flavanthrones and flavones; fluorindines; formazans; indamines; indanthrones; indigoids and pseudoindigoids; indophenols; indoanilines; isoindolines; isoindolinones; isoviolanthrones; lactones; (poly)methines such as dimethines of stilbene or styryl type; naphthalimides; naphthanilides; naphtholactams; naphthoquinones; nitro, especially nitro(hetero)aromatics; oxadiazoles; oxazines; perilones; perinones; perylenes; phenazines; phenoxazine; phenothiazines; phthalocyanin; polyenes/carotenoids; porphyrins; pyranthrones; pyrazolanthrones; pyrazolones; pyrimidinoanthrones; pyronines; quinacridones; quinolines; quinophthalones; squaranes; tetrazoliums; thiazines; thioindigo; thiopyronines; triarylmethanes, or xanthenes.

Among the azo compounds, mention may be made particularly of those in the *Kirk Othmer Encyclopedia of Chemical Technology*, "Dyes, Azo", J. Wiley & Sons, updated on 19 Apr. 2010.

Particularly, the chromophores A₁ and A'₁ are chosen from those derived from (poly)azo dyes such as (di)azo dyes, hydrazono dyes and (poly)methine dyes such as styryls and anthraquinones, or naphthalimides. Preferably, the latter chromophores are cationic.

According to a preferred embodiment of the invention, the chromophores A₁ and A'₁ are coloured and chosen from cationic chromophores, preferentially those known as "basic dyes".

Mention may be made of the cationic hydrazono chromophores of formulae (IIIa) and (III'a), the azo chromophores (IVa) and (IV'a) and the diazo chromophores (Va) below:

(IIIa)

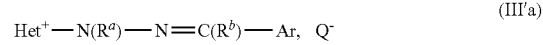

(III'a)

(IVa)

(IV'a) and

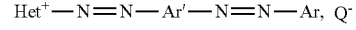

(Va)

formulae (IIIa), (III'a), (IVa), (IV'a) and (Va) with:

Het⁺ representing a cationic heteroaryl radical, preferably bearing an endocyclic cationic charge, such as imidazolium, indolium or pyridinium, optionally substituted preferentially with one or more (C₁-C₈)alkyl groups such as methyl;

Ar⁺ representing an aryl radical, such as phenyl or naphthyl, bearing an exocyclic cationic charge, preferentially ammonium, particularly tri(C₁-C₈)alkylammonium such as trimethylammonium;

Ar represents an aryl group, especially phenyl, which is optionally substituted, preferentially with one or more electron-donating groups such as i) optionally substituted (C₁-C₈)alkyl, ii) optionally substituted (C₁-C₈) alkoxy, iii) (di)(C₁-C₈)(alkyl)amino optionally substituted on the alkyl group(s) with a hydroxyl group, iv) aryl($C_1$-$C_8$)alkylamino, v) optionally substituted N—($C_1$-$C_8$)alkyl-N-aryl($C_1$-$C_8$)alkylamino or alternatively Ar represents a julolidine group;

Ar' is an optionally substituted divalent (hetero)arylene group such as phenylene, particularly para-phenylene, or naphthalene, which are optionally substituted, preferentially with one or more groups ($C_1$-$C_8$)alkyl, hydroxyl or ($C_1$-$C_8$)alkoxy;

Ar" is an optionally substituted (hetero)aryl group such as phenyl or pyrazolyl, which are optionally substituted, preferentially with one or more groups ($C_1$-$C_8$)alkyl, hydroxyl, (di)($C_1$-$C_8$)(alkyl)amino, ($C_1$-$C_8$)alkoxy or phenyl;

$R^a$ and $R^b$, which may be identical or different, representing a hydrogen atom or a group ($C_1$-$C_8$)alkyl, which is optionally substituted, preferentially with a hydroxyl group;

or alternatively the substituent $R^a$ with a substituent of $Het^+$ and/or $R^b$ with a substituent of Ar form, together with the atoms that bear them, a (hetero)cycloalkyl; particularly, $R^a$ and $R^b$ representing a hydrogen atom or a group ($C_1$-$C_4$)alkyl, which is optionally substituted with a hydroxyl group;

$Q^-$ represents an organic or mineral anionic counterion such as a halide or an alkyl sulfate;

it being understood that the chromophore (IIIa), (III'a), (IVa), (IV'a) or (Va) is linked to the rest of the molecule of formula (I) via $Het^+$, $Ar^+$, Ar or Ar".

Mention may be made in particular of the azo and hydrazono chromophores bearing an endocyclic cationic charge of formulae (IIIa), (III'a) and (IVa) as defined previously. More particularly those of formulae (IIIa), (III'a) and (IVa) derived from the dyes described in patent applications WO 95/15144, WO 95/01772 and EP-714954.

Preferentially derived from the following derivatives:

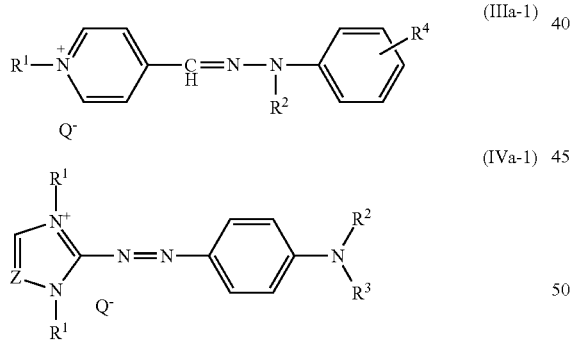

formulae (III-1) and (IV-1) with:
$R^1$ representing a group ($C_1$-$C_4$)alkyl such as methyl;
$R^2$ and $R^3$, which are identical or different, represent a hydrogen atom or a ($C_1$-$C_4$)alkyl group, such as methyl; and
$R^4$ represents a hydrogen atom or an electron-donating group such as optionally substituted ($C_1$-$C_8$)alkyl, optionally substituted ($C_1$-$C_8$)alkoxy, or (di)($C_1$-$C_8$)(alkyl)amino optionally substituted on the alkyl group(s) with a hydroxyl group; particularly, $R^4$ is a hydrogen atom,
Z represents a CH group or a nitrogen atom, preferentially CH,
$Q^-$ is as defined previously;

it being understood that the chromophore (IIa-1) or (IVa-1) is linked to the rest of the molecule of formula (I) by $R^1$ or $R^4$, in which case one of the hydrogen atoms of $R^1$ or $R^4$ is substituted with X' if p=1 or $C_{sat}$ if p=0.

Particularly, the chromophores (IIIa-1) and (IVa-1) are chosen from Basic Red 51, Basic Yellow 87 and Basic Orange 31 or derivatives thereof:

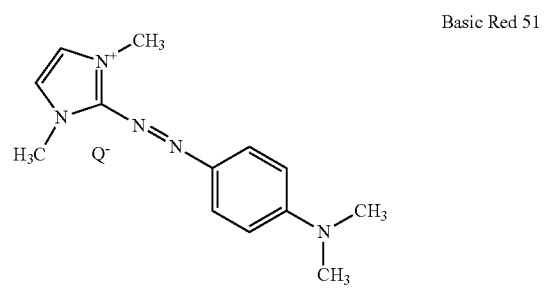

Basic Red 51

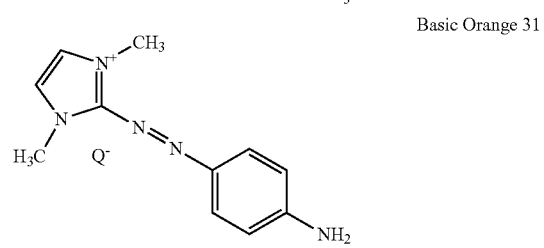

Basic Orange 31

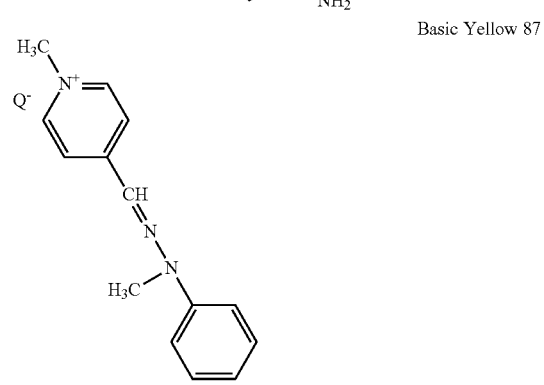

Basic Yellow 87 with Q' as defined previously, particularly a halide such as chloride or an alkyl sulfate such as methyl sulfate or mesityl.

According to another particular embodiment of the invention, the chromophore $A_1$ is chosen from anionic chromophores, especially those derived from direct dyes known as "Acid dyes". More particularly, the anionic chromophore $A_1$ is chosen from (poly)azo dyes such as anionic (di)azo, anthraquinone, naphthoquinone, triarylmethane and nitro dyes, xanthene derivatives, quinoline derivatives and indoles. Mention may be made of the anionic chromophores of formulae (VIa) to (XVIIa) below:

a) The Anionic Diaryl Azo Chromophores of Formula (VIa) or (VIIa):

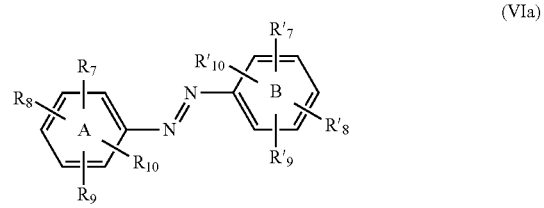

(VIa)

-continued (VIIa)

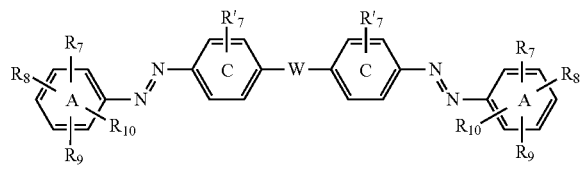

in which formulae (VIa) and (VIIa):

$R_7$, $R_8$, $R_9$, $R_{10}$, $R'_7$, $R'_8$, $R'_9$ and $R'_{10}$, which may be identical or different, represent a hydrogen atom or a group chosen from:

($C_1$-$C_8$)alkyl;

($C_1$-$C_8$)alkoxy, ($C_1$-$C_8$)alkylthio;

hydroxyl, mercapto;

nitro;

$R^o$—C(X)—X'—, $R^o$—X'—C(X)—, $R^o$—X'—C(X)—X"— with $R^o$ representing a hydrogen atom or a group ($C_1$-$C_8$)alkyl or aryl; X, X' and X", which may be identical or different, representing an oxygen or sulfur atom, or NR with R representing a hydrogen atom or a group ($C_1$-$C_8$)alkyl;

$(O)_2S(O^-)$—, $M^+$ with $M^+$ representing a hydrogen atom or an organic or mineral cationic counterion;

$(O)CO^-$—, $M^+$ with $M^+$ as defined previously;

R"—$S(O)_2$—, with R" representing a hydrogen atom, an alkyl group, an aryl group, (di)($C_1$-$C_8$)(alkyl)amino, aryl($C_1$-$C_8$)(alkyl)amino; preferentially a phenylamino or phenyl group;

R'"—$S(O)_2$—X'— with R'" representing a group ($C_1$-$C_8$)alkyl, optionally substituted aryl, X' as defined previously;

(di)($C_1$-$C_8$)(alkyl)amino;

aryl($C_1$-$C_8$)(alkyl)amino optionally substituted with one or more groups chosen from i) nitro; ii) nitroso; iii) $(O)_2S(O^-)$—, $M^+$ and iv) alkoxy with $M^+$ as defined previously;

optionally substituted heteroaryl; preferentially a benzothiazolyl group;

cycloalkyl; especially cyclohexyl,

Ar—N═N— with Ar representing an optionally substituted aryl group, preferentially a phenyl optionally substituted with one or more groups ($C_1$-$C_8$)alkyl, $(O)_2S(O^-)$—, $M^+$ or phenylamino;

or alternatively two contiguous groups $R_7$ with $R_8$ or $R_8$ with $R_9$ or $R_9$ with $R_{10}$ together form a fused benzo group A'; and R'$f_7$ with R'$_8$ or R'$_8$ with R'$_9$ or R'$_9$ with R'$_{10}$ together form a fused benzo group B; with A' and B' optionally substituted with one or more groups chosen from i) nitro; ii) nitroso; iii) $(O)_2S(O^-)$—, $M^+$; iv) hydroxyl; v) mercapto; vi) (di)(alkyl)amino; vii) $R^o$—C(X)—X'—; viii) $R^o$—X'—C(X)—; ix) $R^o$—X'—C(X)—X"—; x) Ar—N═N— and xi) optionally substituted aryl($C_1$-$C_8$)(alkyl)amino; with $M^+$, $R^o$, X, X', X" and Ar as defined previously;

W represents a sigma bond σ, an oxygen or sulfur atom, or a divalent radical i) —NR— with R as defined previously, or ii) methylene —C($R_a$)($R_b$)— with $R_a$ and $R_b$, which may be identical or different, representing a hydrogen atom or an aryl group, or alternatively $R_a$ and $R_b$ form, together with the carbon atom that bears them, a spiro cycloalkyl; preferentially W represents a sulfur atom or $R_a$ and $R_b$ together form a cyclohexyl;

it being understood that:

the chromophore (VIa) or (VIIa) comprises at least one sulfonate radical $(O)_2S(O^-)$—, $M^+$ or a carboxylate radical $(O)CO^-$—, $M^+$ on one of the rings A, B, or C; preferentially sodium sulfonate;

the chromophore (VIa) or (VIIa) is linked to the rest of the molecule of formula (I) via one of the rings A, B, or C, in which case one of the substituents is absent and the carbon atom of one of the rings where said substituent is absent is linked to the rest of the molecule.

As examples of chromophores of formula (VIa) derived from dyes, mention may be made of: Acid Red 1, Acid Red 4, Acid Red 13, Acid Red 14, Acid Red 18, Acid Red 27, Acid Red 32, Acid Red 33, Acid Red 35, Acid Red 37, Acid Red 40, Acid Red 41, Acid Red 42, Acid Red 44, Acid Red 68, Acid Red 73, Acid Red 135, Acid Red 138, Acid Red 184, Food Red 1, Food Red 13, Acid Orange 6, Acid Orange 7, Acid Orange 10, Acid Orange 19, Acid Orange 20, Acid Orange 24, Acid Yellow 9, Acid Yellow 36, Acid Yellow 199, Food Yellow 3; Acid Violet 7, Acid Violet 14, Acid Blue 113, Acid Blue 117, Acid Black 1, Acid Brown 4, Acid Brown 20, Acid Black 26, Acid Black 52, Food Black 1, Food Black 2; and as examples of chromophores of formula (VIIa) derived from dyes, mention may be made of: Acid Red 111, Acid Red 134, Acid yellow 38.

b) The Anionic Pyrazolone Azo Chromophores of Formula (VIIIa) or (IXa):

(VIIIa)

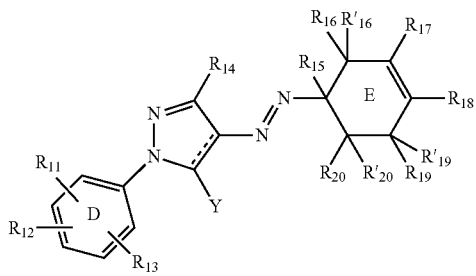

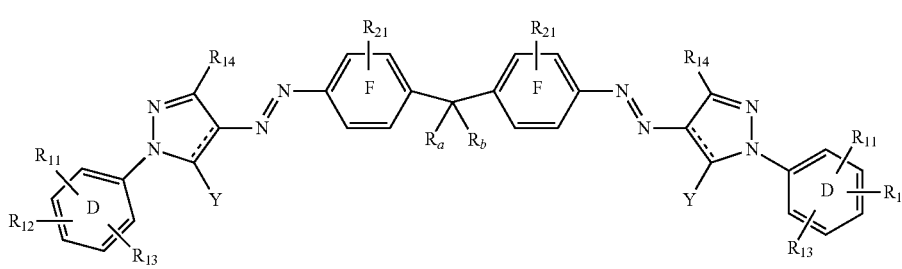
(IXa)

in which formulae (VIIIa) and (IXa):

$R_{11}$, $R_{12}$ and $R_{13}$, which may be identical or different, represent a hydrogen or halogen atom, an alkyl group or —(O)$_2$S(O$^-$), M$^+$ with M$^+$ as defined previously;

$R_{14}$ represents a hydrogen atom, a group (C$_1$-C$_8$)alkyl or a group —C(O)O$^-$, M$^+$ with M$^+$ as defined previously;

$R_{15}$ represents a hydrogen atom;

$R_{16}$ represents an oxo group, in which case R'$_{16}$ is absent, or alternatively $R_{15}$ with $R_{16}$ together form a double bond;

$R_{17}$ and $R_{18}$, which may be identical or different, represent a hydrogen atom, or a group chosen from:

(O)$_2$S(O$^-$)—, M$^+$ with M$^+$ as defined previously;

Ar—O—S(O)$_2$— with Ar representing an optionally substituted aryl group, preferentially a phenyl optionally substituted with one or more groups (C$_1$-C$_8$)alkyl;

$R_{19}$ and $R_{20}$ together form either a double bond, or a benzo group D, which is optionally substituted;

R'$_{16}$, R'$_{19}$ and R'$_{20}$, which may be identical or different, represent a hydrogen atom or a group (C$_1$-C$_8$)alkyl, or hydroxyl;

$R_{21}$ represents a hydrogen atom or a (C$_1$-C$_8$)alkyl or (C$_1$-C$_8$)alkoxy group;

$R_a$ and $R_b$, which may be identical or different, are as defined previously, preferentially $R_a$ represents a hydrogen atom and $R_b$ represents an aryl group;

Y represents either a hydroxyl group or an oxo group;

---- represents a single bond when Y is an oxo group; and represents a double bond when Y represents a hydroxyl group;

it being understood that:

the chromophore (VIIIa) or (IXa) comprises at least one sulfonate radical (O)$_2$S(O$^-$)—, M$^+$ or a carboxylate radical —C(O)O$^-$, M$^+$ on one of the rings D or E; preferentially sodium sulfonate;

the chromophore (VIIIa) or (IXa) is linked to the rest of the molecule of formula (I) via one of the rings D, E, or F, in which case one of the substituents is absent and the carbon atom of one of the rings where said substituent is absent is linked to the rest of the molecule.

As examples of chromophores of formula (VIIIa) derived from dyes, mention may be made of: Acid Red 195, Acid Yellow 23, Acid Yellow 27, Acid Yellow 76, and as examples of chromophores of formula (IXa) derived from dyes, mention may be made of: Acid Yellow 17.

c) The Anionic Anthraquinone Chromophores of Formula (Xa) or (XIa):

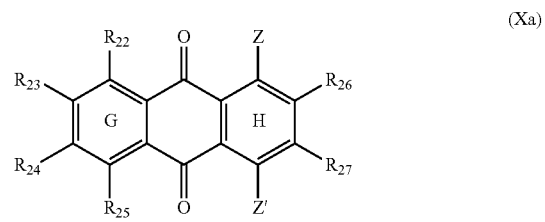
(Xa)

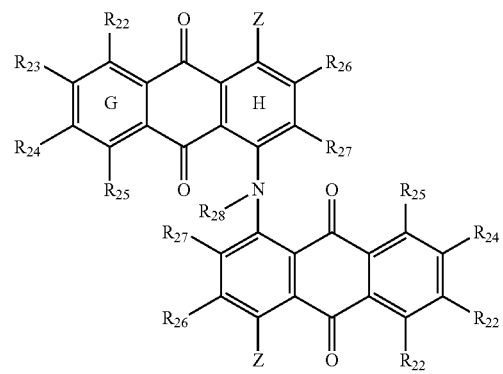
(XIa)

in which formulae (Xa) and (XIa):

$R_{22}$, $R_{23}$, $R_{24}$, $R_{25}$, $R_{26}$ and $R_{27}$, which may be identical or different, represent a hydrogen or halogen atom or a group chosen from:

(C$_1$-C$_8$)alkyl;

hydroxyl, mercapto;

(C$_1$-C$_8$)alkoxy, (C$_1$-C$_8$)alkylthio;

aryloxy or arylthio optionally substituted, preferentially substituted with one or more groups chosen from alkyl and (O)$_2$S(O$^-$)—, M$^+$ with M$^+$ as defined previously;

aryl(C$_1$-C$_8$)(alkyl)amino optionally substituted with one or more groups chosen from alkyl and (O)$_2$S(O$^-$)—, M$^+$ with M$^+$ as defined previously;

(di)(C$_1$-C$_8$)(alkyl)amino;

(di)(hydroxy(C$_1$-C$_8$)alkyl)amino;

(O)$_2$S(O$^-$)—, M$^+$ with M$^+$ as defined previously;

Z' represents a hydrogen atom or a group NR$_{28}$R$_{29}$ with $R_{28}$ and $R_{29}$, which may be identical or different, representing a hydrogen atom or a group chosen from:

(C$_1$-C$_8$)alkyl;

polyhydroxy(C$_1$-C$_8$)alkyl such as hydroxyethyl;

aryl optionally substituted with one or more groups, particularly i) (C$_1$-C$_8$)alkyl such as methyl, n-dodecyl, n-butyl; ii) (O)$_2$S(O$^-$)—, M$^+$ with M$^+$ as defined previously; iii) R$^o$—C(X)—X'—, R$^o$—X'—C(X)—, R°—X'—C(X)—X"— with R°, X, X' and X" as defined previously, preferentially R° represents a group $(C_1-C_8)$alkyl;

cycloalkyl; especially cyclohexyl;

Z represents a group chosen from hydroxyl and $NR'_{28}R'_{29}$ with $R'_{28}$ and $R'_{29}$, which may be identical or different, representing the same atoms or groups as $R_{28}$ and $R_{29}$ as defined previously;

it being understood that:
the chromophore (Xa) or (XIa) comprises at least one sulfonate radical $(O)_2S(O^-)$—, $M^+$ or a carboxylate radical —$C(O)O^-$, $M^+$; preferentially sodium sulfonate;

the chromophore (Xa) or (XIa) is linked to the rest of the molecule of formula (I) via one of the benzo groups G, or H of anthraquinone, in which case one of the substituents $R_{22}$ to $R_{27}$, Z or Z' is absent and the carbon atom of one of said benzo groups G, or H where said substituent is absent, is linked to the rest of the molecule.

As examples of chromophores of formula (Xa) derived from dyes, mention may be made of: Acid Blue 25, Acid Blue 43, Acid Blue 62, Acid Blue 78, Acid Blue 129, Acid Blue 138, Acid Blue 140, Acid Blue 251, Acid Green 25, Acid Green 41, Acid Violet 42, Acid Violet 43, Mordant Red 3;

and as examples of chromophores of formula (XIa) derived from dyes, mention may be made of: Acid Black 48;

d) Nitro Chromophores of Formula (XIIa) or (XIIIa):

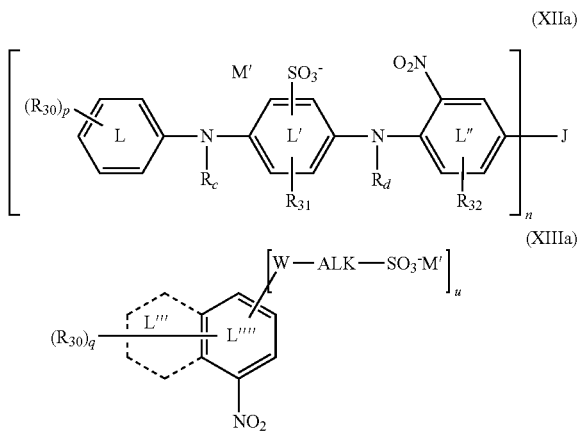

in which formulae (XIIa) and (XIIIa):

$R_{30}$, $R_{31}$ and $R_{32}$, which may be identical or different, represent a hydrogen or halogen atom, or a group chosen from:
$(C_1-C_8)$alkyl;
$(C_1-C_8)$alkoxy optionally substituted with one or more hydroxyl groups, $(C_1-C_8)$alkylthio optionally substituted with one or more hydroxyl groups;
hydroxyl, mercapto;
nitro, nitroso;
polyhalo$(C_1-C_8)$alkyl;
R°—C(X)—X'—, R°—X'—C(X)—, R°—X'—C(X)—X"— with R°; X, X' and X" as defined previously;
$(O)_2S(O^-)$—, $M^+$ with $M^+$ as defined previously;
$(O)CO^-$—, $M^+$ with $M^+$ as defined previously;
(di)$(C_1-C_8)$(alkyl)amino;
(di)(hydroxy$(C_1-C_8)$alkyl)amino;
heterocycloalkyl such as piperidino, piperazino or morpholino;

in particular, $R_{30}$, $R_{31}$ and $R_{32}$ represent a hydrogen atom;

$R_c$ and $R_d$, which may be identical or different, represent a hydrogen atom or an alkyl group;

W is as defined previously; W particularly represents a group —NH—;

ALK represents a linear or branched divalent $C_1-C_8$ alkylene group; in particular, ALK represents a group —$CH_2$—$CH_2$—;

n is 1 or 2;

p represents an integer between 1 and 5 inclusive;

q represents an integer between 1 and 4 inclusive;

u is 0 or 1;

when n is 1, J represents a nitro or nitroso group; particularly nitro;

when n is 2, J represents an oxygen or sulfur atom, or a divalent radical —$S(O)_m$— with m representing an integer 1 or 2; preferably J represents a radical —$SO_2$—;

M' represents a hydrogen atom or an organic or mineral cationic counterion;

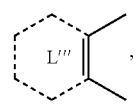

which may be present or absent, represents a benzo group optionally substituted with one or more groups $R_{30}$ as defined previously;

it being understood that:
the chromophore (XIIa) or (XIIIa) comprises at least one sulfonate radical $(O)_2S(O^-)$—, $M^+$ or a carboxylate radical —$C(O)O^-$, $M^+$; preferentially sodium sulfonate;

the chromophore (XIIa) or (XIIIa) is linked to the rest of the molecule of formula (I) via one of the rings L, L', L", L''' or L'''', in which case one of the substituents is absent and the carbon atom of one of the rings where said substituent is absent is linked to the rest of the molecule.

As examples of chromophores of formula (XIIa) derived from dyes, mention may be made of: Acid Brown 13; Acid Orange 3; as examples of chromophores of formula (XIIIa) derived from dyes, mention may be made of: Acid Yellow 1, sodium salt of 2,4-dinitro-1-naphthol-7-sulfonic acid, 2-piperidino 5-nitrobenzenesulfonic acid, 2-(4'-N,N(2"-hydroxyethyl)amino-2'-nitro)anilineethanesulfonic acid, 4-β-hydroxyethylamino-3-nitrobenzenesulfonic acid;

e) The Triarylmethane Chromophores of Formula (XIVa):

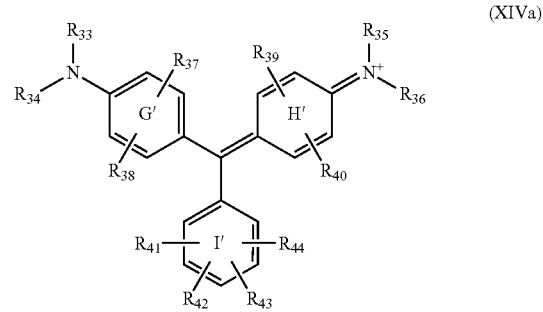

in which formula (XIVa):
  $R_{33}$, $R_{34}$, $R_{35}$ and $R_{36}$, which may be identical or different, represent a hydrogen atom or a group chosen from ($C_1$-$C_8$)alkyl, optionally substituted aryl and optionally substituted aryl($C_1$-$C_8$)alkyl; particularly a group ($C_1$-$C_8$)alkyl and benzyl optionally substituted with a group $(O)_mS(O^-)$—, $M^+$ with $M^+$ and m as defined previously;
  $R_{37}$, $R_{38}$, $R_{39}$, $R_{40}$, $R_{41}$, $R_{42}$, $R_{43}$ and $R_{44}$, which may be identical or different, represent a hydrogen atom or a group chosen from:
    ($C_1$-$C_8$)alkyl;
    ($C_1$-$C_8$)alkoxy, ($C_1$-$C_8$)alkylthio;
    (di)($C_1$-$C_8$)(alkyl)amino;
    hydroxyl, mercapto;
    nitro, nitroso;
    $R^o$—C(X)—X'—, $R^o$—X'—C(X)—, $R^o$—X'—C(X)—X"— with $R^o$ representing a hydrogen atom or a group ($C_1$-$C_8$)alkyl or aryl; X, X' and X", which may be identical or different, representing an oxygen or sulfur atom, or NR with R representing a hydrogen atom or a group ($C_1$-$C_8$)alkyl;
    $(O)_2S(O^-)$—, $M^+$ with $M^+$ representing a hydrogen atom or an organic or mineral cationic counterion;
    $(O)CO^-$—, $M^+$ with $M^+$ as defined previously;
  or alternatively two contiguous groups $R_{41}$ with $R_{42}$ or $R_{42}$ with $R_{43}$ or $R_{43}$ with $R_{44}$ together form a fused benzo group: I'; with I' optionally substituted with one or more groups chosen from i) nitro; ii) nitroso; iii) $(O)_2S(O^-)$—, $M^+$; iv) hydroxyl; v) mercapto; vi) (di)($C_1$-$C_8$)(alkyl)amino; vii) $R^o$—C(X)—X'—; viii) $R^o$—X'—C(X)—; ix) $R^o$—X'—C(X)—X"—; with $M^+$, $R^o$, X, X', X" as defined previously;
  particularly, $R_{37}$ to $R_{40}$ represent a hydrogen atom, and $R_{41}$ to $R_{44}$, which may be identical or different, represent a hydroxyl group or $(O)_2S(O^-)$—, $M^+$; and when $R_{43}$ with $R_{44}$ together form a benzo group, it is preferentially substituted with a group $(O)_2S(O^-)$—;
it being understood that:
  the chromophore (XIVa) comprises at least one of the rings G', H', or I' containing at least one sulfonate radical $(O)_2S(O^-)$— or a carboxylate radical —C(O)O—; preferentially sulfonate;
  the chromophore (XIVa) is linked to the rest of the molecule of formula (Ia) via one of the rings G', H' or I', in which case one of the substituents is absent and the carbon atom of one of the rings where said substituent is absent is linked to the rest of the molecule.
As examples of chromophores of formula (XIVa) derived from dyes, mention may be made of: Acid Blue 1; Acid Blue 3; Acid Blue 7, Acid Blue 9; Acid Violet 49; Acid Green 50.
f) The Anionic Xanthene-Based Chromophores of Formula (XVa):

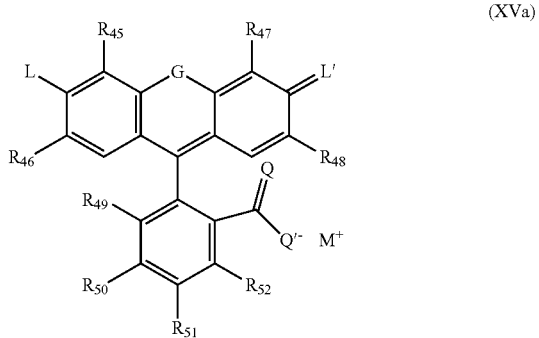

(XVa)

in which formula (XVa):
  $R_{45}$, $R_{46}$, $R_{47}$ and $R_{48}$, which may be identical or different, represent a hydrogen atom or a halogen atom;
  $R_{49}$, $R_{50}$, $R_{51}$ and $R_{52}$, which may be identical or different, represent a hydrogen or halogen atom or a group chosen from:
    ($C_1$-$C_8$)alkyl;
    ($C_1$-$C_8$)alkoxy, ($C_1$-$C_8$)alkylthio;
    hydroxyl, mercapto;
    nitro, nitroso;
    $(O)_2S(O^-)$—, $M^+$ with $M^+$ representing a hydrogen atom or an organic or mineral cationic counterion;
    $(O)CO^-$—, $M^+$ with $M^+$ as defined previously;
  particularly $R_{53}$ $R_{54}$, $R_{55}$ and $R_{48}$ represent a hydrogen or halogen atom;
  G represents an oxygen or sulfur atom or a group $NR_e$ with $R_e$ as defined previously; particularly G represents an oxygen atom;
  L represents an alkoxide $O^-$, $M^+$; a thioalkoxide $S^-$, $M^+$ or a group $NR_f$, with $R_f$ representing a hydrogen atom or a group ($C_1$-$C_8$)alkyl, and $M^+$ as defined previously; $M^+$ is particularly sodium or potassium;
  L' represents an oxygen or sulfur atom or an ammonium group: $N^+R_fR_g$, with $R_f$ and $R_g$, which may be identical or different, representing a hydrogen atom, a group ($C_1$-$C_8$)alkyl, optionally substituted aryl; L' represents particularly an oxygen atom or a phenylamino group optionally substituted with one or more groups ($C_1$-$C_8$) alkyl or $(O)_mS(O^-)$—, $M^+$ with m and $M^+$ as defined previously;
  Q and Q', which may be identical or different, represent an oxygen or sulfur atom; particularly Q and Q' represent an oxygen atom;
  $M^+$ is as defined previously;
it being understood that the chromophore (XVa) is linked to the rest of the molecule of formula (Ia) via one of the rings, in which case one of the substituents $R_{45}$, $R_{46}$, $R_{47}$, $R_{48}$, $R_{49}$, $R_{50}$, $R_{51}$ or $R_{52}$ is absent and the carbon atom of one of the rings where said substituent is absent is linked to the rest of the molecule.
As examples of chromophores of formula (XVa) derived from dyes, mention may be made of: Acid Yellow 73; Acid Red 51; Acid Red 87; Acid Red 92; Acid Red 95; Acid Violet 9;
g) The Anionic Indole-Based Chromophores of Formula (XVIa):

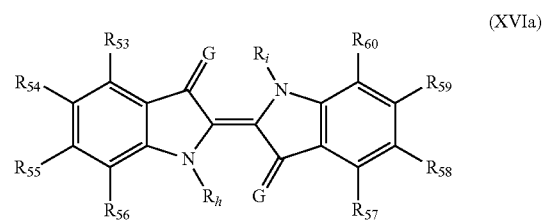

(XVIa)

in which formula (XVIa):
  $R_{53}$, $R_{54}$, $R_{55}$, $R_{56}$, $R_{57}$, $R_{58}$, $R_{59}$ and $R_{60}$, which may be identical or different, represent a hydrogen atom or a group chosen from:
    ($C_1$-$C_8$)alkyl;
    ($C_1$-$C_8$)alkoxy, ($C_1$-$C_8$)alkylthio;
    hydroxyl, mercapto;
    nitro, nitroso;

R°—C(X)—X'—, R°—X'—C(X)—, R°—X'—C(X)—X"— with R° representing a hydrogen atom or a group ($C_1$-$C_8$)alkyl or aryl; X, X' and X", which may be identical or different, representing an oxygen or sulfur atom, or NR with R representing a hydrogen atom or a group ($C_1$-$C_8$)alkyl;

$(O)_2S(O^-)$—, $M^+$ with $M^+$ representing a hydrogen atom or an organic or mineral cationic counterion;

$(O)C(O^-)$—, $M^+$ with $M^+$ as defined previously;

G represents an oxygen or sulfur atom or a group $NR_e$ with $R_e$ as defined previously; particularly G represents an oxygen atom;

$R_i$ and $R_h$, which are identical or different, represent a hydrogen atom or a ($C_1$-$C_8$)alkyl group;

it being understood that:
  the chromophore (XVIa) comprises at least one sulfonate radical $(O)_2S(O^-)$—, $M^+$ or a carboxylate radical —$C(O)O^-$, $M^+$; preferentially sodium sulfonate;
  the chromophore (XVIa) is linked to the rest of the molecule of formula (Ia) via one of the rings, in which case one of the substituents $R_{53}$, $R_{54}$, $R_{55}$, $R_{56}$, $R_{57}$, $R_{58}$, $R_{59}$ or $R_{60}$ is absent and the carbon atom of one of the rings where said substituent is absent is linked to the rest of the molecule.

As examples of dyes of formula (XVIa), mention may be made of: Acid Blue 74.

h) The Anionic Quinoline-Based Chromophores of Formula (XVIIa):

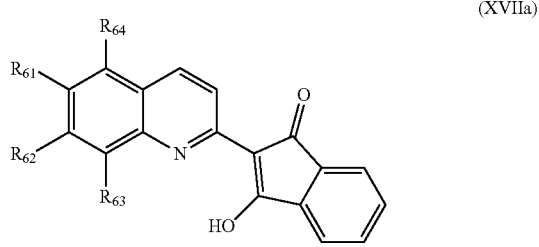

(XVIIa)

in which formula (XVIIa):
  $R_{61}$ represents a hydrogen or halogen atom or a group ($C_1$-$C_8$)alkyl;
  $R_{62}$, $R_{63}$ and $R_{64}$, which may be identical or different, represent a hydrogen atom or a group $(O)_2S(O^-)$—, $M^+$ with $M^+$ representing a hydrogen atom or an organic or mineral cationic counterion;
  or alternatively $R_{61}$ with $R_{62}$, or $R_{61}$ with $R_{64}$, together form a benzo group optionally substituted with one or more groups $(O)_2S(O^-)$—, $M^+$ with $M^+$ representing a hydrogen atom or an organic or mineral cationic counterion;

it being understood that:
  the chromophore (XVIIa) comprises at least one sulfonate radical $(O)_2S(O^-)$—, $M^+$ preferentially sodium sulfonate;
  the chromophore (XVIIa) is linked to the rest of the molecule of formula (Ia) via one of the rings, in which case one of the substituents $R_{61}$, $R_{62}$, $R_{63}$ or $R_{64}$ is absent and the carbon atom of one of the rings where said substituent is absent is linked to the rest of the molecule.

As examples of chromophores of formula (XVIIa) derived from dyes, mention may be made of: Acid Yellow 2, Acid Yellow 3 and Acid Yellow 5.

Most of these dyes are described in particular in the Color Index published by The Society of Dyers and Colorists, P.O. Box 244, Perkin House, 82 Grattan Road, Bradford, Yorkshire, BD1 2JBN England.

The anionic dyes that are more particularly preferred are the dyes designated in the Color Index under the code C.I. 58005 (monosodium salt of 1,2-dihydroxy-9,10-anthraquinone-3-sulfonic acid), C.I. 60730 (monosodium salt of 2-[(9,10-dihydro-4-hydroxy-9,10-dioxo-1-anthracenyl)amino]-5-methylbenzenesulfonic acid), C.I. 15510 (monosodium salt of 4-[(2-hydroxy-1-naphthyl)azo]benzenesulfonic acid), C.I. 15985 (disodium salt of 6-hydroxy-5-[(4-sulfophenyl)azo]-2-naphthalenesulfonic acid), C.I. 17200 (disodium salt of 5-amino-4-hydroxy-3-(phenylazo)-2,7-naphthalenedisulfonic acid), C.I. 20470 (disodium salt of 1-amino-2-(4'-nitrophenylazo)-7-phenylazo-8-hydroxy-3,6-naphthalenedisulfonic acid), C.I. 42090 (disodium salt of N-ethyl-N-[4-[[4-[ethyl[3-sulfophenyl)methyl]amino]phenyl](2-sulfophenyl)methylene]-2,5-cyclohexadien-1-ylidene]-3-sulfobenzenemethanaminium hydroxide, inner salt), C.I. 61570 (disodium salt of 2,2'-[(9,10-dihydro-9,10-dioxo-1,4-anthracenediyl)diimino]bis[5-methyl]benzenesulfonic acid).

It is also possible to use the chromophores corresponding to the mesomeric or tautomeric forms of structures (IIIa) to (XVIIa).

I.2. Fluorescent Chromophores $A_1$ and $A'_1$:

The radical $A_1$ or the radicals $A_1$ and $A'_1$ of formula (I) may contain one or more identical or different fluorescent coloured chromophores.

According to one particular embodiment of the invention, $A_1$ and/or $A'_1$ are fluorescent chromophores.

The term "fluorescent chromophore" means a chromophore that is coloured and fluorescent, said term therefore does not mean "optical brightener" chromophores, or any other colourless fluorescent compounds, i.e. which do not absorb in the visible spectrum (see *Ullmann's Encyclopedia of Industrial Chemistry*, in the chapters "Fluorescent Dyes" and "Optical Brighteners", 2005, Wiley-VCH Verlag GmbH & Co. KGaA, Weinheim 10.1002/143560007.a18_153; and 2005, Wiley-VCH Verlag GmbH & Co. KGaA, Weinheim 10.1002/143560007.a 11_279).

As fluorescent chromophores that are useful in the present invention, mention may be made of radicals derived from the following dyes: acridines, acridones, azlactones, benzanthrones, benzimidazoles, benzimidazolones, benzindoles, benzoxazoles, benzopyrans, benzothiazoles, coumarins, difluoro{2-[(2H-pyrrol-2-ylidene-kN)methyl]-1H-pyrrolato-kN}borons (BODIPY®), dipyrinones, diketopyrrolopyrroles, fluorindines, (poly)methines (especially cyanins and styryls/hemicyanins), naphthalimides, naphthanilides, naphthylamine (such as dansyls), naphtholactams, oxadiazoles, oxazines, perilones, perinones, perylenes, polyenes/carotenoids, squaranes, stilbenes, xanthenes, thioxanthenes, and thiazines.

Mention may also be made of fluorescent chromophores derived from the fluorescent dyes described in documents EP 1 133 975, WO 03/029 359, EP 860 636, WO 95/01772, WO 95/15144, EP 714 954 and those listed in the encyclopaedia *The chemistry of synthetic dye* by K. Venkataraman, 1952, Academic Press, vol. 1 to 7, in *Kirk Othmer*'s encyclopaedia *Chemical Technology*, in the chapter "Dyes and Dye Intermediates", 1993, Wiley and Sons, and in various chapters of *Ullmann's Encyclopedia of Industrial Chemistry* 7th edition, Wiley and Sons, especially in *Ullmann's Encyclopedia of Industrial Chemistry* in the chapter "Fluorescent Dyes", 2005, Wiley-VCH Verlag GmbH & Co. KGaA, Weinheim 10.1002/143560007.a11_279; in *The Handbook—A Guide to Fluorescent Probes and Labeling Technologies*, 10th Ed Molecular Probes/Invitrogen—Oregon 2005 circulated on the Internet or in the preceding printed editions.

Preferably, the chromophores are chosen from those derived from dyes of coumarin type, of (poly)methine type, especially cyanins and styryl/hemicyanin dyes, and of naphthalimide type. More particularly, the fluorescent chromophores are cationic.

According to one variant, the radical $A_1$ and/or $A'_1$ of formula (I) contains at least one cationic radical borne by, or included in, at least one of the chromophores.

Preferably, the cationic radical is a quaternary ammonium; more preferentially, the cationic charge is endocyclic.

These cationic radicals are, for example, a cationic radical:
  bearing an exocyclic (di/tri)($C_1$-$C_8$)alkylammonium charge, or
  bearing an endocyclic charge, such as the following cationic heteroaryl groups: acridinium, benzimidazolium, benzobistriazolium, benzopyrazolium, benzopyridazinium, benzoquinolium, benzothiazolium, benzotriazolium, benzoxazolium, bipyridinium, bistetrazolium, dihydrothiazolium, imidazopyridinium, imidazolium, indolium, isoquinolium, naphthoimidazolium, naphthoxazolium, naphthopyrazolium, oxadiazolium, oxazolium, oxazolopyridinium, oxonium, phenazinium, phenoxazolium, pyrazinium, pyrazolium, pyrazoyltriazolium, pyridinium, pyridinoimidazolium, pyrrolium, pyrylium, quinolium, tetrazolium, thiadiazolium, thiazolium, thiazolopyridinium, thiazoylimidazolium, thiopyrylium, triazolium or xanthylium.

According to one preferred variant of the invention, the fluorescent chromophore $A_1$ and/or $A'_1$ is cationic and comprises at least one quaternary ammonium radical such as the polymethines of formulae (XVIIIa) and (XIXa) below:

  (XVIIIa) or

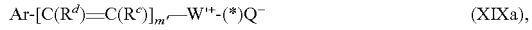  (XIXa), formula (XVIIIa) or (XIXa) with:
$W^+$ representing a cationic heterocyclic or heteroaryl group, particularly comprising a quaternary ammonium optionally substituted with one or more groups ($C_1$-$C_8$) alkyl optionally substituted especially with one or more hydroxyl groups;
$W'^+$ representing a divalent heterocyclic or heteroaryl radical as defined for $W^+$;
Ar representing an aryl group such as phenyl or naphthyl, optionally substituted preferentially with i) one or more halogen atoms such as chlorine or fluorine; ii) one or more groups ($C_1$-$C_8$)alkyl, preferably of $C_1$-$C_4$ such as methyl; iii) one or more hydroxyl groups; iv) one or more ($C_1$-$C_8$)alkoxy groups such as methoxy; v) one or more hydroxy($C_1$-$C_8$)alkyl groups such as hydroxyethyl, vi) one or more amino or (di)($C_1$-$C_8$)alkylamino groups, preferably with the $C_1$-$C_4$ alkyl part optionally substituted with one or more hydroxyl groups, such as (di)hydroxyethylamino, vii) with one or more acylamino groups; viii) one or more heterocycloalkyl groups such as piperazinyl, piperidyl or 5- or 6-membered heteroaryl such as pyrrolidinyl, pyridyl and imidazolinyl;
Ar' is a divalent aryl radical as defined for Ar;

m' represents an integer between 1 and 4 inclusive, particularly m is 1 or 2; more preferentially 1;
$R^c$ and $R^d$, which may be identical or different, represent a hydrogen atom or an optionally substituted group ($C_1$-$C_8$)alkyl, preferentially of $C_1$-$C_4$, or alternatively $R^c$ contiguous with W or W' and/or $R^d$ contiguous with Ar or Ar' form, with the atoms that bear them, a (hetero)cycloalkyl, particularly $R^c$ is contiguous with $W^+$ or $W'^+$ and forms a (hetero)cycloalkyl such as cyclohexyl;
$Q^-$ is an organic or mineral anionic counterion as defined previously;
(*) represents the part of the chromophore linked to the rest of formula (I).

Preferably, $W^+$ or $W'^+$ is an imidazolium, pyridinium, benzimidazolium, pyrazolium, benzothiazolium or quinolinium radical optionally substituted with one or more identical or different $C_1$-$C_4$ alkyl radicals.

According to one particularly preferred embodiment of the invention, $A_1$ and/or $A'_1$ represent the chromophore (XVIIIa) or (XIXa) as defined previously with m'=1, Ar representing a phenyl group substituted para to the styryl group —C($R^d$)=C($R_c$)— with a group (di)(hydroxy)($C_1$-$C_6$)(alkyl)amino such as dihydroxy($C_1$-$C_4$)alkylamino, and $W'^+$ representing an imidazolium or pyridinium group, preferentially ortho- or para-pyridinium.

According to another preferred variant of the invention, the fluorescent chromophore $A_1$ and/or $A'_1$ is cationic and comprises at least one quaternary ammonium radical such as a naphthalimidyl bearing an exocyclic cationic charge of formula (XXa) or (XXIa):

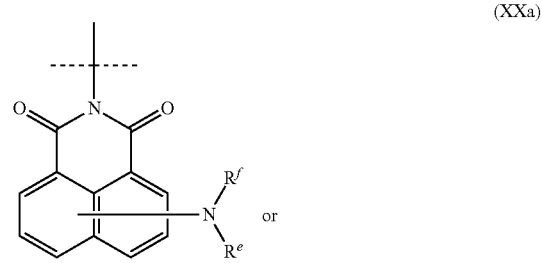

(XXa)

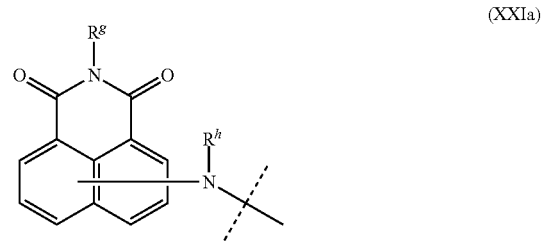

(XXIa)

with ┼ representing the bond with the group $X_1$ or $X'_1$, $C_{sat}$ or $C'_{sat}$
in which formulae (XXa) and (XXIa) $R^e$, $R^f$, $R^g$ and $R^h$, which may be identical or different, represent a hydrogen atom or a $C_1$-$C_6$ alkyl group which is optionally substituted, preferentially with a di($C_1$-$C_6$)alkylamino or tri($C_1$-$C_6$)alkylammonium group such as trimethylammonium.

1.2. $X_1$, $X'_1$;

In accordance with one particular embodiment of the invention, in the abovementioned formula (Ia), when p and/or p' is equal to 1, the radical $X_1$ and/or $X'_1$ represents the following sequence: -(T)$_t$-(Z)$_z$-(T')$_{t'}$- said sequence being linked in the formulae (I), as follows: (A$_1$ or A'$_1$)-(T)$_t$-(Z)$_z$-(T')$_{t'}$-R$_{a1}$;

in which sequence:
T and T', which may be identical or different, represent one or more radicals or combinations thereof chosen from: —S(O)$_2$—; —O—; —S—; —N(R)—; —N$^+$(R)(R$^o$)—, Q$^-$; —C(O)—; with R and R$^o$, which may be identical or different, representing a hydrogen atom, a C$_1$-C$_4$ alkyl, C$_1$-C$_4$ hydroxyalkyl or aryl(C$_1$-C$_4$)alkyl radical and Q$^-$ representing an organic or mineral anionic counterion; and a cationic or non-cationic, preferentially monocyclic heterocycloalkyl or heteroaryl radical, preferentially containing two heteroatoms (more preferentially two nitrogen atoms) and preferentially being 5- to 7-membered, more preferentially imidazolium, piperazinyl or piperidyl;

in particular, T and T' represent one or more radicals or combinations thereof chosen from —O—, —N(R)—, —C(O)—, with R chosen from a hydrogen atom and a radical (C$_1$-C$_4$)alkyl; preferentially chosen from —O—, —N(R), —N(R)—C(O)— and —C(O)—N(R)—;

the indices t and t', which may be identical or different, are equal to 0 or 1;

Z represents:
—(CR$_1$R$_2$)$_m$— with m being an integer between 1 and 8 inclusive and R$_1$ and R$_2$, which may be identical or different, represent a hydrogen atom or a group (C$_1$-C$_4$)alkyl, (C$_1$-C$_4$)alkoxy, hydroxyl, cyano, carboxyl or (di)(C$_1$-C$_4$)(alkyl)amino, said alkyl radicals possibly forming, with the nitrogen atom that bears them, a 5- to 7-membered heterocycle, optionally comprising another nitrogen or non-nitrogen heteroatom, such as morpholino or piperidino; R$_1$ and R$_2$ particularly represent a hydrogen atom;

—(CH$_2$CH$_2$O)$_q$— or —(OCH$_2$CH$_2$)$_q$— in which q is an integer between 1 and 15 inclusive, preferentially between 1 and 6, or a divalent arylene, (C$_1$-C$_4$)alkylaryl or aryl(C$_1$-C$_4$) alkyl radical such as benzyl whose aryl radical is preferably C$_6$, being optionally substituted with at least one group SO$_3$M with M representing a hydrogen atom, an alkali metal or an ammonium group, the ammonium being substituted with one or more identical or different, linear or branched (C$_1$-C$_4$)alkyl radicals, optionally substituted with one or more hydroxyl groups;

z is 0 or 1.

According to one preferred embodiment of the invention, Z represents a divalent group chosen from: —(CR$_1$R$_2$)$_m$— with m equal to 3 or 4.

According to another particular mode of the invention, X$_1$ and/or X'$_1$ represents a divalent group or a combination of divalent groups chosen from —O—; —N(R)—; —C(O)— with R chosen from a hydrogen atom and a C$_1$-C$_4$ alkyl radical. In particular, X$_1$ and/or X'$_1$ is chosen from —O—, —N(R)—C(O)— and —C(O)—N(R)—.

According to one particular embodiment of the invention, the ingredient(s) i) are chosen from direct dyes (I) bearing an alkenyl or alkynyl group such as those of formula (I'a):

(I'a)

in which formula (I'a):
R$_{a1}$ represents a C$_4$-C$_{10}$ alkenyl group, optionally substituted with an amino group and comprising at the end of said alkenyl group a double bond of the type —(CH$_2$)$_r$—CH=CH$_2$ with r being an integer inclusively between 2 and 10 and particularly r being equal to 2 or 3; preferentially, R$_{a1}$ represents: —CH$_2$—CH$_2$—CH=CH$_2$;

t and t', which may be identical or different, are equal to 0 or 1;

Z represents the divalent group —(CH$_2$)$_m$— with m being an integer inclusively between 2 and 4; preferentially, m is equal to 3 or 4;

T and T', which may be identical or different, represent divalent radicals chosen from —O—, —N(R), —N(R)—C(O)— and —C(O)—N(R)—;

A$_1$ represents:
a) either a cationic chromophore chosen from the following formulae:

(IIIa)

(IVa)

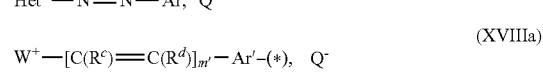

(XVIIIa)

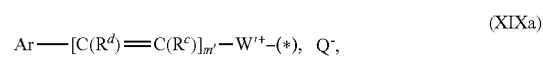

(XIXa)

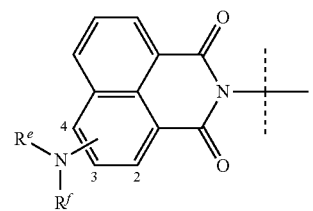

(XXa)

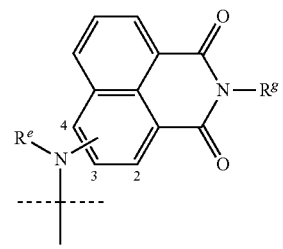

(XXIa)

with formulae (IIIa), (IVa), (XVIIa) to (XXIa) as defined previously; preferentially, R$^a$ represents a hydrogen atom, R$^b$ represents a hydrogen atom or an alkyl group, m' is 1 and R$^c$ and R$^d$ represent a hydrogen atom or R$^c$ is contiguous with W$^+$ or W'$^+$ forms a (hetero)cycloalkyl such as cyclohexyl; the amino groups of formulae (XXa) and (XXIa) are linked to the carbon atom of the phenyl groups in position 2, 3 or 4, preferably 4, and R$^e$, R$^f$, R$^g$ and R$^h$, which may be identical or different, represent a hydrogen atom or a C$_1$-C$_6$ alkyl group optionally substituted with a di(C$_1$-C$_6$)alkylamino or tri(C$_1$-C$_6$)alkylammonium group such as trimethylammonium;

b) or an anionic chromophore chosen from the following formulae:

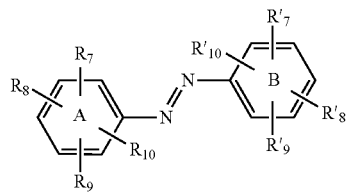
(VIa)

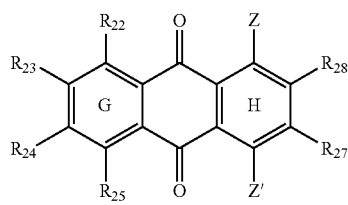
(Xa)

with formulae (VIa) and (Xa) as defined previously;

more particularly T is in the para position on Ar or Ar' relative to the hydrazono part of (III) or (III'), or the polymethine part —[C(R$^c$)=C(R$^d$)]$_{m'}$— of (IVa), (XVIIIa) or (XIXa), is in the para position on ring A or B relative to the azo part of (VIa), or alternatively is in the place of Z or Z' on the chromophore (Xa).

According to one particularly advantageous mode of the invention, the radical Het$^+$, W$^+$, or W$^+$ is a group chosen from imidazolium, pyridinium, benzopyridinium, benzimidazolium, quinolinium, indolinium and pyrazolium, optionally substituted preferentially with one or more identical or different C$_1$-C$_4$ alkyl radicals.

More particularly, Het$^+$, W$^+$ or W$^+$ is chosen from pyridinium, imidazolium and indolinium groups optionally substituted with one or more identical or different (C$_1$-C$_4$)alkyl radicals, such as methyl.

According to a particularly advantageous mode of the invention, Ar is an optionally substituted phenyl group, Ar' is an optionally substituted phenylene group and Ar' is an optionally substituted phenyl or naphthyl bearing an exocyclic tri(C$_1$-C$_8$)alkylammonium cationic charge such as trimethylammonium.

More preferably, the dye of formula (I) or (I'a) is a dye chosen from the compounds of formulae (1a) to (1n) below:

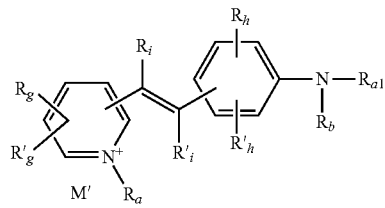
(1a)

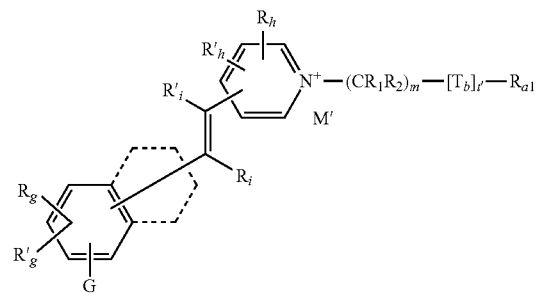
(1b)

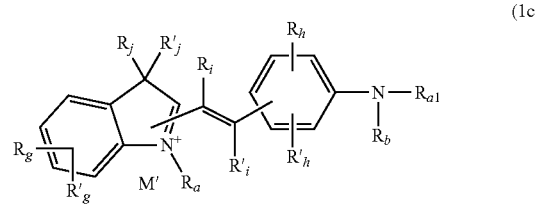
(1c)

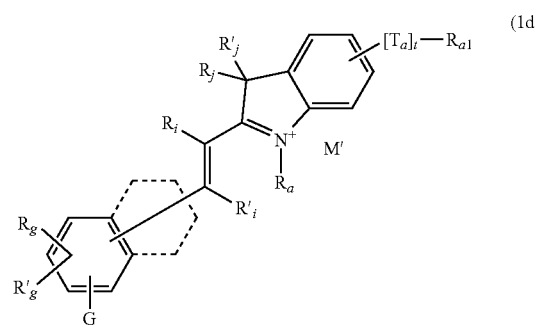
(1d)

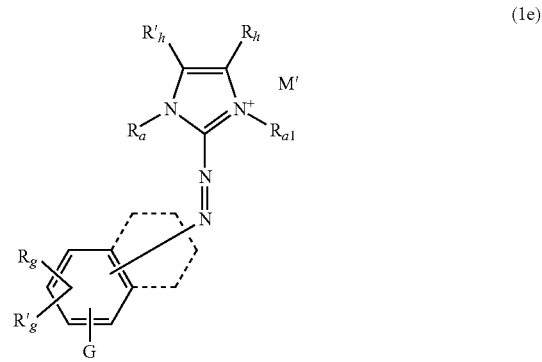
(1e)

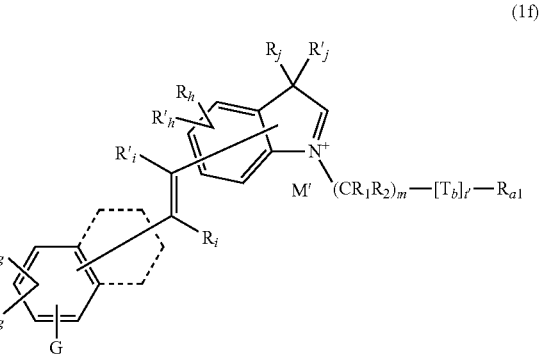
(1f)

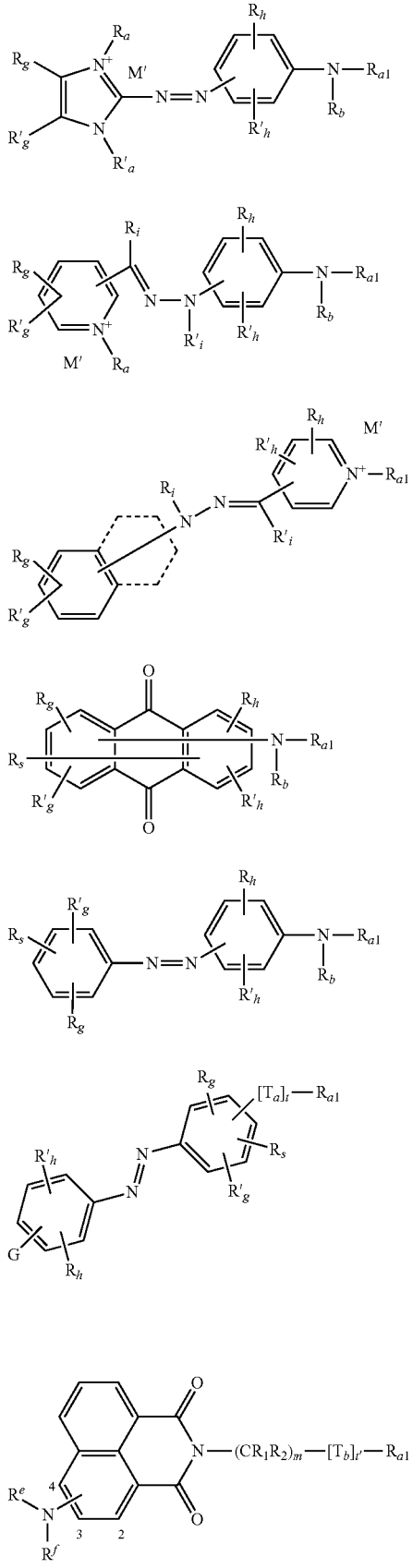

and also the organic or mineral acid or base salts, optical isomers, geometrical isomers and tautomers thereof and solvates thereof such as hydrates;

in which formulae (1a) to (1n):

$R_{a1}$ is as defined previously, in particular a $C_4$-$C_{10}$ alkenyl group, optionally substituted with an amino group and comprising at the end of said alkenyl group a double bond of the type —$(CH_2)_r$—CH=$CH_2$ with r being an integer inclusively between 2 and 10 and particularly r being equal to 2 or 3; preferentially, $R_{a1}$ represents —$CH_2$—$CH_2$—CH=$CH_2$;

G represents a group —$NR_cR_d$ or $(C_1$-$C_6)$alkoxy; according to a preferred mode, G represents a group —$NR_cR_d$ preferably para to the styryl, azo or hydrazono group; according to another preferred mode, G represents a $(C_1$-$C_6)$alkoxy group;

$R_a$ and $R'_a$, which may be identical or different, represent an optionally substituted $(C_1$-$C_6)$alkyl group; preferentially, $R_a$ represents a $(C_1$-$C_3)$alkyl group optionally substituted with a hydroxyl group, preferentially unsubstituted, such as methyl;

$R_b$ represents a hydrogen atom or an optionally substituted $C_1$-$C_6$ alkyl group; preferentially unsubstituted, such as methyl;

$R_c$ and $R_d$, which may be identical or different, represent a hydrogen atom, an aryl$(C_1$-$C_4)$alkyl or $(C_1$-$C_6)$alkoxy group or a $(C_1$-$C_6)$alkyl group which is optionally substituted; $R_c$ and $R_d$ preferentially represent a hydrogen atom or a group $(C_1$-$C_3)$alkyl optionally substituted with i) a hydroxyl group, ii) amino, iii) (di)$(C_1$-$C_3)$ alkylamino, or iv) quaternary ammonium (R")(R''') (R'''')$N^+$—, $Q^-$ with $Q^-$ being an organic or mineral anionic counterion;

or alternatively two adjacent radicals $R_c$ and $R_d$, borne by the same nitrogen atom, together form a heterocyclic or heteroaryl group; preferentially, the heterocycle or heteroaryl is monocyclic and 5- to 7-membered; more preferentially, the groups are chosen from imidazolyl and pyrrolidinyl;

particularly, $R_c$ and $R_d$ represent identical groups; preferentially $R_c$ and $R_d$ represent a $(C_1$-$C_3)$alkyl optionally substituted with a hydroxyl group, such as methyl, hydroxyethyl and 2-hydroxypropyl;

$R_g$, $R'_g$, $R_h$ and $R'_h$, which may be identical or different, represent a hydrogen atom, a halogen atom, a di$(C_1$-$C_4)$(alkyl)amino, cyano, carboxyl, hydroxyl or trifluoromethyl group, an acylamino, $(C_1$-$C_4)$alkoxy, (poly)hydroxy$(C_2$-$C_6)$alkoxy, $(C_1$-$C_4)$alkylcarbonyloxy, $(C_1$-$C_4)$alkoxycarbonyl, $(C_1$-$C_4)$alkylcarbonylamino, acylamino, carbamoyl or $(C_1$-$C_4)$alkylsulfonylamino radical, an aminosulfonyl radical, or a $(C_1$-$C_{16})$alkyl radical optionally substituted with a group chosen from $(C_1$-$C_6)$alkoxy, hydroxyl, cyano, carboxyl and di$(C_1$-$C_4)$(alkyl)amino, or alternatively the two alkyl radicals borne by the nitrogen atom of the amino group form a 5- to 7-membered heterocycle optionally comprising another nitrogen or non-nitrogen heteroatom; preferentially, $R_g$, $R'_g$, $R_h$ and $R'_h$ represent a hydrogen or halogen atom or a $(C_1\text{-}C_3)$alkyl or $(C_1\text{-}C_3)$alkoxy group; more preferentially, $R_g$, $R'_g$, $R_h$ and $R'_h$ represent a hydrogen atom;

or alternatively two groups $R_g$ and $R'_g$; $R_h$ and $R'_h$ borne by two adjacent carbon atoms together form a benzo or indeno ring, a fused heterocycloalkyl or fused heteroaryl group; the benzo, indeno, heterocycloalkyl or heteroaryl ring being optionally substituted with a halogen atom, a (di)$(C_1\text{-}C_4)$(alkyl)amino, nitro, cyano, carboxyl, hydroxyl or trifluoromethyl group, an acylamino, $(C_1\text{-}C_4)$alkoxy, (poly)hydroxy$(C_2\text{-}C_4)$alkoxy, $(C_1\text{-}C_4)$alkylcarbonyloxy, $(C_1\text{-}C_4)$alkoxycarbonyl or $(C_1\text{-}C_4)$alkylcarbonylamino radical, an acylamino, carbamoyl or $(C_1\text{-}C_4)$alkylsulfonylamino radical, an aminosulfonyl radical, or a $(C_1\text{-}C_{16})$alkyl radical optionally substituted with: a group chosen from $(C_1\text{-}C_6)$alkoxy, hydroxyl, cyano, carboxyl and (di)$(C_1\text{-}C_4)$(alkyl)amino, or alternatively the two alkyl radicals borne by the nitrogen atom of the amino group form a 5- to 7-membered heterocycle optionally comprising another nitrogen or non-nitrogen heteroatom; preferentially, $R_g$ and $R'_g$ together form a benzo group;

or alternatively when G represents $-NR_cR_d$ two groups $R_c$ and $R'_g$; $R_d$ and $R'_g$; together form a saturated heteroaryl or heterocycle, optionally substituted with one or more groups $(C_1\text{-}C_6)$alkyl, preferentially a 5- to 7-membered heterocycle containing one or two heteroatoms chosen from nitrogen and oxygen; more preferentially the heterocycle is chosen from morpholinyl, piperazinyl, piperidyl and pyrrolidinyl groups;

$R_i$, $R_j$, $R'_j$ and $R'_i$, which may be identical or different, represent a hydrogen atom, or a group $C_1\text{-}C_4$ alkyl; more preferentially, $R_i$, $R_j$, $R'_j$ and $R'_i$ represent a hydrogen atom;

or alternatively $R_i$ with $R_g$, $R'_i$ with $R_h$ borne by two adjacent atoms, together form a (hetero)cycloalkyl group, particularly for (1a) and (1b), $R_i$ with $R_g$ or $R'_i$ with $R_h$ form a cycloalkyl such as cyclohexyl;

$R_s$ represents a sulfonate radical $(O)_2S(O^-)-$, $M^+$ or a carboxylate radical $-C(O)O^-$, $M^+$ with $M^+$ representing an organic or mineral cationic counterion; preferentially sulfonate such as sodium sulfonate;

the amino groups of the compounds (1m) and (1n) are linked to the carbon atoms of the phenyl group in position 2, 3 or 4, preferably 4;

$R^e$, $R^f$, $R^g$ and $R^h$, which may be identical or different, represent a hydrogen atom or a $C_1\text{-}C_6$ alkyl group which is optionally substituted, preferentially with a di$(C_1\text{-}C_6)$alkylamino or tri$(C_1\text{-}C_6)$alkylammonium group such as trimethylammonium;

$R_1$, $R_2$, $R_3$ and $R_4$, which may be identical or different, represent a hydrogen atom or a group $(C_1\text{-}C_4)$alkyl, $(C_1\text{-}C_{12})$alkoxy, hydroxyl, cyano, carboxyl or (di)$(C_1\text{-}C_4)$(alkyl)amino, said alkyl radicals possibly forming, with the nitrogen atom that bears them, a 5- to 7-membered heterocycle, optionally comprising another nitrogen or non-nitrogen heteroatom; preferentially, $R_1$, $R_2$, $R_3$ and $R_4$ are hydrogen atoms or an amino group; more preferably, $R_1$, $R_2$, $R_3$ and $R_4$ represent a hydrogen atom;

t and t', which may be identical or different, are equal to 0 or 1; preferentially, t' is 0;

$T_a$ and $T_b$, which may be identical or different, represent one or more radicals or combinations thereof chosen from $-S(O)_2-$, $-O-$, $-S-$, $-N(R)-$, $-N^+(R)$ $(R^o)-$ $M^-$, $-C(O)-$, with R, $R^o$, which may be identical or different, representing a hydrogen atom or a radical $(C_1\text{-}C_4)$alkyl, hydroxy$(C_1\text{-}C_4)$alkyl; or an aryl$(C_1\text{-}C_4)$alkyl, and M-represents an organic or mineral anionic counterion such as halide; preferentially represents a group chosen from a radical $-O-$, $-C(O)-$, $-N(R)-$ or a combination thereof with R representing a hydrogen atom or a $(C_1\text{-}C_4)$alkyl group such as methyl, more particularly a radical $-O-$ or $-N(R)-C(O)-$;

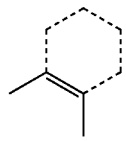

represents an aryl or heteroaryl group fused to the phenyl ring; or alternatively is absent from the phenyl ring; when the ring is present, the ring is preferentially a benzo; more preferentially, the ring is absent;

m and n, which may be identical or different, represent an integer between 0 and 10 inclusive with m+n representing an integer between 1 and 10, particularly between 1 and 6, more particularly m+n=1, 2 or 3;

M' representing an organic or mineral anionic counterion.

According to a preferred embodiment of the invention, the direct dyes are of formulae (1a), (1b), (1e), (1g), (1i), (1j), (1k) and (1m); more preferably (1b)

More particularly, the dyes according to the invention are chosen from the direct dyes of formulae (1'a), (1'b), (1'e), (1'g), (1'i), (1'j), (1'k) and (1'm) below:

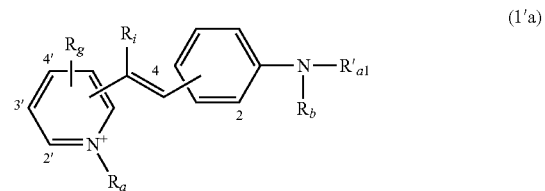

(1'a)

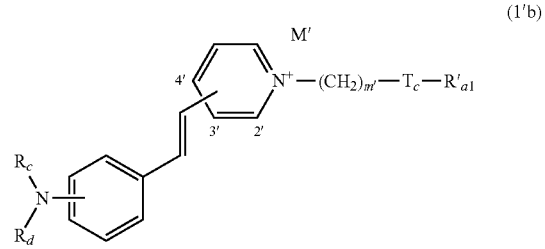

(1'b)

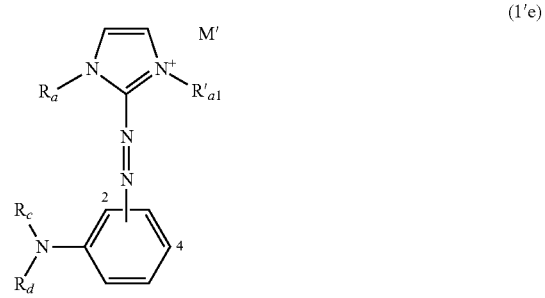

(1'e)

-continued

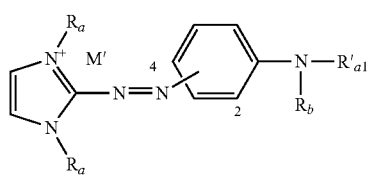

(1'g)

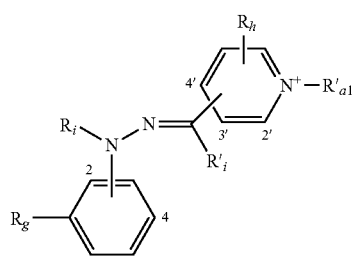

(1'i)

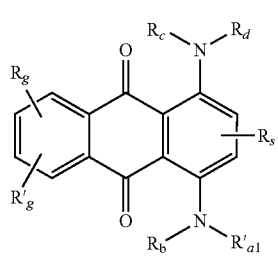

(1'j)

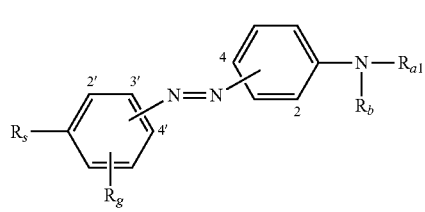

(1'k)

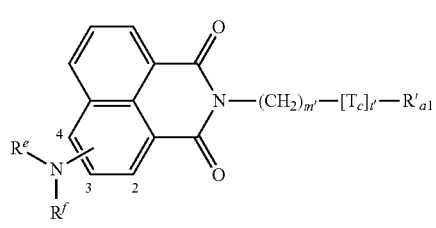

(1'm)

in which formulae (I'a), (I'b), (I'e), (I'g), (I'i), (I'j), (I'k) and (1'm):
- R'$_{a1}$ represents a group —(CH$_2$)$_r$—CH=CH$_2$ with r being an integer inclusively between 2 and 10, and particularly r being equal to 2 or 3; preferentially, R$_{a1}$ represents —CH$_2$—CH$_2$—CH=CH$_2$;
- R$_a$ represents a group (C$_1$-C$_4$)alkyl such as methyl;
- R$_j$ and R'$_j$ represent a hydrogen atom or a group (C$_1$-C$_4$) alkyl, such as methyl;
- R$_b$ represents a hydrogen atom or a group (C$_1$-C$_4$)alkyl such as methyl; preferentially, R$_b$ is a hydrogen atom;
- R$_g$ and R'$_g$ are as defined previously and preferentially represent a hydrogen atom;
- R$_s$ represents a sulfonate radical (O)$_2$S(O$^-$)—, M$^+$ such as sodium sulfonate; preferentially, R$_s$ is ortho to the group R$_c$R$_d$N— of (I'j)
- R$_i$ with R$_g$, R'$_i$ with R$_h$, borne by two adjacent atoms, together form a cycloalkyl group, in particular, R$_i$ with R$_g$, form a cycloalkyl such as cyclohexyl;
- T$_c$ represents a group chosen from a radical —O—, C(O)—, —N(R)— or a combination thereof with R representing a hydrogen atom or a group (C$_1$-C$_4$)alkyl such as methyl, and more particularly T$_c$ represents a group —N(R)—C(O)—;
- m' is 1, 2 or 3;
- t' is 0 or 1; preferentially, t' is 0;
- R$_c$ and R$_d$ represent identical groups (C$_1$-C$_3$)alkyl optionally substituted with a hydroxyl group, such as methyl or hydroxyethyl;
- the amino group of the compounds (1m) is linked to the carbon atoms of a phenyl group in position 2, 3 or 4, preferably 4;
- R$^e$, R$^f$, R$^g$ and R$^h$, which may be identical or different, represent a hydrogen atom or a C$_1$-C$_6$ alkyl group which is optionally substituted, preferentially with a di(C$_1$-C$_6$)alkylamino or tri(C$_1$-C$_6$)alkylammonium group such as trimethylammonium; and
- M' representing an organic or mineral anionic counterion;
- it being understood that the styryl, hydrozono or azo function is in position 2 (ortho) or 4 (para) relative to the phenyl, preferentially in position 4 and that the styryl or hydrazono function is in position 2' (ortho) or 4' (para) relative to the pyridinium, or 2' (ortho) or 4' (para) relative to the phenyl for (I'k), preferentially in position 4'. According to a preferred embodiment of the invention, the direct dyes are of formula (1'b).

As examples of dyes of formula (I), mention may be made especially of the following compounds:

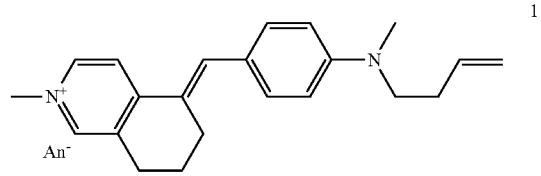

1

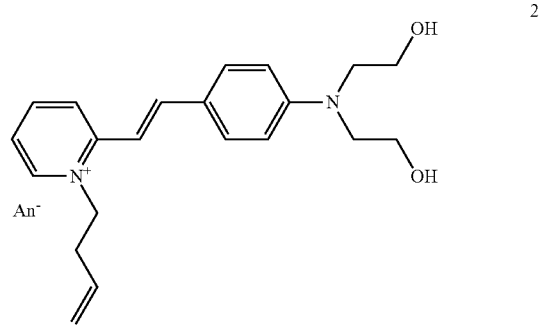

2

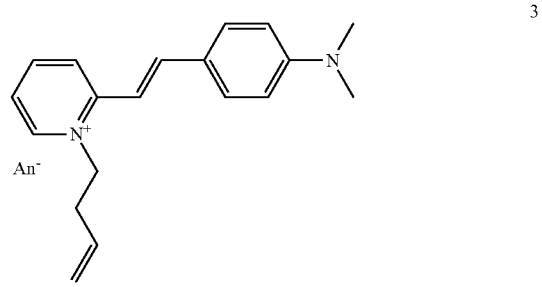

3

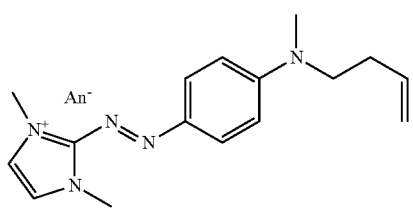
4
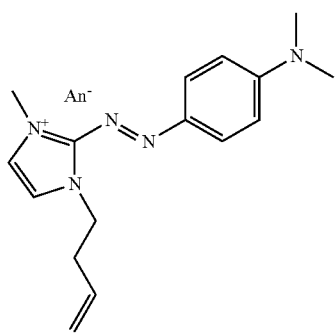
5
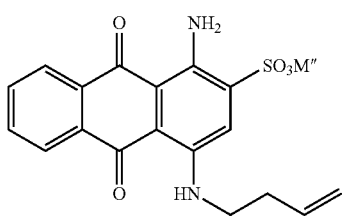
6
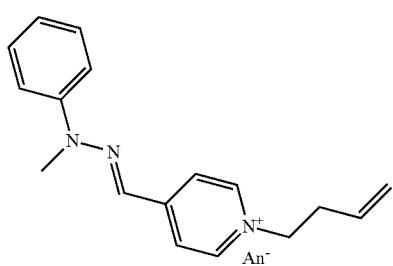
7
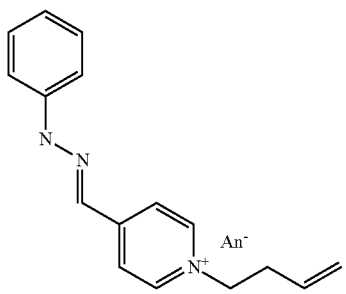
8
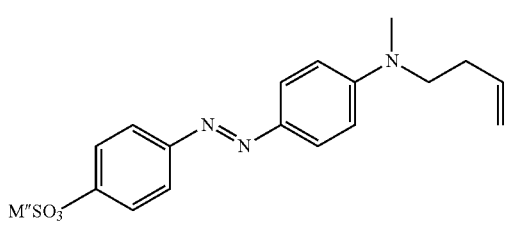
9
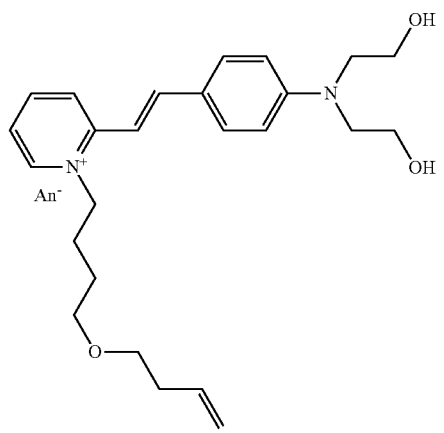
10
11
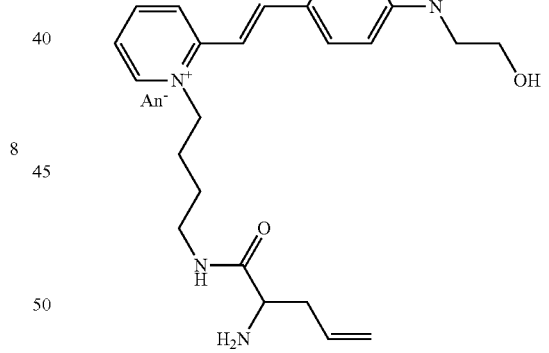
12
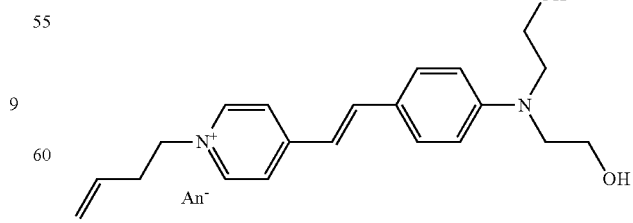
13
with An⁻ representing an organic or mineral anionic counterion, and $M^+$ N representing an organic or mineral OH cationic counterion.

According to one particular embodiment of the invention, the ingredient(s) i) are chosen from the dyes of formula (I) as defined previously with $R_{a1}$ representing a group derived from ascorbic acid Asc or *—$C_{sat}$—(X')$_p$-Asc, More particularly, the ingredient(s) i) are chosen from dyes (I) of formula (II) below:

$$A_1\text{-}(X_1)_p\text{—}C_{sat}\text{—}(X_1')_p\text{-Asc} \quad \text{(II)}$$

and also the organic or mineral acid salts, optical isomers, geometrical isomers, tautomers and solvates, such as hydrates, thereof;

in which formula (II):
- $A_1$ represents a coloured chromophore as defined previously;
- Asc represents a radical derived from ascorbic acid chosen from ascorbyl and dehydroascorbyl radicals, chosen from formulae (II-1) to (II-4), and which is linked to the rest of the molecule via one of the substituents $R_5$, $R_6$, $R_7$, $R_8$ or $R_9$, or alternatively said radical is linked to the rest of the molecule directly via one of the carbon atoms bearing the substituents $R_5$, $R_6$, $R_7$, $R_8$ or $R_9$, in which case one of these substituents is absent:

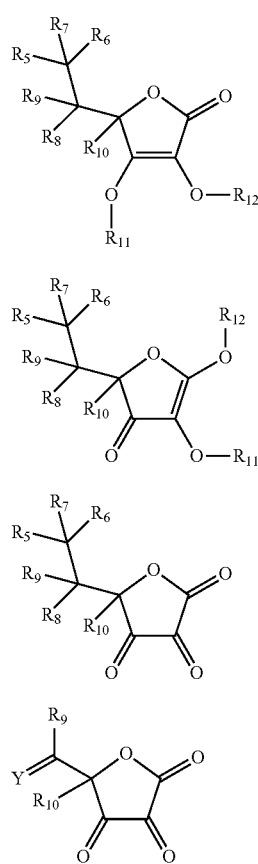

in which formulae (II-1) to (II-4):
- $R_5$, $R_6$, $R_7$, $R_8$, $R_9$ and $R_{10}$, which may be identical or different, represent a hydrogen atom or a group chosen from: i) ($C_1$-$C_8$)alkyl, ii) hydroxyl, iii) carboxyl, iv) and —O-protected with a protecting group;
- or alternatively $R_5$ and $R_9$ together form a divalent group —O—$(CR_aR_b)_n$—O— with $R_a$ and $R_b$, which may be identical or different, representing a hydrogen atom or a group ($C_1$-$C_8$)alkyl such as methyl or t-butyl, ($C_1$-$C_8$)alkoxy, aryl, (poly)halo($C_1$-$C_8$)alkyl such as trichloromethyl, and n being equal to 1, 2 or 3, and in particular $R_5$ and $R_9$ together form a divalent group —O—$CH_2$—$CH_2$—O— or —O—C$(CH_3)_2$—O—;
- $R_{11}$ and $R_{12}$, which may be identical or different, represent a hydrogen atom, an alkali metal, an alkaline-earth metal or a protecting group;
- or alternatively $R_{11}$ and $R_{12}$ together form a divalent group —$(CR_aR_b)_n$— with $R_a$ and $R_b$ and n as defined previously;
- Y represents an oxygen atom or a sulfur atom;
- $X_1$ and $X'_1$, which may be identical or different, represent:
  - a linear or branched, saturated or unsaturated divalent $C_1$-$C_{30}$ hydrocarbon-based chain, optionally interrupted and/or optionally terminated at one or both of its ends with one or more divalent groups or combinations thereof chosen from:
    —N(R)—; —N$^+$(R)(R')—, Q$^-$; —O—; —S—; —C(O)—; —S(O)$_2$— with R and R', which may be identical or different, chosen from a hydrogen atom and a $C_1$-$C_4$ alkyl, hydroxy($C_1$-$C_8$)alkyl or amino($C_1$-$C_8$)alkyl radical and Q$^-$ represents an organic or mineral anionic counterion;
  - an aromatic or non-aromatic, saturated or unsaturated, fused or non-fused (hetero)cyclic radical optionally comprising one or more identical or different, optionally substituted heteroatoms;
  - a divalent group or a combination chosen from:
    —N(R)—; —N$^+$(R)(R')—, Q$^-$; —O—; —S—; —C(O)—; —S(O)$_2$— with R, R' and Q$^-$ as defined previously;
  - preferentially, the divalent group(s) or combinations thereof are chosen from —O—; —N(R)—; —C(O)— with R chosen from a hydrogen atom and a $C_1$-$C_4$ alkyl radical;
- p and p', which may be identical or different, represent an integer equal to 0 or 1; and
- $C_{sat}$ represents a linear or branched, optionally substituted, optionally cyclic $C_1$-$C_{18}$ alkylene chain.

More particularly, the ingredient(s) i) are chosen from the direct dyes of formulae (II'$_a$), (II'$_b$), (II'$_c$), (II'$_f$), (II'$_g$), (II'$_i$), (II'$_j$), (II'$_k$), (II'$_m$) and (II'$_n$) below:

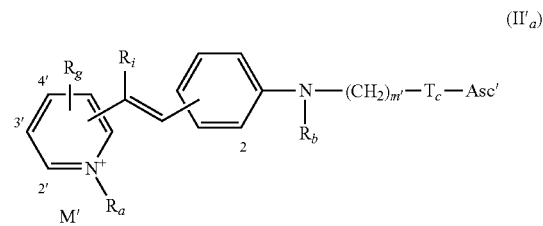

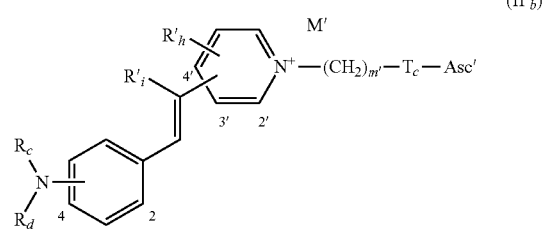

(II'c)
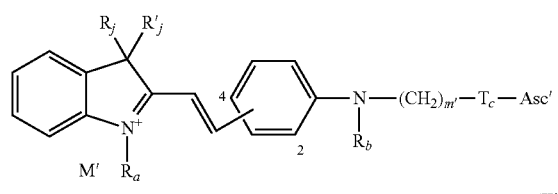

(II'd)
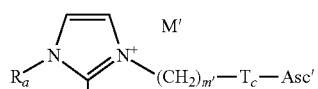
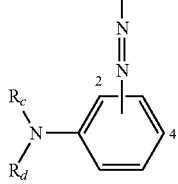

(II'e)
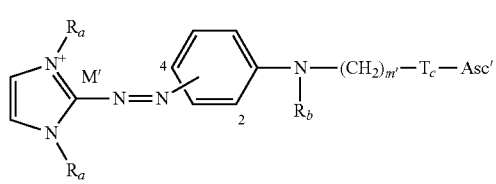

(II'f)
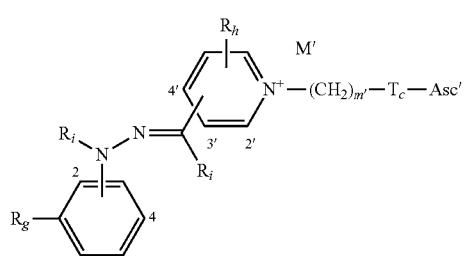

(II'g)
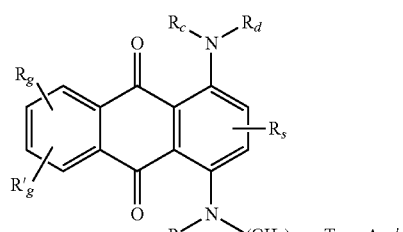

(II'h)
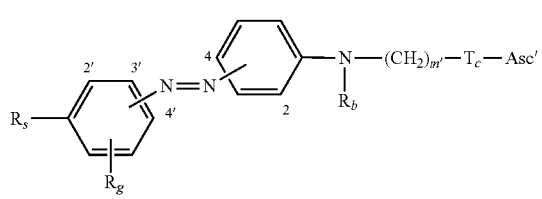

(II'i)
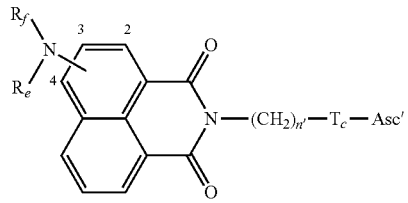

(II'j)
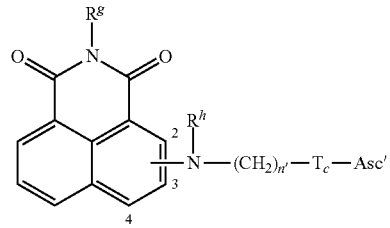

in which formulae (II'$_a$) to (II'$_j$):
Asc' represents a group chosen from (II"-1), (II"-2), (II"-3) and (II"-4)

(II"-1)
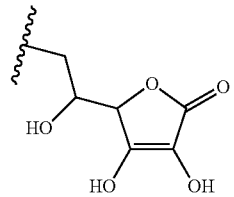

(II"-2)
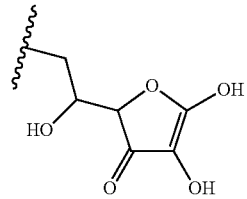

(II"-3)
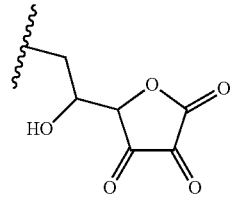

(II"-4)
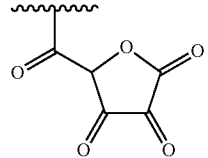

with ~~~ representing the point of attachment of Asc to the rest of the molecule by $T_c$;

$R_a$, $R_j$ and $R'_j$ represent a group $(C_1$-$C_4)$alkyl such as methyl;

$R_b$ represents a hydrogen atom or a group $(C_1$-$C_4)$alkyl such as methyl; preferentially, $R_b$ is a hydrogen atom;

$R_g$ and $R'_g$ are as defined previously and preferentially represent a hydrogen atom;

$R_s$ represents a sulfonate radical $(O)_2S(O^-)$—, M$^-$ such as sodium sulfonate; preferentially, $R_s$ is ortho to the group $R_cR_dN$— of (I'$_j$)

$R_i$ with $R_g$, $R'_i$ with $R_h$ borne by two adjacent atoms, together form a cycloalkyl group, particularly for (II'$_a$) and (II'$_b$), form a cycloalkyl such as cyclohexyl;

$T_c$ represents a group chosen from a radical —O—, C(O)—, —N(R)— or a combination thereof with R representing a hydrogen atom or a group $(C_1-C_4)$alkyl such as methyl, and more particularly $T_c$ represents a group —C(O)—O— or —N(R)—C(O)—;

m' is 1, 2 or 3;

n' is an integer between 1 and 10 inclusive, and more particularly between 3 and 6, such as 5;

$R_c$ and $R_d$ represent identical groups $(C_1-C_3)$alkyl optionally substituted with a hydroxyl group, such as methyl or hydroxyethyl;

$R^e$ and $R^g$ represent a $C_1-C_6$ alkyl group substituted with a group di$(C_1-C_6)$alkylamino or tri$(C_1-C_6)$alkylammonium, $M^-$;

$R^f$ and $R^h$ represent a hydrogen atom or a $C_1-C_6$ alkyl group; preferably the amino group $R^fR^eN$— or —N$(R^h)$— is in position 4 of the naphthalimidyl radical; and M' representing an organic or mineral anionic counterion;

it being understood that the styryl, hydrozono or azo function is in position 2 (ortho) or 4 (para) relative to the phenyl, preferentially in position 4 and that the styryl or hydrazono function is in position 2' (ortho) or 4' (para) relative to the pyridinium, or 2' (ortho) or 4' (para) relative to the phenyl for (II'$_h$), preferentially in position 4'.

According to an even more preferred embodiment of the invention, the ingredient(s) i) are chosen from those of formulae (II'$_h$) and (II'$_i$).

As examples of dyes bearing a group derived from ascorbic acid, mention may be made especially of compounds 1 to 18 of patent application FR 2 967 683.

According to another particular embodiment of the invention, the ingredient(s) i) are chosen from the direct dyes of formula (I) as defined previously with $R_{a1}$ representing a group HET or *—$C_{sat}$—$(X'_{f})_p$-HET. More particularly, the ingredient(s) i) are chosen from the dyes of formulae (III) and (III'):

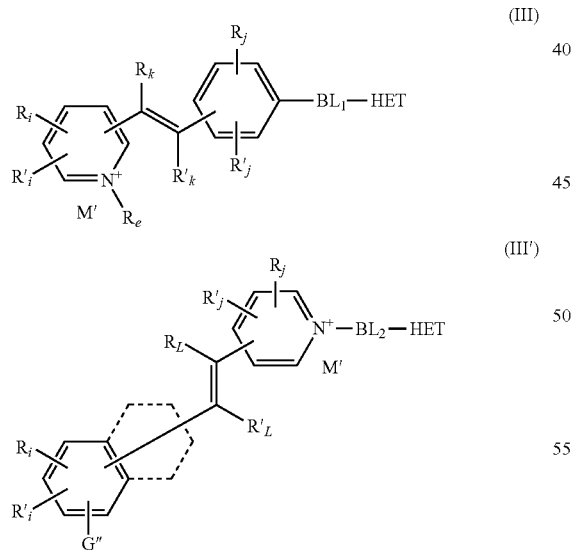

and also the organic or mineral acid salts, optical isomers, geometrical isomers and tautomers thereof and solvates thereof such as hydrates;

in which formulae (III) and (III'):

G" represents a group —NR$_g$R$_h$, or $(C_1-C_6)$alkoxy; preferentially, G" represents a group —NR$_g$R$_h$ preferentially para to the styryl group;

$R_e$ represents an optionally substituted group $(C_1-C_6)$alkyl; preferentially, $R_e$ represents a group $(C_1-C_3)$alkyl optionally substituted with a hydroxyl group, preferentially unsubstituted, such as methyl;

$R_g$ and $R_h$, which may be identical or different, represent a hydrogen atom, an aryl$(C_1-C_4)$alkyl or $(C_1-C_6)$alkoxy group or an optionally substituted $(C_1-C_6)$alkyl group; $R_g$ and $R_h$ preferentially represent a hydrogen atom or a group $(C_1-C_3)$alkyl optionally substituted with i) a hydroxyl group, ii) amino, iii) (di)$(C_1-C_3)$alkylamino, or iv) quaternary ammonium $(R''')(R'''')(R''''')N^+$—;

or alternatively two adjacent radicals $R_g$ and $R_h$, borne by the same nitrogen atom, together form a heterocyclic or heteroaryl group; preferentially, the heterocycle or heteroaryl is monocyclic and 5- to 7-membered; more preferentially, the groups are chosen from imidazolyl and pyrrolidinyl; in particular, $R_g$ and $R_h$ represent identical groups, and preferentially $R_g$ and $R_h$ represent a $C_1-C_3$ alkyl optionally substituted with a hydroxyl group, such as methyl, hydroxyethyl and 2-hydroxypropyl;

$R_i$, $R'_i$, $R_j$ and $R'_j$, which may be identical or different, represent a hydrogen atom, a halogen atom, an amino, $(C_1-C_4)$alkylamino, di$(C_1-C_4)$alkylamino, cyano, carboxyl, hydroxyl or trifluoromethyl group, an acylamino, $C_1-C_4$ alkoxy, (poly)hydroxy$(C_2-C_4)$alkoxy, $(C_1-C_4)$alkylcarbonyloxy$(C_1-C_4)$alkoxycarbonyl, $(C_1-C_4)$alkylcarbonylamino, acylamino, carbamoyl or $(C_1-C_4)$alkylsulfonylamino radical, an aminosulfonyl radical, or a $(C_1-C_{16})$alkyl radical optionally substituted with a group chosen from $(C_1-C_{12})$alkoxy, hydroxyl, cyano, carboxyl, amino, $(C_1-C_4)$alkyl-amino and di$(C_1-C_4)$alkylamino, or alternatively the two alkyl radicals borne by the nitrogen atom of the amino group form a 5- to 7-membered heterocycle optionally comprising another nitrogen or non-nitrogen heteroatom; preferentially, $R_i$, $R'_i$, $R_j$ and $R'_j$ represent a hydrogen or halogen atom or a $(C_1-C_3)$alkyl group; more preferentially, $R_i$, $R'_i$, $R_j$ and $R'_j$ represent a hydrogen atom;

or alternatively two groups $R_i$ and $R'_i$; $R_j$ and $R'_j$; borne by two adjacent carbon atoms together form a benzo or indeno ring, a fused heterocycloalkyl or fused heteroaryl group; the benzo, indeno, heterocycloalkyl or heteroaryl ring being optionally substituted with a halogen atom, an amino, $(C_1-C_4)$alkylamino, $(C_1-C_4)$dialkylamino, nitro, cyano, carboxyl, hydroxyl or trifluoromethyl group, an acylamino, $(C_1-C_4)$alkoxy, (poly)hydroxy$(C_2-C_4)$alkoxy, alkylcarbonyloxy, alkoxycarbonyl or alkylcarbonylamino radical, an acylamino, carbamoyl or alkylsulfonylamino radical, an aminosulfonyl radical, or a $(C_1-C_{16})$alkyl radical optionally substituted with: a group chosen from $(C_1-C_{12})$alkoxy, hydroxyl, cyano, carboxyl, amino, $(C_1-C_4)$alkylamino, $(C_1-C_4)$dialkylamino, or alternatively the two alkyl radicals borne by the nitrogen atom of the amino group form a 5- to 7-membered heterocycle optionally comprising another nitrogen or non-nitrogen heteroatom; preferentially, $R_i$ and $R'_i$ or $R_j$ and $R'_j$ together form a benzo group; or alternatively $R_j$ or $R'_j$ with $R_i$ form, together with the carbon atom that bears them, a cycloalkyl or cycloalkenyl group preferably of $C_6$ such as cyclohexyl; or cyclohexenyl;

or alternatively when G" represents —NR$_g$R$_h$ two groups $R_g$ and $R'_i$; $R_h$ and $R_i$; together form a saturated heteroaryl or heterocycle, optionally substituted with one or more groups $(C_1-C_6)$alkyl, preferentially a 5- to 7-membered heterocycle containing one or two heteroatoms chosen from nitrogen and oxygen; more preferentially the heterocycle is chosen from morpholinyl, piperazinyl, piperidyl and pyrrolidinyl groups;

$R_k$, $R_L$, $R'_L$ and $R'_k$, which may be identical or different, represent a hydrogen atom or a ($C_1$-$C_4$)alkyl group; more preferentially $R_k$, $R_L$, $R'_L$ and $R'_k$ represent a hydrogen atom:

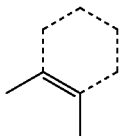

represents an aryl or heteroaryl group fused to the phenyl ring; or alternatively is absent from the phenyl ring; when the ring is present, the ring is preferentially a benzo; more preferentially, the ring is absent;

M' represents an organic or mineral anionic counterion;
HET represents a heterocycle chosen from (a), (b), (c), (d), (e) and (f) below:

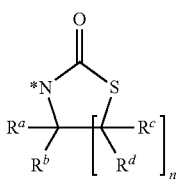 (a)

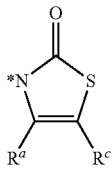 (b)

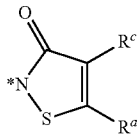 (c)

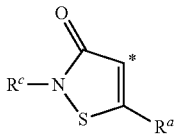 (d)

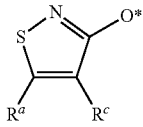 (e)

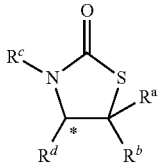 (f)

heterocycle (a), (b), (c), (d), (e) or (f) with:
$R_a$, $R_b$, $R_c$ and $R_d$, which may be identical or different, are as defined previously, and particularly represent a hydrogen atom or a ($C_1$-$C_4$)alkyl group or $R_a$ and $R_c$ together form a ($C_5$-$C_7$)cycloalkyl group and even more preferentially a hydrogen atom or $R_a$ and $R_c$ together form a cyclopentyl; n is 1 or 2;
and the asterisk * is as defined previously;
preferentially, HET represents a group chosen from (a') to (g') of the following formulae:

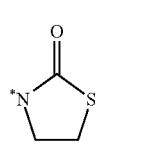 (a')

1,3-thiazolidin-2-on-3-yl

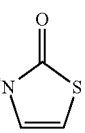 (b')

1,3-thiazol-2-on-3-yl

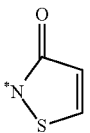 (c')

1,2-thiazol-3-on-2-yl

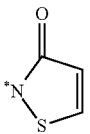 (d')

1,2-thiazol-3-on-4-yl

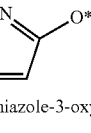 (e')

1,2-thiazole-3-oxy

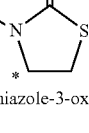 (f')

1,2-thiazole-3-oxy

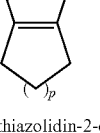 (g')

1,3-thiazolidin-2-on-4-yl with, in the structure (g'), p=1, 2, 3, preferably p=1 or 2 and more preferentially p=1 and, in the structure (f'), Rc is as defined previously, and preferably represents a hydrogen atom.

$BL_1$ represents a linear or branched, saturated or unsaturated $C_1$-$C_{30}$ hydrocarbon-based chain, optionally substituted and/or optionally interrupted and/or optionally terminated at one or both of its ends with one or more divalent groups or combinations thereof chosen from: —N(R)—; —N⁺(R)(R')—, Q-; —O—; —S—; —C(O)—; —S(O)₂— with R and R', which may be identical or different, chosen from a hydrogen atom and a (C₁-C₄)alkyl, hydroxy(C₁-C₄)alkyl or amino(C₁-C₄)alkyl radical and Q⁻ represents an anionic counterion; and BL₂ represents a linear or branched, saturated or unsaturated C₁-C₃₀ hydrocarbon-based chain, optionally substituted and/or optionally interrupted with one or more divalent groups or combinations thereof chosen from: —N(R)—; —N⁺(R)(R')—, Q-; —O—; —S—; —C(O)—; —S(O)₂— with R and R', which may be identical or different, chosen from a hydrogen atom and a (C₁-C₄)alkyl, hydroxy(C₁-C₄)alkyl or amino(C₁-C₄)alkyl radical and Q⁻ represents an anionic counterion.

Preferably, BL₁ and BL₂ represent a linear or branched, saturated or unsaturated, C₁-C₁₀ hydrocarbon-based chain, optionally substituted and/or optionally interrupted and/or optionally terminated at one or both of its ends with one or more divalent groups or combinations thereof, chosen from —N(R)—; —N⁺(R)(R')—, Q-; —O—; —S—; —C(O)— with R and R', which may be identical or different, chosen from a hydrogen atom and a (C₁-C₄)alkyl or hydroxy(C₁-C₄)alkyl radical and Q⁻ represents an anionic counterion. More preferentially, BL₁ and BL₂ represent a saturated or unsaturated, optionally substituted C₁-C₁₀ hydrocarbon-based chain, which is optionally interrupted and/or optionally terminated at one or both of its ends with one or more divalent groups chosen from —N(R)—; —C(O)— and combinations thereof, chosen from —N(R)—C(O)—; —C(O)—N(R)— with R and R', which may be identical or different, chosen from a hydrogen atom and a (C₁-C₄)alkyl radical, such as methyl.

As examples of fluorescent dyes according to the invention, mention may be made especially of the following compounds:

14

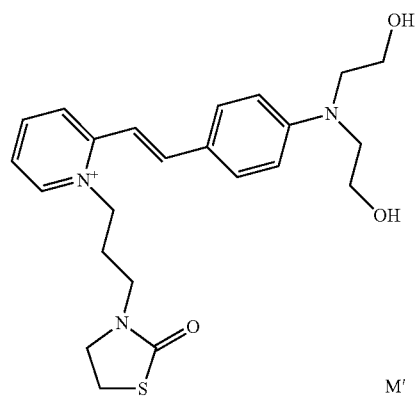

15

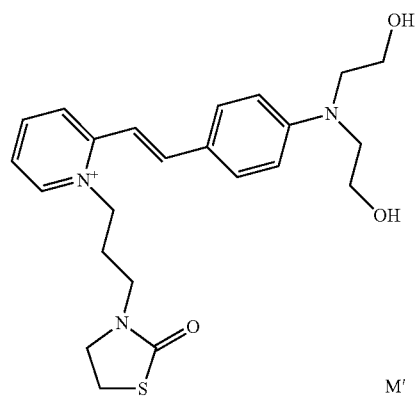

16

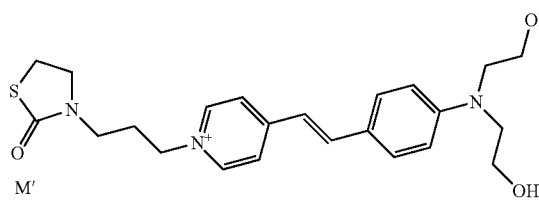

-continued

17

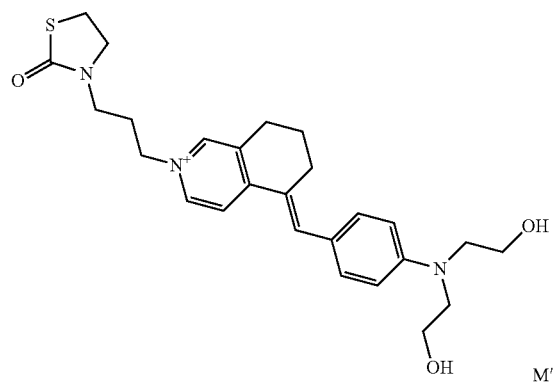

18

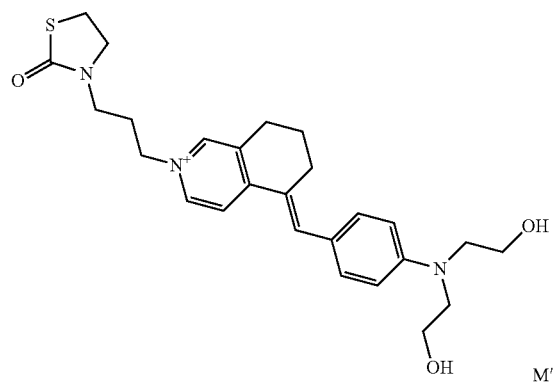

19

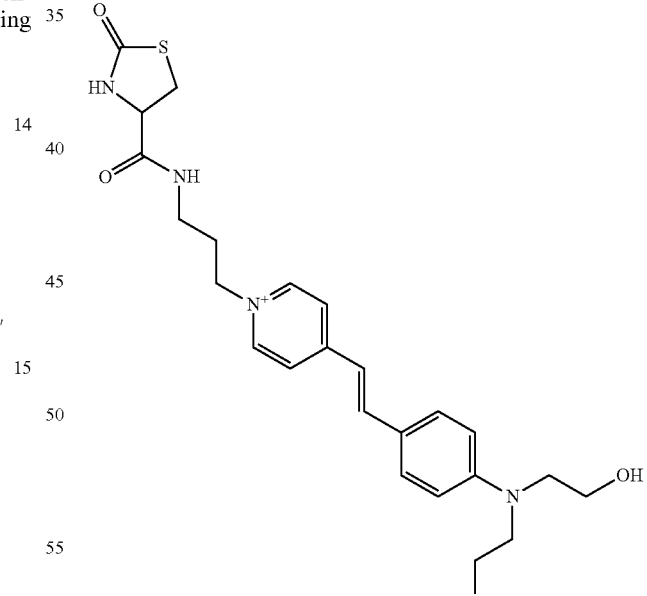

According to a particular embodiment, the ingredient(s) i) are of formula (I) as defined previously with $R_{a1}$ representing HET' or *—$C_{sat}$—(X'₁)$_p$-HET'. More particularly, the ingredient(s) i) are chosen from the dyes according to the invention chosen from the compounds of formulae (IV-1) to (IV-5):

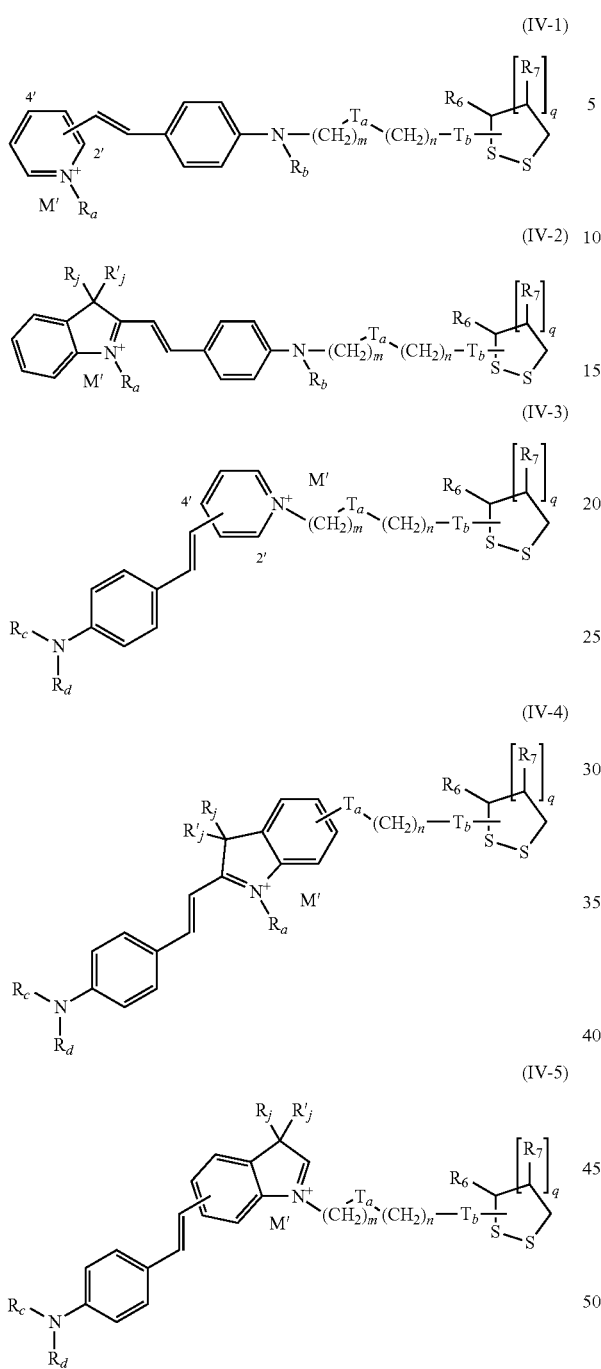

in which formulae (IV-1) to (IV-5):
$R_a$, $R_b$, $R_j$ and $R'_j$ represent a $C_1$-$C_4$ alkyl group such as methyl;
$R_6$ and $R_7$ represent a hydrogen atom or a $C_1$-$C_4$ alkyl group such as methyl, $T_b$ being linked directly to the carbon atom alpha or beta to the disulfide function of the heterocycle;
m and n, which may be identical or different, represent an integer between 0 and 7 inclusive, with m between 0 and 3 and n equal to 0, 1, 2, 3 or 4;
$T_a$ and $T_b$, which may be identical or different, represent i) a covalent σ bond; or ii) a group chosen from a radical —O—, —C(O)—, —N(R)— or a combination thereof such as —NR—C(O)—, —C(O)—NR, —O—C(O)—, —C(O)—O— or —C(O)—NR—C(O)— with R representing a hydrogen atom or a $C_1$-$C_4$ alkyl group, and particularly R is a hydrogen atom or a methyl;
q is 1, 2 or 3; particularly, q is 1;
$R_c$ and $R_d$ represent identical groups ($C_1$-$C_3$)alkyl optionally substituted with a hydroxyl group, such as methyl, hydroxyethyl and 2-hydroxypropyl; and
M' representing an organic or mineral anionic counterion; it being understood that in formulae (IV-1) and (IV-3), the pyridinium group is linked to the styryl via the carbon atom in position 2' (ortho) or 4' (para).

As examples of fluorescent dyes bearing a disulfide heterocyclic group, mention may be made especially of compounds 1 to 68 of patent application WO 2011/054966.

According to another particular embodiment, the ingredient(s) i) are of formula (I) as defined previously with $R_{a1}$ representing a group $C_{sat}$—S—U. In particular, the ingredient(s) i) are chosen from direct dyes bearing a disulfide function, a thiol function or a protected-thiol function, especially of formula (V): $A_1$-$(X_1)_p$—$C_{sat}$—S—U
salts thereof with an organic or mineral acid, optical or geometric isomers thereof, tautomers thereof, and solvates thereof such as hydrates,
in which formula (V):
U represents a radical chosen from a) *—S—$C'_{sat}$—$(X'_1)_{p'}$-$A'_1$ and b) *—Y;
$A_1$ and $A'_1$, which may be identical or different, represent a radical containing at least one anionic, cationic, zwitterionic or neutral chromophore as defined previously, preferably cationic;
Y represents i) a hydrogen atom; or ii) a thiol-function protecting group; and
$X_1$, $X'_1$, p, p' $C_{sat}$ and $C'_{sat}$ are as defined previously for the compounds of formula (II).

One particular mode of the invention concerns the dyes bearing a disulfide function of formula (V) as defined previously, i.e. for which U represents the following radical a) *—S—$C'_{sat}$—$(X'_1)_{p'}$-$A'_1$.

According to another particular mode, the invention concerns the dyes of formula (V) bearing a thiol function as defined previously, i.e. U representing the radical b) *—Y.

Another particular embodiment of the invention relates to fluorescent dyes bearing a disulfide, thiol or protected-thiol function, for dyeing and/or lightening dark keratin fibres. More particularly, the fluorescent dyes bear a disulfide function.

According to one particular embodiment of the invention, the cationic direct dye of formula (V) is a thiol dye, i.e. Y represents i) a hydrogen atom.

In accordance with another particular embodiment of the invention, in the abovementioned formula (V), Y is a protecting group; in particular, Y represents a protecting group for the thiol function, chosen from the following radicals:
($C_1$-$C_4$)alkylcarbonyl;
($C_1$-$C_4$)alkylthiocarbonyl;
($C_1$-$C_4$)alkoxycarbonyl;
($C_1$-$C_4$)alkoxythiocarbonyl;
($C_1$-$C_4$)alkylthio-thiocarbonyl;
(di)($C_1$-$C_4$)(alkyl)aminocarbonyl;
(di)($C_1$-$C_4$)(alkyl)aminothiocarbonyl;
arylcarbonyl, for instance phenylcarbonyl;
aryloxycarbonyl;
aryl($C_1$-$C_4$)alkoxycarbonyl;

(di)($C_1$-$C_4$)(alkyl)aminocarbonyl, for instance dimethylaminocarbonyl;
($C_1$-$C_4$)(alkyl)arylaminocarbonyl;
carboxyl;
$SO_3^-$; $M^+$ with $M^+$ representing an alkali metal such as sodium or potassium, or alternatively a counterion of the cationic chromophore $A_1$ or $A'_1$ and $M^+$ are absent;
optionally substituted aryl such as phenyl, dibenzosuberyl or 1,3,5-cycloheptatrienyl;
optionally substituted heteroaryl;
optionally cationic, optionally substituted heterocycloalkyl, the heterocycloalkyl group especially represents a saturated or partially saturated 5-, 6- or 7-membered monocyclic group comprising from 1 to 4 heteroatoms chosen from oxygen, sulfur and nitrogen, such as di/tetrahydrofuryl, di/tetrahydrothiophenyl, di/tetrahydropyrrolyl, di/tetrahydropyranyl, di/tetra/hexahydrothiopyranyl, dihydropyridyl, piperazinyl, piperidinyl, tetramethylpiperidyl, morpholinyl, di/tetra/hexahydroazepinyl, di/tetrahydropyrimidinyl, these groups being optionally substituted with one or more groups such as ($C_1$-$C_4$) alkyl, oxo or thioxo; or the heterocycle represents the following group:

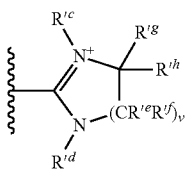

$An'''^-$ in which $R'^c$, $R'^d$, $R'^e$, $R'^f$, $R'^g$ and $R'^h$, which may be identical or different, represent a hydrogen atom or a ($C_1$-$C_4$) alkyl group, or alternatively two groups $R'^g$ with $R'^h$, and/or $R'^e$ with $R'^f$, form an oxo or thioxo group, or alternatively $R'^g$ with $R'^e$ together form a cycloalkyl; and v represents an integer between 1 and 3 inclusive; preferentially, $R'^c$ to $R'^h$ represent a hydrogen atom; and $An'''^-$ represents a counterion;
—C($NR'^cR'^d$)=$N^+R'^eR'^f$; $An'''^-$ with $R'^c$, $R'^d$, $R'^e$ and $R'^f$, which may be identical or different, represent a hydrogen atom or a ($C_1$-$C_4$)alkyl group; preferentially, $R'^c$ to $R'^f$ represent a hydrogen atom; and $An'''^-$ represents a counterion;
—C($NR'^cR'^d$)=$NR'^e$; with $R'^c$, $R'^d$ and $R'^e$ as defined previously;
optionally substituted (di)aryl($C_1$-$C_4$)alkyl such as 9-anthracenylmethyl, phenylmethyl or diphenylmethyl optionally substituted with one or more groups especially chosen from ($C_1$-$C_4$) alkyl, ($C_1$-$C_4$) alkoxy such as methoxy, hydroxyl, alkylcarbonyl or (di)($C_1$-$C_4$)(alkyl)amino such as dimethylamino;
optionally substituted (di)heteroaryl($C_1$-$C_4$)alkyl, the heteroaryl group especially being a cationic or noncationic, 5- or 6-membered monocyclic radical comprising from 1 to 4 heteroatoms chosen from nitrogen, oxygen and sulfur, such as pyrrolyl, furanyl, thiophenyl, pyridyl, pyridyl N-oxide such as 4-pyridyl or 2-pyridyl-N-oxide, pyrylium, pyridinium or triazinyl groups, optionally substituted with one or more groups such as alkyl, particularly methyl; advantageously, the (di)heteroaryl($C_1$-$C_4$) alkyl is (di)heteroarylmethyl or (di)heteroarylethyl;
$CR^1R^2R^3$ with $R^1$, $R^2$ and $R^3$, which may be identical or different, representing a halogen atom or a group chosen from:
($C_1$-$C_4$)alkyl;
($C_1$-$C_4$)alkoxy;
optionally substituted aryl such as phenyl optionally substituted with one or more groups, for instance ($C_1$-$C_4$)alkyl, ($C_1$-$C_4$)alkoxy or hydroxyl;
optionally substituted heteroaryl such as thiophenyl, furanyl, pyrrolyl, pyranyl or pyridyl, optionally substituted with a ($C_1$-$C_4$)alkyl group;
$P(Z^1)R'^1R'^2R'^3$ with $R'^1$ and $R'^2$, which may be identical or different, representing a hydroxyl, ($C_1$-$C_4$)alkoxy or alkyl group, $R'^3$ representing a hydroxyl or ($C_1$-$C_4$)alkoxy group, and $Z^1$ representing an oxygen or sulfur atom;
a sterically hindered ring; and
optionally substituted alkoxyalkyl, such as methoxymethyl (MOM), ethoxyethyl (EOM) and isobutoxymethyl.
In particular, Y represents a group chosen from oxazolium, isoxazolium, thiazolium, isothiazolium, 1,2,4-triazolium, 1,2,3-triazolium, 1,2,4-oxazolium, 1,2,4-thiadiazolium, pyrylium, pyridinium, pyrimidinium, pyrazinium, pyridazinium, triazinium and imidazolium, benzimidazolium, benzoxazolium, benzothiazolium, these groups being optionally substituted with one or more ($C_1$-$C_4$)alkyl groups, especially methyl.
In particular, Y represents a protecting group such as:
($C_1$-$C_4$)alkylcarbonyl, for instance methylcarbonyl or ethylcarbonyl;
arylcarbonyl, for instance phenylcarbonyl;
($C_1$-$C_4$)alkoxycarbonyl;
aryloxycarbonyl;
aryl($C_1$-$C_4$)alkoxycarbonyl;
(di)($C_1$-$C_4$)(alkyl)aminocarbonyl, for instance dimethylaminocarbonyl;
($C_1$-$C_4$)(alkyl)arylaminocarbonyl;
optionally substituted aryl such as phenyl;
5- or 6-membered monocyclic heteroaryl such as imidazolyl or pyridyl;
cationic 5- or 6-membered monocyclic heteroaryl such as pyrylium, pyridinium, pyrimidinium, pyrazinium, pyridazinium, triazinium, imidazolium; these groups being optionally substituted with one or more identical or different ($C_1$-$C_4$)alkyl groups such as methyl;
cationic 8- to 11-membered bicyclic heteroaryl such as benzimidazolium or benzoxazolium; these groups being optionally substituted with one or more identical or different ($C_1$-$C_4$)alkyl groups such as methyl;
cationic heterocycle having the following formula:

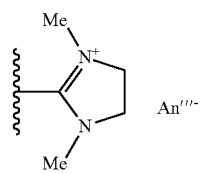 [SMILES: *C1=[N+](C)CCN1C]

—C(NH$_2$)=N$^+$H$_2$; An'''$^-$; with An'''$^-$ being an anionic counterion as defined previously;

—C(NH$_2$)=NH;

SO$_3^-$, M$^+$ with M$^+$ representing an alkali metal such as sodium or potassium.

As indicated previously, in formulae (V), C$_{sat}$ and C'$_{sat}$, independently of each other, represent a linear or branched, optionally substituted, optionally cyclic C$_1$-C$_{18}$ alkylene chain.

Substituents that may be mentioned include amino groups, (C$_1$-C$_4$)alkylamino groups, (C$_1$-C$_4$)dialkylamino groups, or the group R$^a$—Z$^a$—C(Z$^b$)— (in which Z$^a$, Z$^b$, which may be identical or different, represent an oxygen or sulfur atom or a group NR$^{a'}$, and R$^a$ represents an alkali metal, a hydrogen atom or a C$_1$-C$_4$ alkyl group and R$^{a'}$ represents a hydrogen atom or a C$_1$-C$_4$ alkyl group) preferably present on the carbon in the beta or gamma position relative to the sulfur atoms.

Preferably, in the case of formulae (V), C$_{sat}$ and C'$_{sat}$ represent a chain —(CH$_2$)$_k$— with k being an integer between 1 and 8 inclusive.

The radicals A$_1$ and/or A'$_1$ of formula (V) are as defined previously. Preferably, A$_1$ and/or A'$_1$ contain at least one cationic chromophore.

According to one preferred embodiment of the invention, the dyes (V) according to the invention are disulfides and comprise identical cationic chromophores A$_1$ and A'$_1$. More particularly, the dyes of formula (V) according to the invention are symmetrical disulfides, i.e. they contain a C2 axis of symmetry, i.e. formula (V) is such that:

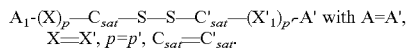

A$_1$-(X)$_p$—C$_{sat}$—S—S—C'$_{sat}$—(X'$_1$)$_{p'}$-A' with A=A', X=X', p=p', C$_{sat}$=C'$_{sat}$.

According to a preferred variant of the invention, the fluorescent chromophores A$_1$ and/or A'$_1$ are chosen from those of formulae (XVIIIa), (XIXa), (XXa) and (XXIa) as defined previously.

According to one embodiment of the invention, p=1, z=t'=0, t=1 and T represents —N(R)—, preferably in the para position on Ar relative to the olefin function —C(R$^c$)=C(R$^d$)—.

Particularly, in one variant, p=1, z=t'=0, t=1 and T represents —N(R)—, preferably in the para position on Ar relative to the styryl function —C(R$^c$)=C(R$^d$)— and T' represents a group —N(R)— or —N$^+$(R)(R$^o$)— or an imidazolium.

Preferably, W$^+$ or W$^+$ is an imidazolium, pyridinium, benzimidazolium, pyrazolium, benzothiazolium or quinolinium optionally substituted with one or more identical or different C$_1$-C$_4$ alkyl radicals.

According to one particularly preferred embodiment of the invention, A$_1$ and/or A'$_1$ represent the chromophore of formula (VIIIa) or (XIXa) as defined previously, preferably (XIXa) with m'=1, Ar representing a phenyl group substituted para to the styryl group —C(R$^d$)=C(R$^c$)— with a group (di)(hydroxy)(C$_1$-C$_6$)(alkyl)amino such as dihydroxy (C$_1$-C$_4$)alkylamino, and W'$^+$ representing an imidazolium or pyridinium group, preferably ortho- or para-pyridinium.

According to another particular embodiment of the invention, the dyes of formula (V) comprise a chromophore A$_1$ and/or A'$_1$ chosen from those derived from (poly)azo dyes such as (di)azo, and hydrazono dyes, more particularly chosen from the chromophores of formulae (IIIa), (III'a), (IVa), (IV'a) and (Va) as defined previously, more particularly chosen from (IIIa-1) and (IVa-1) as defined previously.

As examples of dyes of formula (V) of the invention, mention may be made of the disulfide dyes chosen from formulae (V-1) to (V-7) and the thiol or protected-thiol dyes chosen from formulae (V'-1) to (V'-7) below:

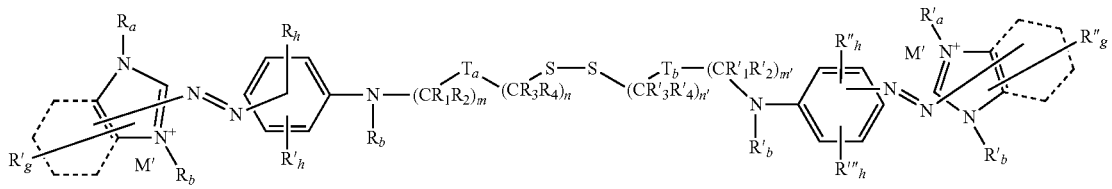

(V-1)

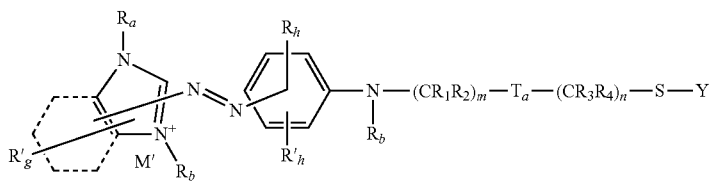

(V'-1)

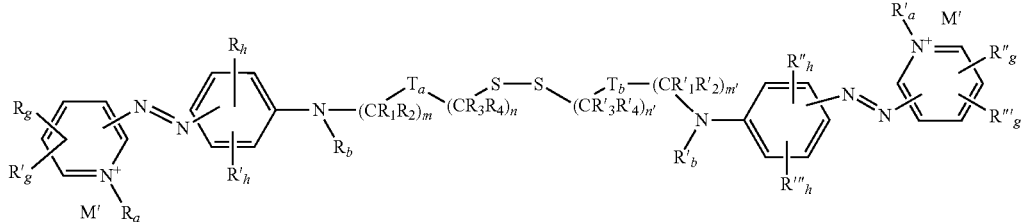

(V-2)

-continued
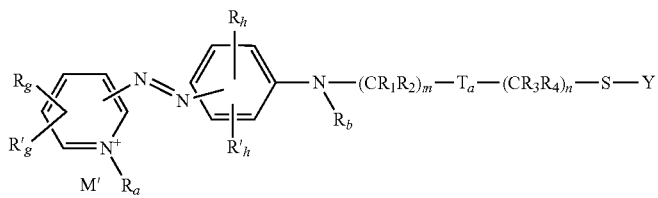
(V'-2)
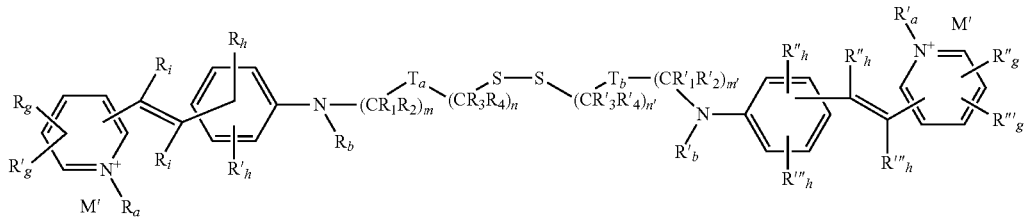
(V-3)
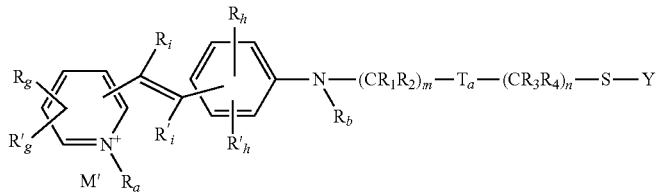
(V'-3)
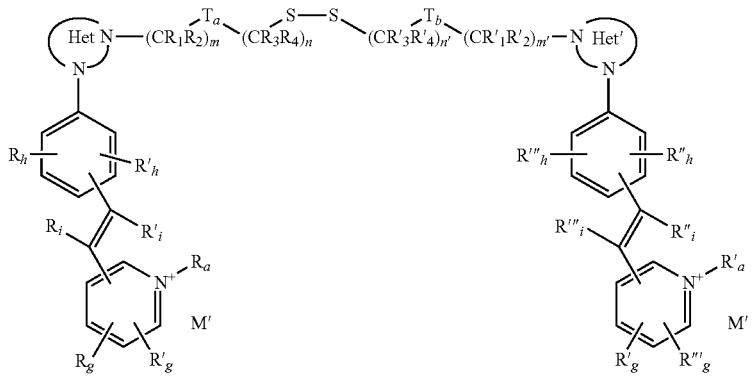
(V-4)
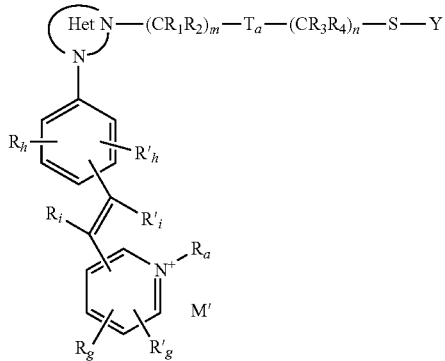
(V'-4)

-continued
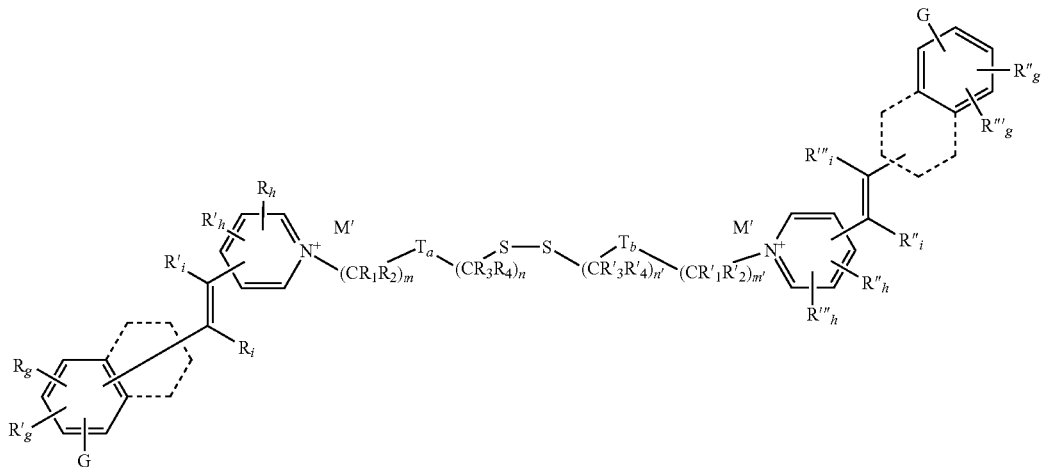
(V-5)
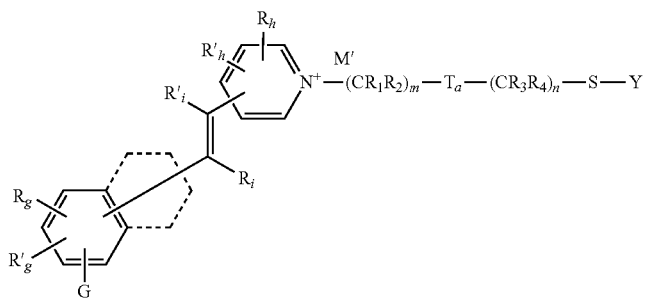
(V'-5)
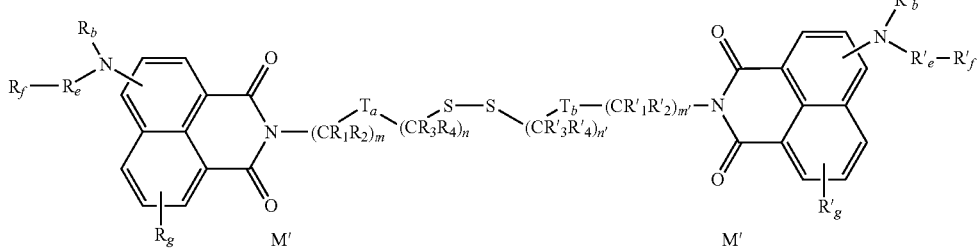
(V-6)
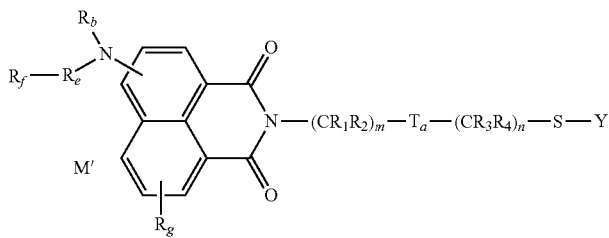
(V'-6)
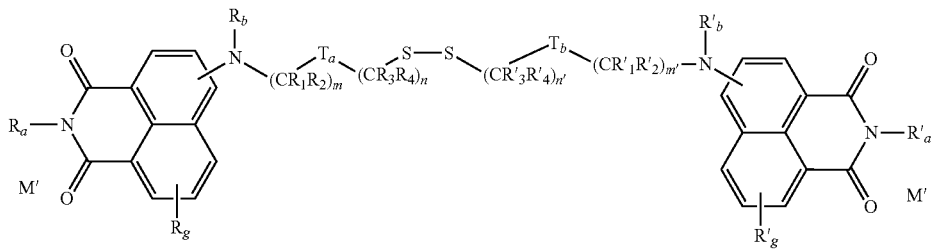
(V-7)

-continued

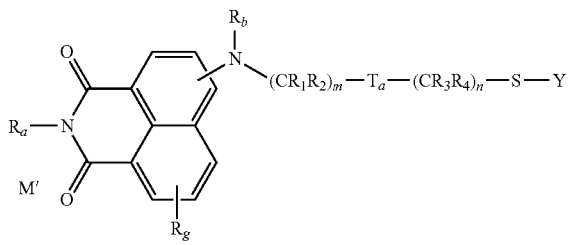

(V'-7)

in which formulae (V-1) to (V-7) and (V'-1) to (V'-7):

G and G', which may be identical or different, represent a group —$NR_cR_d$, —$NR'_cR'_d$ or optionally substituted $C_1$-$C_6$ alkoxy, preferentially unsubstituted; according to a preferred embodiment, G and G' represent a group —$NR_cR_d$ and a group —$NR'_cR'_d$, respectively; according to another embodiment, G and G' represent a $C_1$-$C_6$ alkoxy group;

$R^1$, $R^2$, $R^3$ and $R^4$, which may be identical or different, represent a hydrogen atom or a $C_1$-$C_6$ alkyl group; preferentially a hydrogen atom;

$R_a$ and $R'_a$, which may be identical or different, represent an aryl($C_1$-$C_4$)alkyl group or a $C_1$-$C_6$ alkyl group optionally substituted with a hydroxyl or amino, $C_1$-$C_4$ alkylamino or $C_1$-$C_4$ dialkyl amino group, said alkyl radicals possibly forming, with the nitrogen atom that bears them, a 5- to 7-membered heterocycle, optionally comprising another nitrogen or non-nitrogen heteroatom; preferentially, $R_a$ and $R'_a$ represent a $C_1$-$C_3$ alkyl group optionally substituted with a hydroxyl group, or a benzyl group;

$R_b$ and $R'_b$, which may be identical or different, represent a hydrogen atom, an aryl($C_1$-$C_4$)alkyl group or a $C_1$-$C_6$ alkyl group that is optionally substituted; preferentially, $R_b$ and $R'_b$ represent a hydrogen atom or a $C_1$-$C_3$ alkyl or benzyl group;

$R_c$, $R'_c$, $R_d$ and $R'_d$, which may be identical or different, represent a hydrogen atom, an aryl($C_1$-$C_4$)alkyl or $C_1$-$C_6$ alkoxy group or a $C_1$-$C_6$ alkyl group that is optionally substituted; $R_c$, $R'_c$, $R_d$ and $R'_d$ preferentially represent a hydrogen atom, a hydroxyl, $C_1$-$C_3$ alkoxy, amino or $C_1$-$C_3$ (di)alkylamino group, or a $C_1$-$C_3$ alkyl group that is optionally substituted with i) a hydroxyl group, ii) amino, iii) $C_1$-$C_3$ (di)alkylamino, or iv) quaternary ammonium (R")(R''')(R'''')N⁺—;

or alternatively two adjacent radicals $R_c$ and $R_d$, $R'_c$ and $R'_d$ borne by the same nitrogen atom together form a heterocyclic or heteroaryl group; preferentially, the heterocycle or heteroaryl is monocyclic and 5- to 7-membered; more preferentially, the groups are chosen from imidazolyl and pyrrolidinyl;

$R_e$ and $R'_e$, which may be identical or different, represent a linear or branched, optionally unsaturated divalent $C_1$-$C_6$ alkylenyl hydrocarbon-based chain;

$R_f$ and $R'_f$, which may be identical or different, represent a group di($C_1$-$C_4$)alkylamino, (R")(R''')N— or a quaternary ammonium group (R")(R''')(R'''')N⁺— in which R", R''' and R'''', which may be identical or different, represent a hydrogen atom or a $C_1$-$C_4$ alkyl group or alternatively (R")(R''')(R'''')N⁺— represents an optionally substituted cationic heteroaryl group, preferentially an imidazolinium group optionally substituted with a $C_1$-$C_3$ alkyl group;

$R_g$, $R'_g$, $R''_g$, $R'''_g$, $R_h$, $R'_h$, $R''_h$ and $R'''_h$, which may be identical or different, represent a hydrogen atom, a halogen atom, an amino, $C_1$-$C_4$ alkylamino, $C_1$-$C_4$ dialkylamino, cyano, carboxyl, hydroxyl or trifluoromethyl group, an acylamino, $C_1$-$C_4$ alkoxy, (poly)hydroxy($C_2$-$C_4$)alkoxy, alkylcarbonyloxy, alkoxycarbonyl or alkylcarbonylamino radical, an acylamino, carbamoyl or alkylsulfonylamino radical, an aminosulfonyl radical, or a $C_1$-$C_{16}$ alkyl radical optionally substituted with a group chosen from $C_1$-$C_{12}$ alkoxy, hydroxyl, cyano, carboxyl, amino, $C_1$-$C_4$ alkylamino and $C_1$-$C_4$ dialkylamino, or alternatively the two alkyl radicals borne by the nitrogen atom of the amino group form a 5- to 7-membered heterocycle optionally comprising another nitrogen or non-nitrogen heteroatom; preferentially, $R_g$, $R'_g$, $R''_g$, $R'''_g$, $R_h$, $R'_h$, $R''_h$, and $R'''_h$ represent a hydrogen or halogen atom or a $C_1$-$C_3$ alkyl group;

or alternatively two groups $R_g$ and $R'_g$; $R''_g$ and $R'''_g$; $R_h$ and $R'_h$; $R''_h$ and $R'''_h$ borne by two adjacent carbon atoms together form a benzo or indeno ring, a fused heterocycloalkyl or fused heteroaryl group; the benzo, indeno, heterocycloalkyl or heteroaryl ring being optionally substituted with a halogen atom, an amino, $C_1$-$C_4$ alkylamino, $C_1$-$C_4$ dialkylamino, nitro, cyano, carboxyl, hydroxyl or trifluoromethyl group, an acylamino, $C_1$-$C_4$ alkoxy, (poly)hydroxy($C_2$-$C_4$)alkoxy, alkylcarbonyloxy, alkoxycarbonyl or alkylcarbonylamino radical, an acylamino, carbamoyl or alkylsulfonylamino radical, an aminosulfonyl radical, or a $C_1$-$C_{16}$ alkyl radical optionally substituted with: a group chosen from $C_1$-$C_{12}$ alkoxy, hydroxyl, cyano, carboxyl, amino, $C_1$-$C_4$ alkylamino, $C_1$-$C_4$ dialkylamino, or alternatively the two alkyl radicals borne by the nitrogen atom of the amino group form a 5- to 7-membered heterocycle optionally comprising another nitrogen or non-nitrogen heteroatom; preferentially, $R_g$ and $R'_g$; $R''_g$ and $R'''_g$ together form a benzo group;

or alternatively two groups $R_i$ and $R_g$; $R'''_i$ and $R'''_g$; $R'_i$ and $R'_h$; and/or $R''_i$ and $R''_h$ together form a fused (hetero)cycloalkyl, preferentially cycloalkyl such as cyclohexyl;

or alternatively when G represents —$NR_cR_d$ and G' represents —$NR'_cR'_d$, two groups $R_c$ and $R'_g$; $R'_c$ and $R''_g$; $R_d$ and $R_g$; $R'_d$ and $R'''_g$ together form a saturated heteroaryl or heterocycle, optionally substituted with one or more groups $(C_1-C_6)$alkyl, preferentially a 5- to 7-membered heterocycle containing one or two heteroatoms chosen from nitrogen and oxygen; more preferentially the heterocycle is chosen from morpholinyl, piperazinyl, piperidyl and pyrrolidinyl groups;

$R_i$, $R'_i$, $R''_i$, and $R'''_i$, which may be identical or different, represent a hydrogen atom or a $C_1-C_4$ alkyl group;

$R_1$, $R_2$, $R_3$, $R_4$, $R'_1$, $R'_2$, $R'_3$ and $R'_4$, which may be identical or different, represent a hydrogen atom or a $C_1-C_4$ alkyl, $C_1-C_{12}$ alkoxy, hydroxyl, cyano, carboxyl, amino, $C_1-C_4$ alkylamino or $C_1-C_4$ dialkylamino group, said alkyl radicals possibly forming with the nitrogen atom that bears them a 5- to 7-membered heterocycle optionally comprising another nitrogen or non-nitrogen heteroatom; preferentially, $R_1$, $R_2$, $R_3$, $R_4$, $R'_1$, $R'_2$, $R'_3$, and $R'_4$ are hydrogen atoms or an amino group; more preferentially, $R_1$, $R_2$, $R_3$, $R_4$, $R'_1$, $R'_2$, $R'_3$ and $R'_4$ represent a hydrogen atom;

$T_a$ and $T_b$, which may be identical or different, represent i) either a covalent bond σ, ii) or one or more radicals or combinations thereof chosen from —S(O)$_2$—, —O—, —S—, —N(R)—, —N$^+$(R)(R$^o$)—, —C(O)—, with R, R$^o$, which may be identical or different, representing a hydrogen atom or a $C_1-C_4$ alkyl or $C_1-C_4$ hydroxyalkyl radical; or an aryl$(C_1-C_4)$alkyl, preferentially $T_a$ is identical to $T_b$ and represent a covalent bond σ or a group chosen from —N(R)—, —C(O)—N(R)—, —N(R)—C(O)—, —O—C(O)—, —C(O)—O— and —N$^+$(R)(R$^o$)—, with R, R$^o$ which may be identical or different representing a hydrogen atom or a $C_1-C_4$ alkyl group; more preferentially, $T_a$ and $T_b$ represent a σ bond; iii) or a cationic or non-cationic, preferentially monocyclic, preferentially identical heterocycloalkyl or heteroaryl radical, preferentially containing two heteroatoms (more preferentially two nitrogen atoms) and preferentially being 5- to 7-membered such as imidazolium;

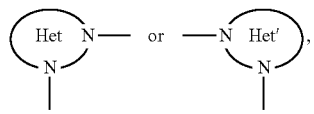

identical or different, represent an optionally substituted preferentially, the heterocycles are identical, monocyclic, saturated and 5- to 8-membered and comprise in total two nitrogen atoms;

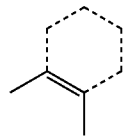

represents an aryl or heteroaryl group fused to the imidazolium or phenyl ring; or alternatively is absent from the imidazolium or phenyl ring; preferentially, when the ring is present, the ring is a benzo;

m, m', n and n', which may be identical or different, represent an integer between 0 and 6 inclusive, with m+n and m'+n', which may be identical or different, represent an integer between 1 and 10 inclusive; preferentially, m+n=m'+n'=an integer between 2 and 4 inclusive; more preferentially, m+n=m'+n'=an integer equal to 2;

Y is as defined previously for (V); in particular, Y represents a hydrogen atom or a protecting group such as:

$(C_1-C_4)$alkylcarbonyl, for instance methylcarbonyl or ethylcarbonyl;

arylcarbonyl, for instance phenylcarbonyl;

$(C_1-C_4)$alkoxycarbonyl;

aryloxycarbonyl;

aryl$(C_1-C_4)$alkoxycarbonyl;

(di)$(C_1-C_4)$(alkyl)aminocarbonyl, for instance dimethylaminocarbonyl;

$(C_1-C_4)$(alkyl)arylaminocarbonyl;

optionally substituted aryl such as phenyl;

5- or 6-membered monocyclic heteroaryl such as imidazolyl or pyridyl;

cationic 5- or 6-membered monocyclic heteroaryl such as pyrylium, pyridinium, pyrimidinium, pyrazinium, pyridazinium, triazinium, imidazolium; these groups being optionally substituted with one or more identical or different $(C_1-C_4)$alkyl groups such as methyl;

cationic 8- to 11-membered bicyclic heteroaryl such as benzimidazolium or benzoxazolium; these groups being optionally substituted with one or more identical or different $(C_1-C_4)$alkyl groups such as methyl;

cationic heterocycle having the following formula:

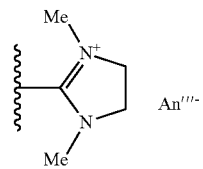 [SMILES: *C1=[N+](C)CCN1C]

—C(NH$_2$)=N$^+$H$_2$; An''''$^-$; with An''''$^-$ being an anionic counterion as defined previously;

—C(NH$_2$)=NH;

SO$_3^-$, M$^+$ with M$^+$ representing an alkali metal such as sodium or potassium; and M' representing an anionic counterion, derived from a salt of an organic or mineral acid, or from an organic or mineral base that ensures the electrical neutrality of the molecule.

In particular, the dyes of formula (V) are chosen from dyes with a naphthalimidyl disulfide, thiol or protected-thiol chromophore, chosen from formulae (V-5), (V'-5), (V-6) and (V'-6) as defined previously.

According to a preferred mode of the invention, the dyes of formula (V) are chosen from disulfide, thiol or protected-thiol dyes, chosen from formulae (V-8) and (V'-8) which bear an ethylene group linking the pyridinium part to the phenyl in the position ortho or para to the pyridinium, i.e. at 2-4', 4-2', 4-4':

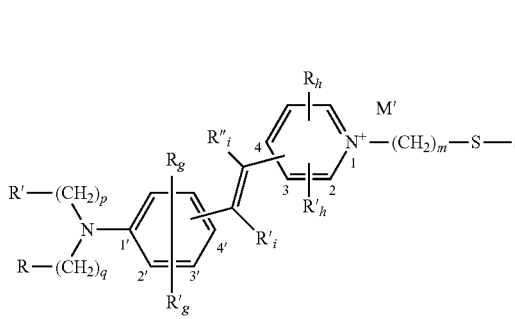

(V-8)

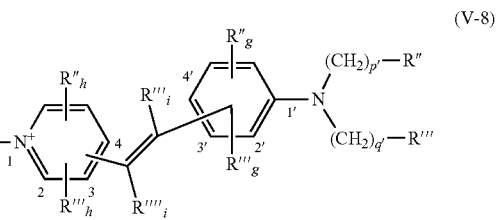

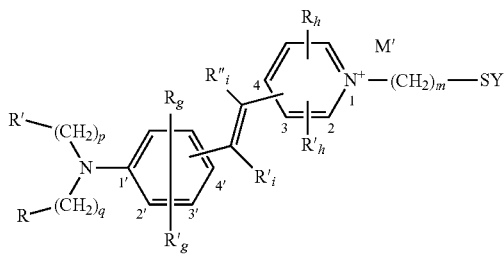

(V'-8)

in which formulae (V-8) and (V'-8):
- R and R''', which may be identical or different, represent a hydroxyl group, an amino group ($NR_aR^b$) or an ammonium group ($N^+R_aR_bR_c$), $An^-$; preferentially hydroxyl; with $R_a$, $R_b$ and $R_c$, which may be identical or different, representing a hydrogen atom or a ($C_1$-$C_4$) alkyl group;
- or alternatively two alkyl groups $R_a$ and $R_b$ of the amino or ammonium group form a 5- to 7-membered heterocycle optionally comprising another nitrogen or non-nitrogen heteroatom, such as morpholinyl, piperazinyl, piperidyl, pyrrolyl, morpholinium, piperazinium, piperidinium or pyrrolinium, and $An^-$ representing an anionic counterion;
- R' and R'', which may be identical or different, represent a hydrogen atom or a group as defined for R and R''', respectively;
- $R_g$, $R'_g$, $R''_g$, $R'''_g$, $R_h$, $R'_h$, $R''_h$ and $R'''_h$, which may be identical or different, represent a hydrogen atom, a halogen atom, an amino, di($C_1$-$C_4$)alkylamino, cyano, carboxyl, hydroxyl, trifluoromethyl, acylamino, $C_1$-$C_4$ alkoxy, (poly)hydroxy($C_2$-$C_4$)alkoxy, ($C_1$-$C_4$)alkylcarbonyloxy, ($C_1$-$C_4$)alkoxycarbonyl, ($C_1$-$C_4$)alkylcarbonylamino, acylamino, carbamoyl or ($C_1$-$C_4$)alkylsulfonylamino group, an aminosulfonyl radical, or a ($C_1$-$C_{16}$)alkyl radical optionally substituted with a group chosen from ($C_1$-$C_{12}$)alkoxy, hydroxyl, cyano, carboxyl, amino and di($C_1$-$C_4$)alkylamino, or alternatively the two alkyl radicals borne by the nitrogen atom of the amino group form a 5- to 7-membered heterocycle optionally comprising another nitrogen or non-nitrogen heteroatom; in particular, $R_g$, $R'_g$, $R''_g$, $R'''_g$, $R_h$, $R'_h$, $R''_h$ and $R'''_h$ represent a hydrogen atom or a ($C_1$-$C_4$) alkyl group;
- $R'_i$, $R''_i$, $R'''_i$ and $R''''_i$, which may be identical or different, represent a hydrogen atom or a ($C_1$-$C_4$)alkyl group; in particular $R'_i$, $R''_i$, $R'''_i$, and $R''''_i$ represent a hydrogen atom;
- m and m', which may be identical or different, represent an integer between 1 and 10 inclusive; in particular an integer between 2 and 4 inclusive; preferentially, m and m' are equal to 2;
- p, p', q and q', which may be identical or different, represent an integer between 1 and 6 inclusive;
- M' representing an anionic counterion; and
- Y is as defined previously;

it being understood that when the compound of formula (V-8) or (V'-8) contains other cationic parts, it is combined with one or more anionic counterions that afford formula (V-8) or (V'-8) electrical neutrality.

In particular, $R_h$ and $R''_h$ are ortho to the pyridinium group and $R'_h$ and $R'''_h$ represent a hydrogen atom. Another aspect of the invention concerns the dyes of formula (V-8) or (V'-8) bearing groups $R_g$, $R''_g$ in position 3' and $R'_g/R''_g$ which represent a hydrogen atom. Advantageously, the dyes of formulae (V-8) and (V'-8) bear their ethylene group para to the phenyl bearing the amino group: R'($CH_2)_p$—N—($CH_2)_q$—R and/or R''($CH_2)_{p'}$—N—($CH_2)_{q'}$—R''', i.e. in position 4', preferentially bear an ethylene or styryl group linking the pyridinium part to the phenyl ortho to the pyridinium, i.e. 2-4'.

According to another particular mode of the invention, the dyes of the invention belong to formula (V-9) or (V'-9):

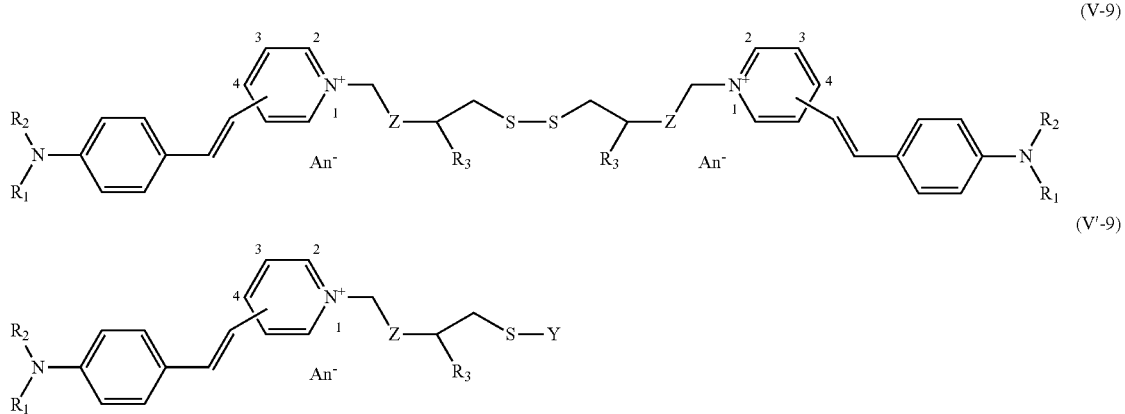

(V-9)

(V'-9)

in which formulae (V-9) and (V'-9):
- $R_1$ represents a $C_1$-$C_6$ alkyl group substituted with one or more hydroxyl groups or —C(O)OR' with R' representing a hydrogen atom, a $C_1$-$C_4$ alkyl group or alternatively a group —C(O)—O⁻ and, in the latter case, an anionic counterion An⁻ is absent; in particular R, represents a $C_1$-$C_6$ alkyl group substituted with one or more hydroxyl groups and more specifically with only one hydroxyl group;
- $R_2$ represents a $C_1$-$C_6$ alkyl group optionally substituted with one or more hydroxyl groups;
- or alternatively the groups $R_1$ and $R_2$ form, together with the nitrogen atom that bears them, a saturated heterocyclic radical substituted with at least one hydroxyl, (poly)hydroxy($C_1$-$C_4$)alkyl and/or —C(O)OR' group with R' representing a hydrogen atom, a $C_1$-$C_4$ alkyl group or alternatively a group —C(O)—O⁻ and, in the latter case, an anionic counterion An⁻ is absent; such as pyrrolidinyl and piperidyl;
- $R_3$ represents a hydrogen atom or a group —C(O)OR" with R" representing a hydrogen atom, an alkali metal or a $C_1$-$C_6$ alkyl group or alternatively $R_3$ represents a group —C(O)—O⁻ and, in the latter case, an anionic counterion An⁻ is absent;
- Z represents a divalent amido group —C(O)—N(R)—, —N(R)—C(O)—, or a divalent $C_1$-$C_{10}$ alkylene group interrupted with an amido group —C(O)—N(R)—, —N(R)—C(O)— such as —(CH$_2$)$_n$—C(O)—N(R)—(CH$_2$)$_p$—, —(CH$_2$)$_{n'}$—N(R)—C(O)—(CH$_2$)$_p$—, with n' representing an integer between 0 and 3 inclusive; preferentially, n' is equal to 0, 2, 3; p representing an integer between 0 and 4 inclusive, n" representing an integer between 0 and 3 inclusive and especially n'=n"=p=0 and R representing a hydrogen atom or a $C_1$-$C_6$ alkyl group;
- An⁻ represents an anionic counterion;
- Y is as defined previously;

it being understood that when the compound of formula (V-9) or (V'-9) contains other cationic parts, it is combined with one or more anionic counterions that afford formula (V-9) or (V'-9) electrical neutrality.

According to a particular mode of the invention, the dyes of the invention belong to formula (V-10) or (V'-10) below:

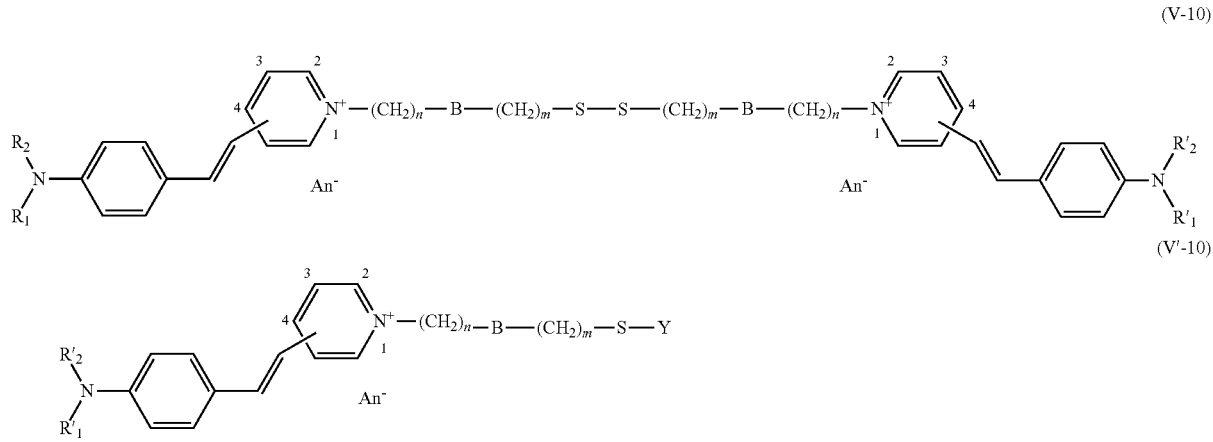

(V-10)

(V'-10)

in which formulae (V-10) and (V'-10):
- $R'_1$ represents a $C_1$-$C_4$ alkyl group substituted with one or more hydroxyl groups, particularly with only one hydroxyl group, or —C(O)OR' with R' representing a hydrogen atom, a $C_1$-$C_4$ alkyl group or a group —C(O)—O⁻ and, in the latter case, an anionic counterion An⁻ is absent; preferentially, $R'_1$ represents a $C_1$-$C_4$ alkyl group substituted with a hydroxyl group;
- $R'_2$ represents a $C_1$-$C_4$ alkyl group optionally substituted with one or more hydroxyl groups, particularly with only one hydroxyl group;

more particularly, R'₁ and R'₂ are identical;

An⁻ represents an anionic counterion as defined previously;

B represent a divalent amido group —C(O)—N(R)—, —N(R)—C(O)—, with R representing a hydrogen atom or a group $(C_1\text{-}C_6)$alkyl; preferentially, R=H;

n and m, which may be identical or different, represent an integer between 1 and 4 inclusive; preferentially, n is equal to 3 and m is equal to 2;

Y is as defined previously;

it being understood that the bond between the pyridinium ring and the double bond of the ethylene or styryl group is located in position 2 or 4 of the pyridinium, preferably at 4.

As examples of disulfide, thiol and protected-thiol direct dyes of formula (V) of the invention, mention may be made of the particular dyes having the chemical structures described in the following patent applications:

The non-fluorescent symmetrical dyes of paragraph [057] of patent application EP 1 647 580 A1 and the compounds of Examples 3 to 8 of the same application, The fluorescent dyes 1 to 25 of patent application WO 2007/110531;

The fluorescent dyes 1 to 49 of patent application WO 2007/110532;

The fluorescent dyes 1 to 28 of patent application WO 2007/110533;

The fluorescent dyes 1 to 149 of patent application WO 2007/110534;

The fluorescent dyes 1 to 16 of patent application WO 2007/110535;

The fluorescent dyes 1 to 18 of patent application WO 2007/110536;

The fluorescent dyes 1 to 32 of patent application WO 2007/110537;

The fluorescent dyes 1 to 16 of patent application WO 2007/110539;

The fluorescent dyes (1) to (36) of patent application WO 2007/110540;

The fluorescent dyes 1 to 63 of patent application WO 2007/110541;

The fluorescent dyes from page 18, line 1 to page 35, line 4 of patent application WO 2007/110542;

The dyes of paragraphs [0066] and [0067], the non-fluorescent dyes of page 23, lines 1 to 29 and the fluorescent dyes from page 23, line 30 to page 38, line 55 of patent application EP 2 053 094 A2;

The non-fluorescent dyes 1 to 54 of patent application FR 2 920 779 and of patent application FR 2 920 781;

The non-fluorescent dyes 1 to 50 of patent application WO 2009/034059 and FR 2 920 780;

The fluorescent dyes 1 to 42 of patent application EP 2 062 945 A1;

The fluorescent dyes 1 to 21 of patent EP 2 039 724 B1;

The fluorescent dyes 1 to 28 of patent application FR 2 921 380;

The fluorescent dyes 1 to 18 of patent application WO 2009/037324;

The fluorescent dyes 1 to 31 of patent application WO 2009/037325;

The fluorescent dyes 1 to 30 of patent application WO 2009/037348;

The fluorescent dyes 1 to 28 of patent application FR 2 921 375;

The fluorescent dyes 1 to 36 of patent application EP 2 075 288 A1;

The fluorescent dyes 1 to 32 of patent application EP 2 075 289 A1.

More particularly, the ingredient(s) i) are chosen from those of the following formulae:

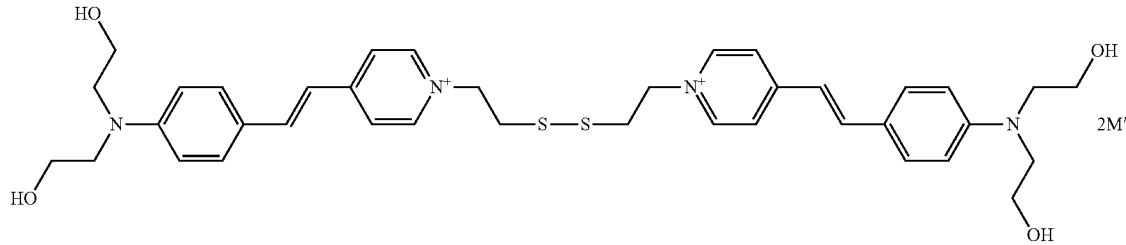

20

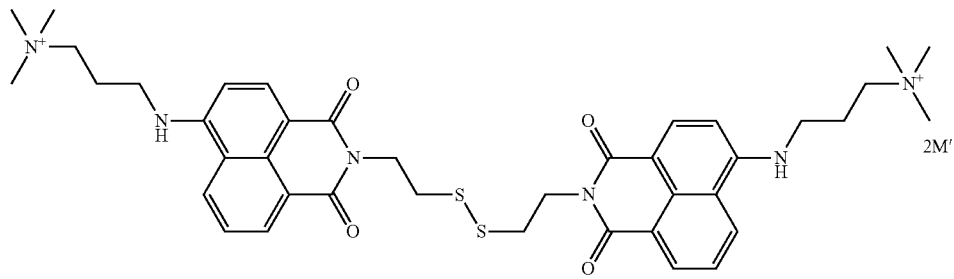

21

-continued

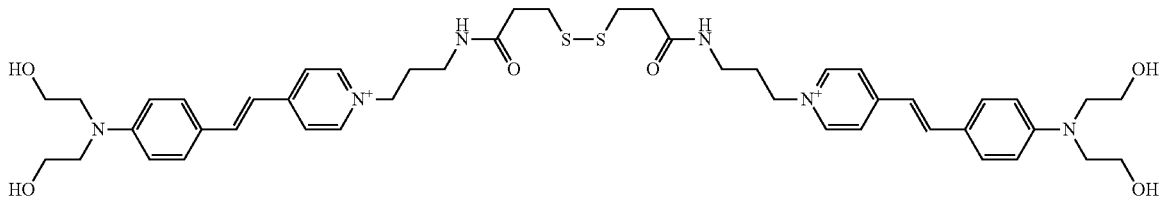

22

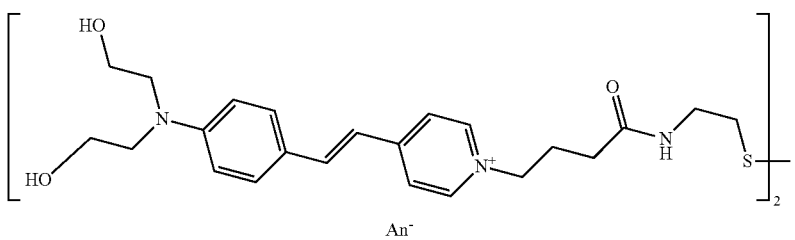

23

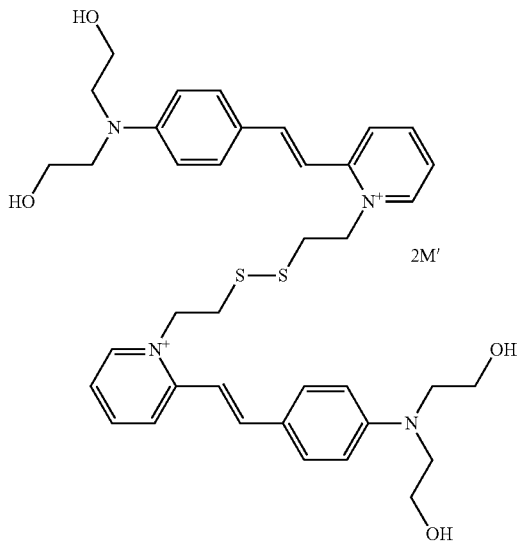

24

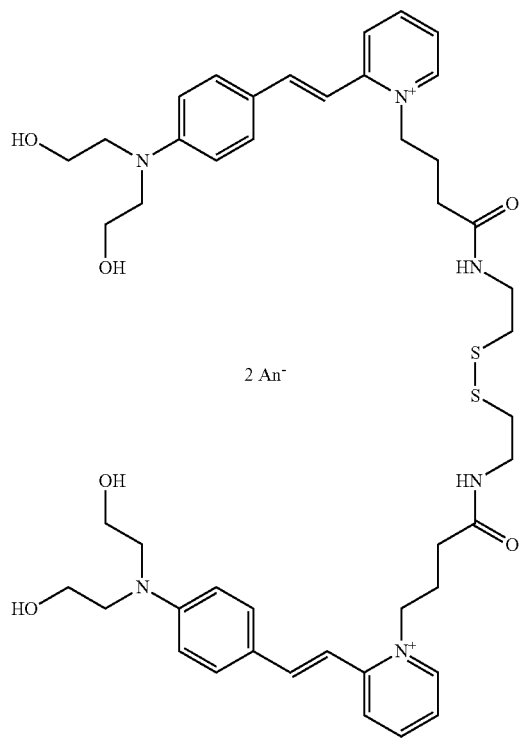

25 with An⁻ and M', which may be identical or different, preferentially identical, representing anionic counterions. More particularly, the anionic counterion is chosen from halides such as chloride, alkyl sulfates such as methyl sulfate, and mesylate.

Preparation of the Compounds (I)

The dyes of formula (I) may be synthesized via a condensation reaction between a compound (a1) and a compound (a2). This reaction is well known to those skilled in the art. It is known as the Knoevenagel reaction and consists in condensing an aldehyde with a nucleophile of activated methyl type. This reaction is described in the literature. Reference may be made, for example, to the book *Advanced Organic Chemistry* (ISBN 0-471-60180-2). This reaction is illustrated in the scheme below:

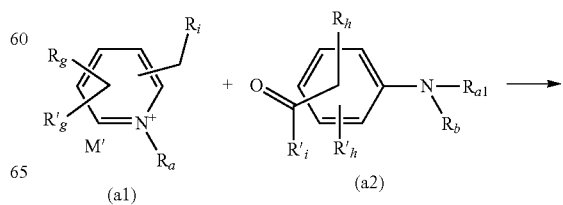

-continued

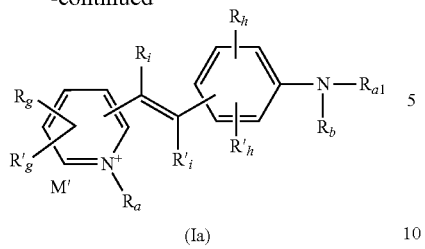

(Ia)

with $R_{a1}$, $R_a$, $R_b$, $R_g$, $R'_g$, $R_i$, $R'_i$, $R_h$, $R'_h$, M' and q as defined previously.

Compounds (a1) are known to those skilled in the art and are described in the literature. Some of them are commercially available.

Compounds (a2) may be synthesized via a nucleophilic substitution reaction between a compound (a3) and a compound (a4). This reaction is known to those skilled in the art and is described in the literature. By way of example, reference may be made to the book *Advanced Organic Chemistry* (ISBN 0-471-60180-2). This reaction is illustrated in the scheme below:

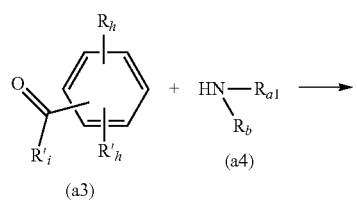

(a3)       (a4)

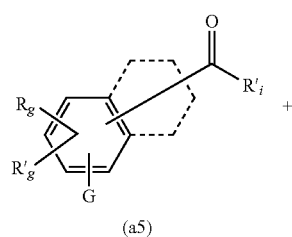

(a2)

with $R_{a1}$, $R_b$, $R_i$, $R'_i$, $R_h$ and $R'_h$ as defined previously and Hal represents a halogen atom such as fluorine.

Compounds (a3) and (a4) are known to those skilled in the art. Some of them are commercially available.

The dyes of formula (Ib) may be synthesized via a condensation reaction between a compound (a5) and a compound (a6). This reaction is well known to those skilled in the art, and is known as the Knoevenagel reaction, which consists in condensing an aldehyde with a nucleophile of activated methyl type. This reaction is illustrated in the scheme below:

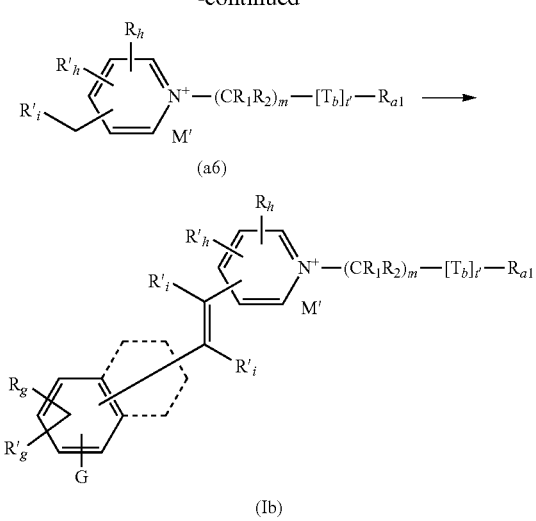

(a5)

-continued

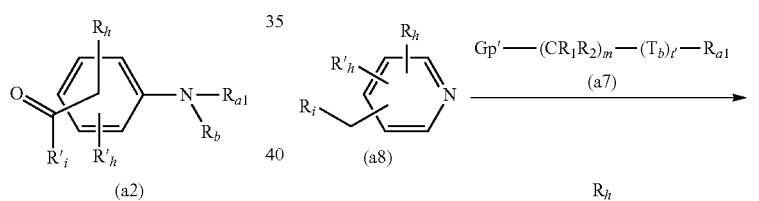

(a6)

(Ib)

with G, $R_{a1}$, $R_a$, $R_b$, $R_i$, $R'_i$, $R_h$, $R'_h$, $T_b$, t and M' as defined previously.

Compounds (a5) are known to those skilled in the art and are described in the literature. Some of them are commercially available.

Compounds (a6) may be synthesized via a quaternization reaction between an electrophilic compound (a7) and a pyridine compound (a8). This reaction is well known to those skilled in the art.

(a8)

(a6)

with G, $R_{a1}$, $R_a$, $R_b$, $R_i$, $R'_i$, $R_h$, $R'_h$, $T_b$, t and M' as defined previously;

with $R_1$, $R_2$, $R_{a1}$, $R_a$, $R_b$, $R_g$, $R'_g$, $R_i$, $R'_i$, $R_h$, $R'_h$, $T_b$, t, m and M' as defined previously.

The group Gp' represents a leaving group, which, once it has left, generates an anionic counterion. Mention may be made of halides such as iodide, bromide, chloride or the mesylate, sulfate, phosphate, triflate or tosylate group.

Compounds (a7) and (a8) are known to those skilled in the art. Some of them are commercially available.

The dyes of formula (Ic) may be synthesized via the synthetic routes described previously for the dyes of formula (Ia). The main difference is that compounds (a9), compounds bearing an indolinium unit, are used instead of compounds (a1), compounds bearing a pyridinium unit. The reaction with compounds (a2) is illustrated in the scheme below:

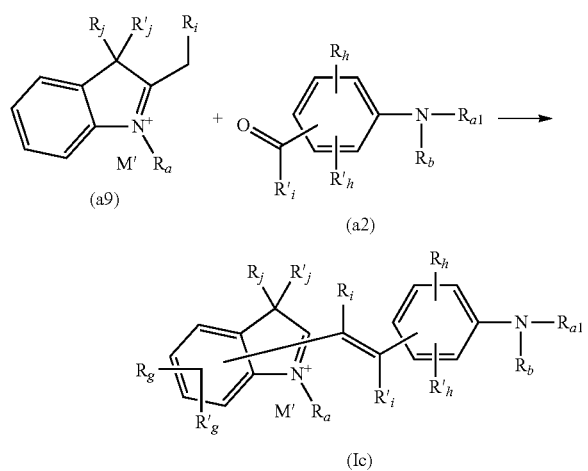

(a9) + (a2) → (Ic)

with $R_{a1}$, $R_a$, $R_b$, $R_g$, $R'_g$, $R_i$, $R'_i$, $R_h$, $R'_h$, $T_b$, t and M' as defined previously.

Compounds (a9) are known to those skilled in the art and are described in the literature. Some of them are commercially available.

Compounds (Id) may be synthesized via a reaction between a compound (a10) and a compound (a11). This reaction is illustrated in the scheme below:

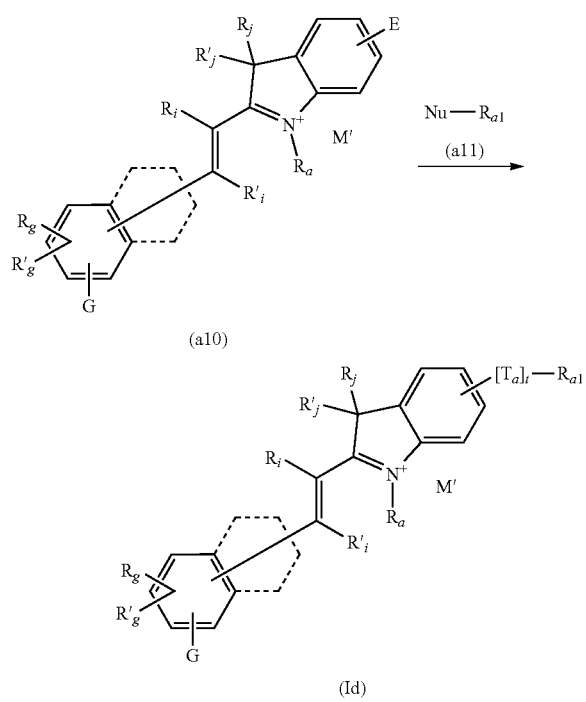

(a10) + Nu—$R_{a1}$ (a11) → (Id)

with G, $R_{a1}$, $R_a$, $R_b$, $R_g$, $R'_g$, $R_i$, $R'_i$, $R_h$, $R'_h$, t and M' as defined previously; Nu representing a nucleophilic group; E representing an electrophilic group; and $T_a$ the bond generated after attack of the nucleophile on the electrophile. By way of example, the covalent bonds $T_a$ that may be generated are listed in Table A, starting with condensation of electrophiles with nucleophiles:

TABLE A

| Electrophiles E | Nucleophiles Nu | Covalent bonds $T_a$ |
|---|---|---|
| Activated esters* | Amines | Carboxamides |
| Acyl azides** | Amines | Carboxamides |
| Acyl halides | Amines | Carboxamides |
| Acyl halides | Alcohols | Esters |
| Acyl cyanides | Alcohols | Esters |
| Acyl cyanides | Amines | Carboxamides |
| Alkyl halides | Amines | Alkylamines |
| Alkyl halides | Carboxylic acids | Esters |
| Alkyl halides | Thiols | Thioesters |
| Alkyl halides | Alcohols | Ethers |
| Sulfonic acids and salts thereof | Thiols | Thioethers |
| Sulfonic acids and salts thereof | Carboxylic acids | Esters |
| Sulfonic acids and salts thereof | Alcohols | Ethers |
| Anhydrides | Alcohols | Esters |
| Anhydrides | Amines | Carboxamides |
| Aryl halides | Thiols | Thioethers |
| Aryl halides | Amines | Arylamines |
| Aziridines | Thiols | Thioethers |
| Carboxylic acids | Amines | Carboxamides |
| Carboxylic acids | Alcohols | Esters |
| Carbodiimides | Carboxylic acids | N-Acylureas or anhydrides |
| Diazoalkanes | Carboxylic acids | Esters |
| Epoxides | Thiols | Thioethers |
| Haloacetamides | Thiols | Thioethers |
| Imide esters | Amines | Amidines |
| Isocyanates | Amines | Ureas |
| Isocyanates | Alcohols | Urethanes |
| Isothiocyanates | Amines | Thioureas |
| Maleimides | Thiols | Thioethers |
| Sulfonic esters | Amines | Alkylamines |
| Sulfonic esters | Thiols | Thioethers |
| Sulfonic esters | Carboxylic acids | Esters |
| Sulfonic esters | Alcohols | Ethers |
| Sulfonyl halides | Amines | Sulfonamides |

*the activated esters of general formula —CO-Part with Part representing a leaving group such as optionally substituted oxysuccinimidyl, oxybenzotriazolyl or aryloxy;
**the acyl halides may rearrange to give isocyanates.

These reactions are known to those skilled in the art and are described in the literature. Reference may be made to the book *Advanced Organic Chemistry* (ISBN 0-471-60180-2).

Compounds (a11) are known to those skilled in the art and are described in the literature. Some of them are commercially available.

Compounds (a10) may be synthesized via a reaction between an indolinium derivative (a12) and a compound bearing a carbonyl group (a5). This reaction is illustrated in the scheme below:

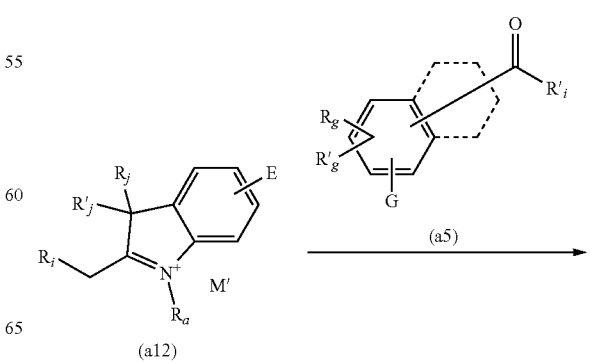

(a12) + (a5) →

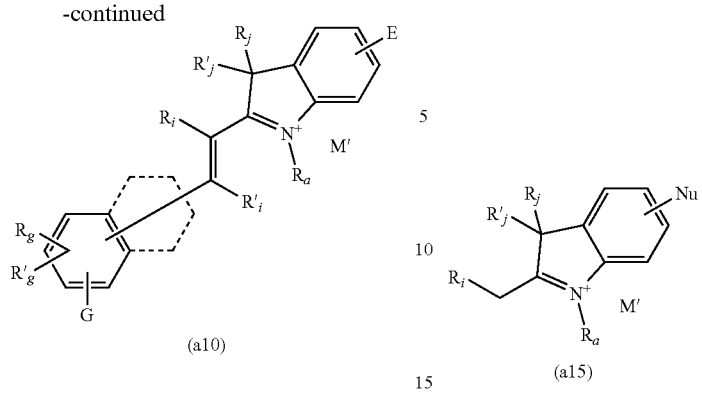

(a10)

with G, $R_{a1}$, $R_a$, $R_b$, $R_g$, $R'_g$, $R_i$, $R'_i$, $R_h$, $R'_h$, $T_b$, t, E, Nu and M' as defined previously.

Compounds (a12) are known to those skilled in the art and are described in the literature. Some of them are commercially available. Compounds (a5) are as described previously.

Alternatively, compounds (Id) may be synthesized via a reaction between a compound (a13) and a compound (a14). This reaction is illustrated in the scheme below:

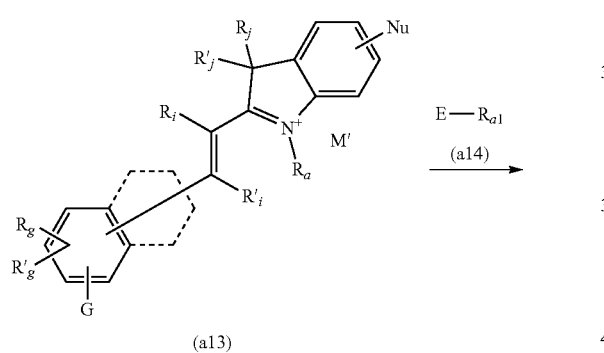

with G, $R_{a1}$, $R_a$, $R_b$, $R_g$, $R'_g$, $R_i$, $R'_i$, $R_h$, $R'_h$, $T_b$, t, E, Nu and M' as defined previously.

Compounds (a14) are known to those skilled in the art and are described in the literature. Some of them are commercially available.

Compounds (a13) may be synthesized via a reaction between a compound (a35) and a compound (a23). This reaction is illustrated by the scheme below:

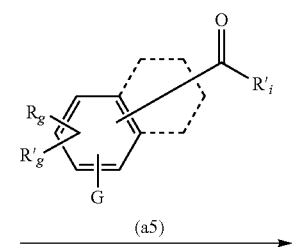

(a15)     (a5)

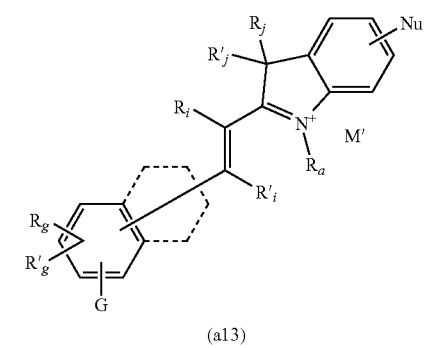

(a13)

with $R_a$, G, Nu, $R_g$, $R'_g$, $R_i$, $R'_i$, $R_j$, $R'_j$ and M' as defined previously.

Compounds (a15) are known to those skilled in the art and are described in the literature. Some of them are commercially available. Compounds (a5) are as described previously.

Compounds (Ie) may be synthesized via a reaction between a compound (a16) and a compound (a17). This reaction is well known to those skilled in the art. It is an alkylation reaction. This reaction is described in the literature. Reference may be made, for example, to the book *Advanced Organic Chemistry* (ISBN 0-471-60180-2). This reaction is illustrated in the scheme below:

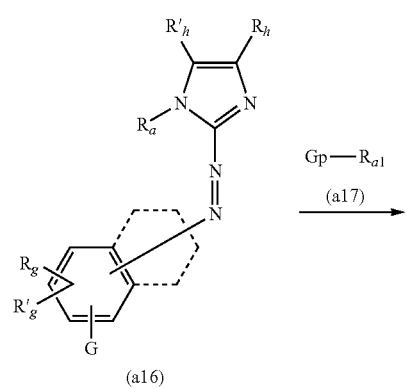

(a16)

-continued

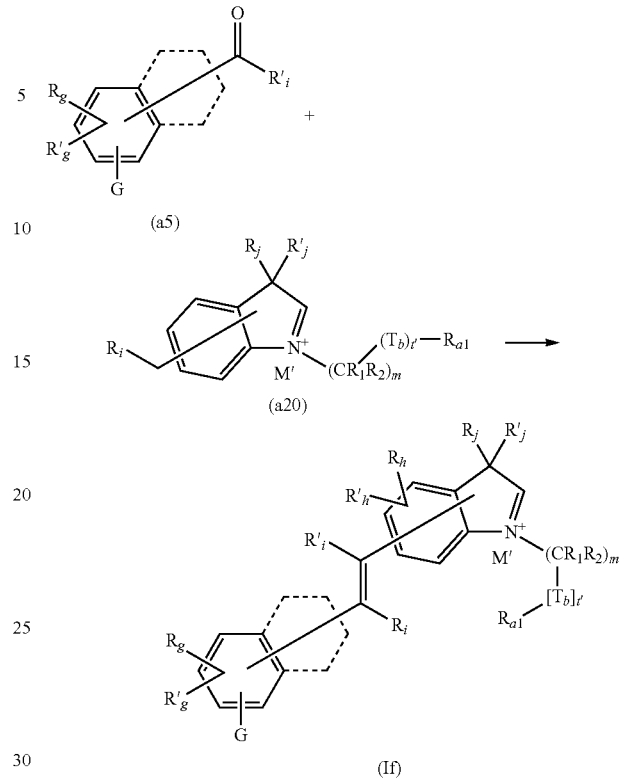

(Ie)

with G, $G_p$, $R_{a1}$, $R_a$, $R_g$, $R'_g$, $R_h$, $R'_h$ and M' as defined previously.

Compounds (a17) are known to those skilled in the art and are described in the literature. Some of them are commercially available.

Compounds (a16) may be synthesized via a reaction between a compound (a18) and a compound (a19). This reaction is well known to those skilled in the art. It is a diazotization and coupling reaction. This reaction is described in the literature. Reference may be made, for example, to the book *Advanced Organic Chemistry* (ISBN 0-471-60180-2). This reaction is illustrated by the scheme below:

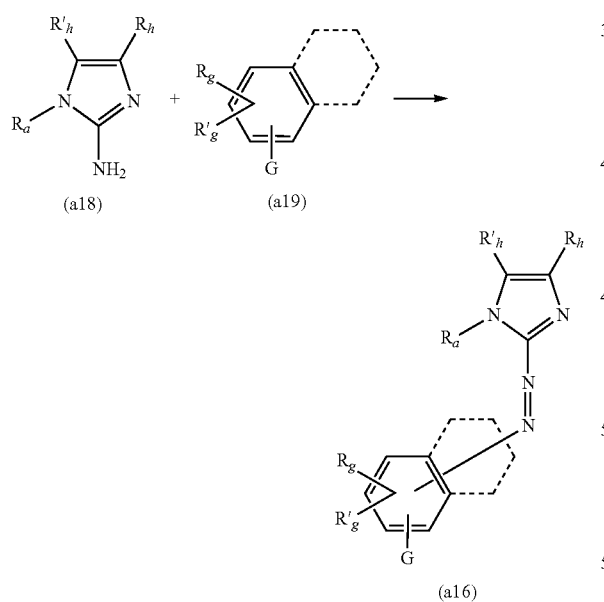

with G, $R_{a1}$, $R_a$, $R_b$, $R_g$, $R'_g$, $R_h$, $R'_h$ and M' as defined previously.

Compounds (a18) and (a19) are known to those skilled in the art and are described in the literature. Some of them are commercially available.

Compounds (If) may be synthesized via a reaction between a compound (a5) and a compound (a20). This reaction is illustrated in the scheme below:

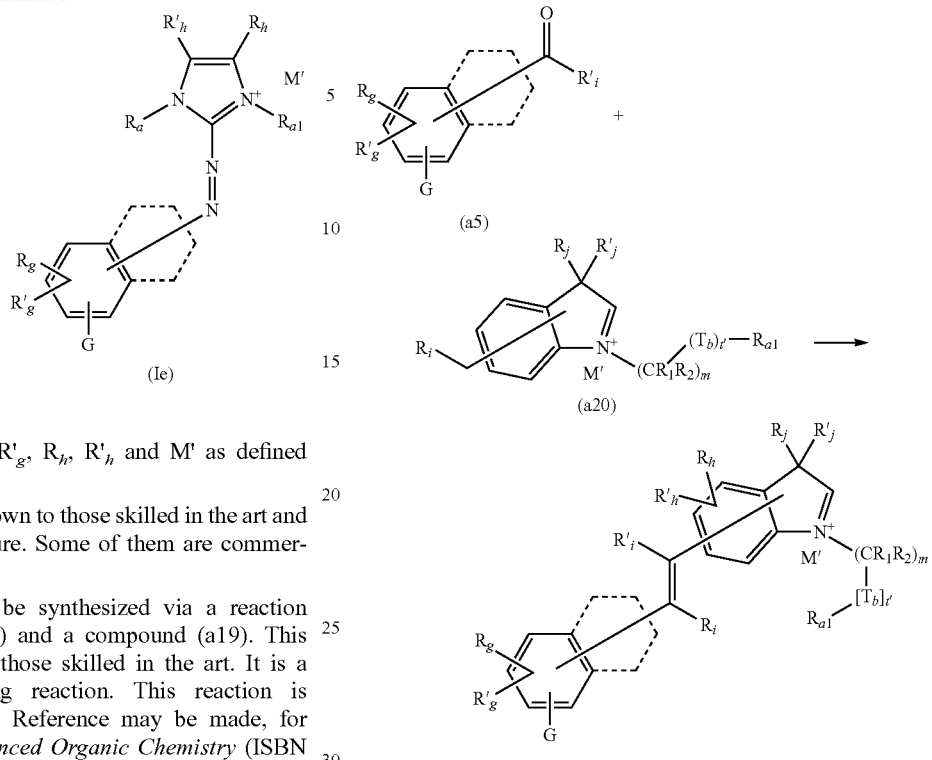

with G, $R_{a1}$, $R_a$, $R_b$, $R_g$, $R'_g$, $R_i$, $R'_i$, $R_h$, $R'_h$, $R_j$, $R'_j$, $T_b$, m, t' and M' as defined previously.

Compounds (a5) are as described previously.

Compounds (a20) may be synthesized via a reaction between a compound (a21) and a compound (a22). This reaction is illustrated in the scheme below:

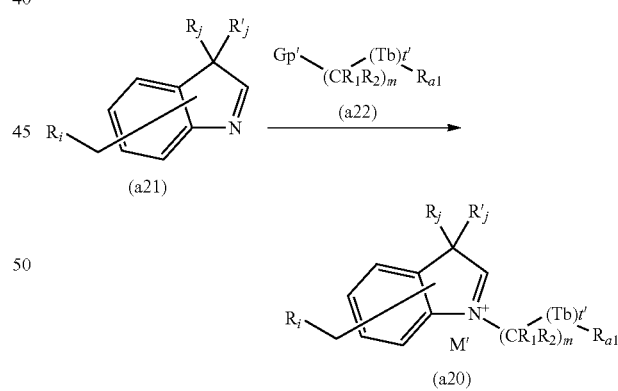

with $R_1$, $R_2$, $R_{a1}$, G, m, Tb, t', $R_i$, $R'_i$, $R_j$, $R'_j$ and M' as defined previously.

The group Gp' represents a leaving group, which, once it has been removed, will generate an anionic counterion M'. Mention may be made of halides such as iodide, bromide, chloride or the triflate, sulfate, phosphate, mesylate or tosylate group.

Compounds (a21) and (a22) are known to those skilled in the art and some of them are commercially available.

Compounds (Ig) may be synthesized via a reaction between a compound (a23) and a compound (a17). This reaction is well known to those skilled in the art. It is a quaternization reaction. This reaction is described in the literature. Reference may be made, for example, to the book *Advanced Organic Chemistry* (ISBN 0-471-60180-2). This reaction is illustrated in the scheme below:

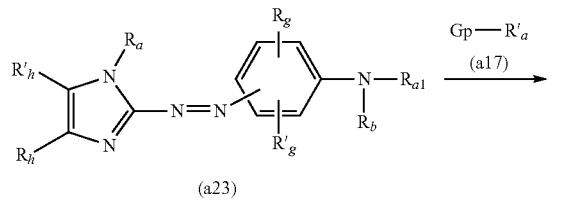

(a23)

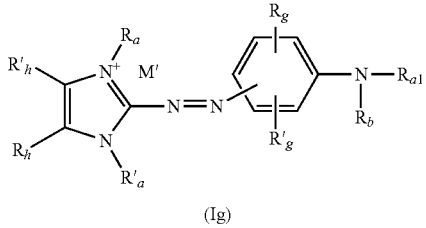

(Ig)

with $R_{a1}$, $R_a$, $R'_a$, $R_b$, $R_g$, $R'_g$, $R_h$, $R'_h$, $G_p$ and M' as defined previously.

Compounds (a17) are known to those skilled in the art and are described in the literature. Some of them are commercially available.

Compounds (a23) may be synthesized via a reaction between a compound (a35) and a compound (a23). This reaction is well known to those skilled in the art. It is known as a diazotization and coupling reaction. This reaction is described in the literature. Reference may be made, for example, to the book *Advanced Organic Chemistry* (ISBN 0-471-60180-2). This reaction is illustrated by the scheme below:

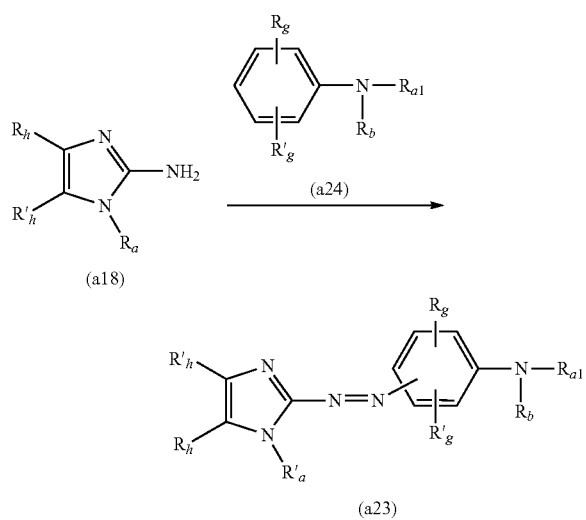

(a23)

with $R_{a1}$, $R_a$, $R'_a$, $R_b$, $R_g$, $R'_g$, $R_h$ and $R'_h$ as defined previously.

Compounds (a18) are known to those skilled in the art and some of them are commercially available.

Compounds (a24) may be synthesized via a reaction between a compound (a17) and a compound (a25). This reaction is well known to those skilled in the art. It is an alkylation reaction. This reaction is described in the literature. Reference may be made, for example, to the book *Advanced Organic Chemistry* (ISBN 0-471-60180-2). This reaction is illustrated in the scheme below:

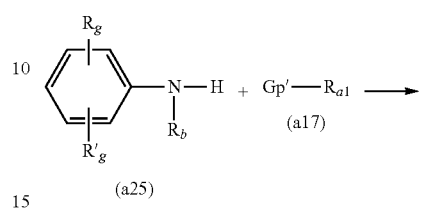

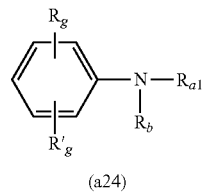

(a24)

with $G_p$, $R_{a1}$, $R_b$, $R_g$, $R'_g$ and M' as defined previously.

Compounds (Ih) may be synthesized via a reaction between a compound (h) and a compound (h). This reaction is known to those skilled in the art and is described in the literature. Reference may be made, for example, to the book *Advanced Organic Chemistry* (ISBN 0-471-60180-2). This reaction is illustrated in the scheme below:

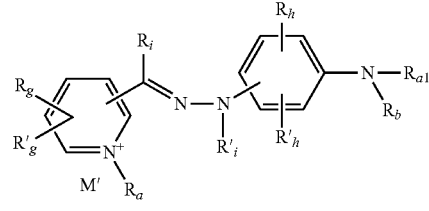

(Ih)

with $R_{a1}$, $R_a$, $R_b$, $R_g$, $R'_g$, $R_i$, $R'_i$, $R_h$, $R'_h$ and M' as defined previously.

Compounds (a26) and (a27) are known to those skilled in the art and some of them are commercially available.

Compounds (Ii) may be synthesized via a reaction between a compound (h) and a compound (h). This reaction is well known to those skilled in the art and is described in the literature. Reference may be made, for example, to the book *Advanced Organic Chemistry* (ISBN 0-471-60180-2). This reaction is illustrated in the scheme below:

(a28)

(a29)

(Ii)

with G, $R_{a1}$, $R_g$, $R'_g$, $R_i$, $R'_i$, $R_h$, $R'_h$ and M' as defined previously.

Compounds (a28) are known to those skilled in the art and some of them are commercially available.

Compounds (a29) may be synthesized via a reaction between a compound (a30) and a compound (a17).

(a30) → (a29)

with $G_{p'}$, $R_{a1}$, $R'_i$, $R_h$, $R'_h$ and M' as defined previously.

Compounds (a30) are known to those skilled in the art and some of them are commercially available. Compounds (a17) are described above.

Compounds (Ij) may be synthesized via a reaction between a compound (h) and a compound (h). This reaction is well known to those skilled in the art and is described in the literature. Reference may be made, for example, to the book *Advanced Organic Chemistry* (ISBN 0-471-60180-2). This reaction is illustrated in the scheme below:

(a31)

(Ij)

with $G_{p'}$, $R_s$, $R_{a1}$, $R_b$, $R_g$, $R'_g$, $R_h$, $R'_h$ and M' as defined previously.

Compounds (a31) are known to those skilled in the art and some of them are commercially available. Compounds (a17) are described above.

Alternatively, compounds (Ij) may be synthesized via a reaction between a compound (a4) and a compound (a32). This reaction is well known to those skilled in the art and is described in the literature. Reference may be made, for example, to the book *Advanced Organic Chemistry* (ISBN 0-471-60180-2). This reaction is illustrated in the scheme below:

(a32)

(Ij)

with G, $R_s$, $R_{a1}$, $R_b$, $R_g$, $R'_g$, $R_h$, $R'_h$ and M' as defined previously and Hal as defined previously, preferentially a bromine atom.

Compounds (a32) are known to those skilled in the art and some of them are commercially available. Compounds (a4) are described above.

Compounds (Ik) may be synthesized via a reaction between a compound (a24) and a compound (a33). This reaction is well known to those skilled in the art and is described in the literature. It is a diazotization and coupling reaction. Reference may be made, for example, to the book *Advanced Organic Chemistry* (ISBN 0-471-60180-2). This reaction is illustrated in the scheme below:

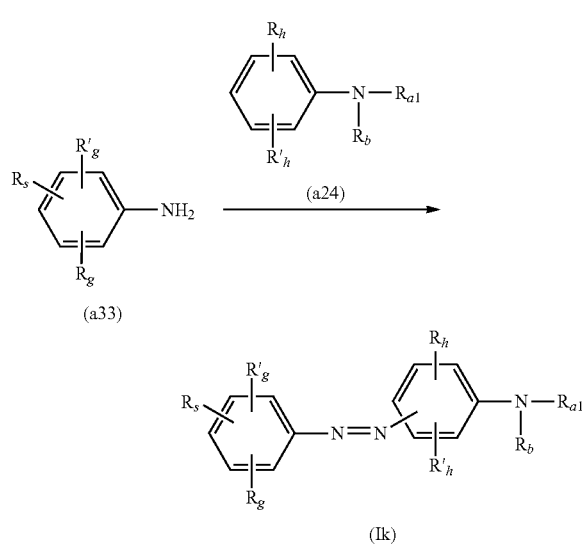

with $R_{a1}$, $R_s$, $R_b$, $R_g$, $R'_g$, $R_h$, $R'_h$ and M' as defined previously.

Compounds (a24) and (a33) are known to those skilled in the art and some of them are commercially available.

Compounds (II) may be synthesized via a reaction between a compound (a34) and a compound (a35). This reaction is well known to those skilled in the art and is described in the literature. It is a diazotization and coupling reaction. Reference may be made, for example, to the book *Advanced Organic Chemistry* (ISBN 0-471-60180-2). This reaction is illustrated in the scheme below:

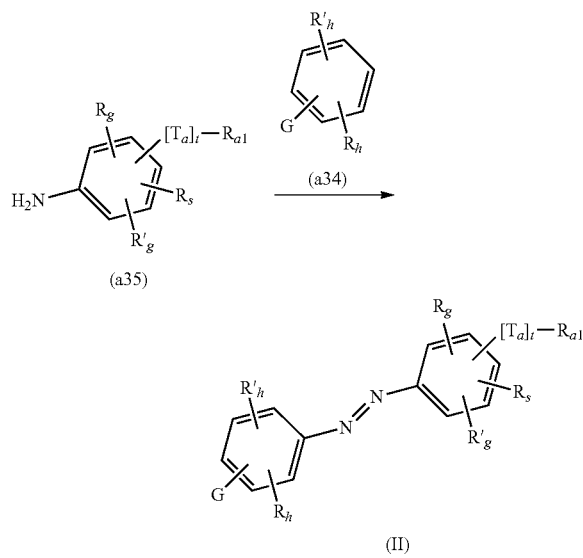

with G, $R_s$, $R_{a1}$, $R_a$, $R_b$, $R_g$, $R'_g$, $R_h$, $R'_h$, $T_b$, t and M' as defined previously.

Compounds (a34) and (a34) are known to those skilled in the art and some of them are commercially available.

The direct thiol, protected thiol or disulfide dyes of formula (I) that are useful in the present invention are known compounds and may be prepared according to methods known to those skilled in the art, especially from the methods described in patent applications EP 1 647 580, EP 2 004 759, WO 2007/110 541, WO 2007/110 540, WO 2007/110 539, WO 2007/110 538, WO 2007/110 537, WO 2007/110 536, WO 2007/110 535, WO 2007/110 534, WO 2007/110 533, WO 2007/110 532, WO 2007/110 531, EP 2 070 988 and WO 2009/040 354.

1.c) Pigments

According to a particular embodiment of the invention, the ingredient(s) i) are chosen from pigments. The term "pigments" means organic or mineral dyes, which dye chromatically or achromatically (preferably chromatically), and which are insoluble or virtually insoluble in the cosmetic medium. In contrast, dyes, in particular direct dyes, are soluble in the cosmetic medium (*Ullmann's Encyclopedia of Industrial Chemistry*, "pigments", 2012 Wiley-VCH Verlag GmbH & Co. KGaA, Weinheim, DOI: 10.1002/14356007.a20_371; vol. 27, K. Hunger, W. Herbst, p. 380).

The pigments that are useful in the present invention may be in the form of powder or of pigmentary paste.

In the context of the invention, the pigment comprising at least one organic part is a pigment which may be totally organic or which may comprise an organic part and another part such as a mineral part.

According to a preferred embodiment, the pigment is an organic pigment, i.e. it comprises at least one organic part and/or a photoreactive or photolabile group as defined previously.

The term "organic pigment" means any pigment that satisfies the definition in Ullmann's encyclopaedia in the chapter on organic pigments (K. Hunger, W. Herbst, *Ullmann's Encyclopedia of Industrial Chemistry*, "Pigments, Organic", 2012 Wiley-VCH Verlag GmbH & Co. KGaA, Weinheim, DOI: 10.1002/14356007.a20_371; vol. 27, pp. 379-423; W. Herbst, K. Hunger, G. Wilker: *Industrial organic pigments*, 3, compl. rev. ed., Wiley-VCH, Weinheim 2004; E. E. Jaffe; *Kirk Othmer Encyclopedia of Chemical Technology*, "Pigments, Organic", 5th edition, vol. 19, pp. 417-456, John Wiley & Sons, Hoboken, N.J., 2006, online: DOI: 10.1002/0471238961.151807011001060605.a01.pub2). The organic pigment may especially be chosen from nitroso, nitro, azo, xanthene, quinoline, anthraquinone, phthalocyanin, metal complex, isoindolinone, isoindoline, quinacridone, perinone, perylene, porphyrin, diketopyrrolopyrrole, thioindigo, dioxazine, triphenylmethane and quinophthalone compounds.

The organic pigment(s) may be chosen, for example, from carmine, carbon black, aniline black, azo yellow, quinacridone, phthalocyanin blue, sorghum red, the blue pigments codified in the Color Index under the references CI 42090, 69800, 69825, 73000, 74100 and 74160, the yellow pigments codified in the Color Index under the references CI 11680, 11710, 15985, 19140, 20040, 21100, 21108, 47000 and 47005, the green pigments codified in the Color Index under the references CI 61565, 61570 and 74260, the orange pigments codified in the Color Index under the references CI 11725, 15510, 45370 and 71105, the red pigments codified in the Color Index under the references CI 12085, 12120, 12370, 12420, 12490, 14700, 15525, 15580, 15620, 15630, 15800, 15850, 15865, 15880, 17200, 26100, 45380, 45410, 58000, 73360, 73915 and 75470, and the pigments obtained by oxidative polymerization of indole or phenolic derivatives as described in patent FR 2 679 771.

The pigment comprising at least one organic part may also be a pigmentary paste formed from organic pigments, such as the products sold by the company Hoechst under the names: Cosmenyl Yellow IOG: Pigment Yellow 3 (CI 11710); Cosmenyl Yellow G: Pigment Yellow 1 (CI 11680);

Cosmenyl Orange GR: Pigment Orange 43 (CI 71105); Cosmenyl Red R": Pigment Red 4 (CI 12085); Cosmenyl Carmine FB: Pigment Red 5 (CI 12490); Cosmenyl Violet RL: Pigment Violet 23 (CI 51319); Cosmenyl Blue A2R: Pigment Blue 15.1 (CI 74160); Cosmenyl Green GG: Pigment Green 7 (CI 74260); Cosmenyl Black R Pigment Black 7 (CI 77266).

The pigment comprising at least one organic part may also be in the form of composite pigments, as are described in patent EP 1 184 426. This composite pigment may be composed in particular of particles comprising a mineral core, at least one binder for attaching the organic pigments to the core, and at least one organic pigment which at least partially covers the core. Such pigments are described, for example, in patent application EP 1 184 426.

The pigment comprising at least one organic part may also be a lake consisting of mineral substrates onto which are adsorbed organic pigments. The mineral substrates are, for example, alumina, silica, calcium sodium borosilicate, calcium aluminium borosilicate and aluminium. Among the organic dyes, mention may be made of cochineal carmine.

Examples of lakes that may be mentioned include the products known under the following names: D & C Red 21 (CI 45 380), D & C Orange 5 (CI 45 370), D & C Red 27 (CI 45 410), D & C Orange 10 (CI 45 425), D & C Red 3 (CI 45 430), D & C Red 7 (CI 15 850:1), D & C Red 4 (CI 15 510), D & C Red 33 (CI 17 200), D & C Yellow 5 (CI 19 140), D & C Yellow 6 (CI 15 985), D & C Green (CI 61 570), D & C Yellow 1 O (CI 77 002), D & C Green 3 (CI 42 053) or D & C Blue 1 (CI 42 090).

As pigments comprising at least one organic part, mention may also be made of nacreous pigments of titanium mica type covered with an organic pigment of the abovementioned type.

According to one particular embodiment, the pigments are coloured pigments. The term "coloured pigments" means pigments other than white pigments.

The size of the pigment that is useful in the context of the present invention is generally between 10 nm and 200 μm, preferably between 20 nm and 80 μm and more preferentially between 30 nm and 50 μm.

The pigment(s) comprising an organic part are each generally present in the composition in accordance with the invention in amounts generally between 0.05% and 50% and preferably from 0.1% to 35% of the total weight of the composition.

2. Photoactive Compounds:

The second ingredient ii) used in the process of the invention is a photoactive compound.

The term "photoactive compound", also known as PACs or photoinitiators (PIs), means a compound that is capable of absorbing light and of becoming transformed, generating atoms or molecules comprising free-radical chemical reactivity (see, for example, *Macromol. Rapid Commun.* Christian Decker, 23, 1067-1093 (2002); *Encyclopedia of Polymer Science and Technology*, "photopolymerisation free radical" http://onlinelibrary.wiley.com/doi/10.1002/0471440264.pst490/pdf; ibid, "photopolymerisation, cationic", http://onlinelibrary.wiley.com/doi/10.1002/0471440264.pst491/pdf; *Macromol. Symp.* 143, 45-63 (1999)). These photoactive compounds are not chemical oxidizing agents such as peroxides including hydrogen peroxide or systems for generating hydrogen peroxides. Two major families may be distinguished: that of type I in which the photoactive compounds bring about, under irradiation, a unimolecular cleavage of the covalent bond to give a free radical compound also symbolized by a "point", and of type II in which the photoactive compounds, under irradiation, lead to a bimolecular reaction in which the photoactive compounds in their excited state interact with a second molecule (or co-initiator) to generate free radicals.

More particularly, the active compound is chosen from the compounds of formula (VI), (VII), (VIII) or (IX) and also organic or mineral acid salts thereof, optical, geometric and tautomeric isomers thereof, and solvates thereof such as the hydrates:

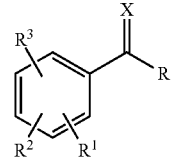

(VI)

(VII)

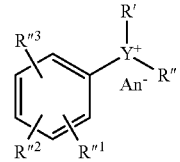

(VIII)

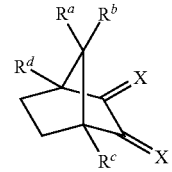

(IX)

in which formula (VI), (VII), (VIII) or (IX):

R represents a group chosen from:

i) $(C_1$-$C_{10})$alkyl, which is optionally substituted, preferably with one or more atoms or groups chosen from halogen, hydroxyl, $(C_1$-$C_{10})$alkoxy, 5- to 10-membered (hetero)cycloalkyl such as morpholinyl, and amino $R_a R_b N$— with $R_a$ and $R_b$, which may be identical or different, representing a hydrogen atom or a $(C_1$-$C_{10})$ alkyl group or alternatively $R_a$ and $R_b$ form, together with the nitrogen atom that bears them, a heteroaryl or heterocycloalkyl group such as morpholino;

ii) $(C_1$-$C_{10})$alkoxy, which is optionally substituted, preferably with the same substituents as for i) $(C_1$-$C_{10})$ alkyl;

iii) hydroxyl;

iv) optionally substituted (hetero)aryl such as optionally substituted phenyl of formula

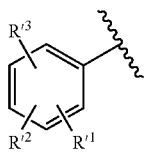

(X)

with R'¹, R'², R'³, which may be identical or different, being as defined for R¹, R², R³ and ╂ representing the point of attachment to the rest of the molecule;
v) (hetero)cycloalkyl, which is optionally substituted, preferably with a hydroxyl group;
vi) R⁴—(X)$_n$—C(X)—(X)$_{n'}$— with R⁴ representing an optionally substituted (C₁-C₁₀)alkyl, optionally substituted (hetero)aryl such as optionally substituted phenyl of formula (X), or optionally substituted (hetero)cycloalkyl group, n and n', which may be identical or different, being equal to 0 or 1;
vii) R$_c$R$_d$P(X)— with R$_c$ representing an optionally substituted (C₁-C₁₀)alkyl or optionally substituted (hetero) aryl group, and R$_d$ representing an optionally substituted (hetero)aryl group;
viii) or alternatively R¹ with R ortho to the group C(X)—R or R" and R'"¹ ortho to the group R'—Y⁺—R" form, together with the atoms that bear them, a (hetero) cycle fused to the phenyl or (hetero)aryl fused to the phenyl, optionally substituted, especially on the non-aromatic part, with one or more oxo or thioxo groups; preferably R¹ with R ortho to the group C(X)—R form, together with the atoms that bear them and the fused phenyl ring, an anthraquinone group (XI):

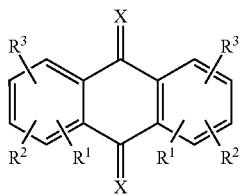

(XI)

R¹, R² or R³, which may be identical or different, represent i) a hydrogen atom, ii) a halogen atom such as chlorine, iii) an optionally substituted (C₁-C₁₀)alkyl group, iv) (C₁-C₁₀)alkoxy optionally substituted especially with a hydroxyl group, v) optionally substituted (hetero)aryl, vi) optionally substituted (hetero)cycloalkyl, vii) carboxyl, viii) cyano, ix) nitro, x) nitroso, xi) —S(O)$_p$—OM with p equal to 1 or 2, M representing a hydrogen atom or an alkali metal or alkaline-earth metal, xii) R⁴R⁵N—; xiii) R⁴—(X)$_n$—C(X)—(X)$_{n'}$— with R⁴, n and n' as defined previously, R⁵ is as defined for R⁴ or alternatively R⁴ and R⁵ form, together with the nitrogen atom that bears them, an optionally substituted heterocycloalkyl or heteroaryl such as morpholino, which may be identical or different, being equal to 0 or 1, xiv) hydroxyl, or xv) thiol;
R'''¹, R'''² or R'''³, which may be identical or different, are as defined for R¹, R² and R³, are preferably chosen from a hydrogen atom or R⁴—Y— with R⁴ being as defined previously and preferably a phenyl group;
or alternatively contiguous R and R¹ form, together with the carbon atoms that bear them, an optionally unsaturated and optionally substituted (hetero)cycloalkyl group, preferably cycloalkyl that is optionally substituted in particular with one or more oxo groups and/or optionally fused with an aryl group such as benzo;
or alternatively two contiguous substituents R¹, R² and/or R'¹, R'² together form a group derived from maleic anhydride such as —C(X)—X—C(X)—;
X, which may be identical or different, represents an oxygen or sulfur atom or a group NR⁵ with R⁵ as defined previously, preferably representing a hydrogen atom or a (C₁-C₁₀)alkyl group; more particularly, X represents an oxygen atom;
Y is as defined for X, and preferably Y represents a sulfur atom;
Metal represents a transition metal such as iron or chromium, preferably Fe, said metal possibly being cationic, in which case the photoactive compound of formula (XVIII) comprises a number of anionic counterions An⁻ as defined previously, for affording the molecule electrical neutrality;
L and L', which may be identical or different, representing a transition metal ligand preferably chosen from the following electron donors C(X) with X as defined previously, cyano CN, (C₁-C₆)alkenyl, optionally substituted (hetero)aryl such as bipyridyl, amines such as the amines R⁴R⁵R⁶N with R⁴ and R⁵ as defined previously and R⁶ representing a hydrogen atom, or a group as defined for R⁴, phosphine R⁴R⁵R⁶P such as tri(hetero)arylphosphine, (hetero)cycloalkyl which is preferably unsaturated, such as cyclopentadiene, carbene such as arduengo carbenes,
q representing an integer inclusively between 1 and 6, for affording the metal complex stability, i.e. so as to obtain an electron number around the Metal equal to 16 or 18 electrons (it is also referred to as a coordination sphere with 16 or 18 electrons);
R' and R", which may be identical or different, represent an optionally substituted (hetero)aryl group;
An⁻ represents an anionic counterion as defined previously, preferably chosen from (Hal)₆P⁻' or (Hal)₆Sb⁻' with Hal, which may be identical or different, representing a halogen atom such as fluorine; and
R$^a$, R$^b$, R$^c$ or R$^d$, which may be identical or different, represent a hydrogen atom or a (C₁-C₁₀)alkyl group.
According to one preferred embodiment of the invention, the photoactive compound(s) are chosen from the following compounds:

| Designation | CAS No. |
|---|---|
| Benzophenone | 0000119-61-9 |
| Benzophenone, 2-methyl- | 0000131-58-8 |
| Benzophenone, 4-methyl- | 0000134-84-9 |
| Benzoic acid, 2-benzoyl-, methyl ester | 0000606-28-0 |
| Benzophenone, 3-methyl- | 0000643-65-2 |
| 2-Isopropylthioxanthone | 0005495-84-1 |
| Benzoic acid, 4-(dimethylamino)-, ethyl ester | 0010287-53-3 |
| Benzoic acid, p-(dimethylamino)-, 2-ethylhexyl ester | 0021245-02-3 |
| Poly(ethylene glycol) bis(p-dimethylaminobenzoate) | 0071512-90-8 |
| Phosphine oxide, diphenyl(2,4,6-trimethylbenzoyl)- | 0075980-60-8 |
| 4-Isopropylthioxanthone | 0083846-86-0 |
| 1-[4-(2-Hydroxyethoxy)phenyl]-2-hydroxy-2-methyl-1-propan-1-one | 0106797-53-9 |
| 1-Butanone, 2-(dimethylamino)-1-[4-(4-morpholinyl)phenyl]-2-(phenylmethyl)- | 0119313-12-1 |
| 1-Butanone, 2-(dimethylamino)-2-[(4-methylphenyl)methyl]-1-[4-(4-morpholinyl)phenyl]- | 0119344-86-4 |
| Phenyl bis(2,4,6-trimethylbenzoyl) phosphine oxide | 0162881-26-7 |

| Designation | CAS No. |
| --- | --- |
| Benzene, (1-methylethenyl)-, homopolymer, ar-(2-hydroxy-2-methyl-1-oxopropyl) derivs. | 0163702-01-0 |
| Oxyphenylacetic acid 2-[2-oxo-2-phenylacetoxyethoxy]ethyl ester | 0211510-16-6 |
| Oxyphenylacetic 2-[2-hydroxyethoxy]ethyl ester | 0442536-99-4 |
| Poly[oxy(methyl-1,2-ethanediyl)], α-[4-(dimethylamino)benzoyl-ω-butoxy | 0223463-45-4 |
| 1-(4-[(4-Benzoylphenyl)thio]phenyl)-2-methyl-2-[(4-methylphenyl)sulfonyl]-1-propan-1-one | 0272460-97-6 |
| 2-Hydroxy-1-(4-(4-(2-hydroxy-2-methylpropionyl)benzyl)phenyl)-2-methyl-2-propanone | 0474510-57-1 |
| Diester of carboxymethoxybenzophenone and polytetramethylene glycol 250 | 0515136-48-8 |
| Diester of carboxymethoxybenzophenone and polyethylene glycol 200 | 0515136-49-9 |
| Poly(oxy-1,4-butanediyl), α-[2-[(9-oxo-9H-thioxanthenyl)oxy]acetyl]-ω-[[2-[(9-oxo-9H-thioxanthenyl)oxy]acetyl]oxy]- | 0813452-37-8 |
| 4-(2-Hydroxyethoxy)phenyl-(2-hydroxy-2-propyl) ketone | 0106797-53-9 |

| Designation | CAS No. |
| --- | --- |
| (Methylamino)diethane-2,1-diylbis(4-dimethylamino amino benzoate) | |
| Riboflavin | |
| Anthraquinone, 2-ethyl- | 0000084-51-5 |
| Thioxanthen-9-one, 2-chloro- | 0000086-39-5 |
| Benzophenone, 4,4'-bis(diethylamino)- | 0000090-93-7 |
| Phosphine oxide, triphenyl- | 0000791-28-6 |
| Methanone, (1-hydroxycyclohexyl)phenyl- | 0000947-19-3 |
| Methanone, phenyl(2,4,6-trimethylphenyl)- | 0000954-16-5 |
| Glyoxylic acid, phenyl, ethyl ester | 0001603-79-8 |
| 4-Phenylbenzophenone | 0002128-93-0 |
| Benzoic acid, 2-(dimethylamino)ethyl ester | 0002208-05-1 |
| Acetophenone, 2,2-diethoxy- | 0006175-45-7 |
| 1H-Imidazole, 2-(2-chlorophenyl)-1-[2-(2-chlorophenyl)-4,5-diphenyl-2H-imidazol-2-yl]-4,5-diphenyl- | 0007189-82-4 |
| 1-Propanone, 2-hydroxy-2-methyl-1-phenyl- | 0007473-98-5 |
| d,I-Camphorquinone | 0010373-78-1 |
| Glyoxylic acid, phenyl-, methyl ester | 0015206-55-0 |
| 2,2-Dimethoxy-2-phenylacetophenone | 0024650-42-8 |
| Phenoxyethyl acrylate | 0048145-04-6 |
| Methyl 2-benzoylbenzoate | 0000606-28-0 |
| 2-Benzyl-2-(dimethylamino)-4-morpholinobutyrophenone | 0119313-12-1 |
| Ethyl 4-dimethylaminobenzoate | 0010287-53-3 |
| Iodonium, bis(4-methylphenyl)-, hexafluorophosphate(1-) | 0060565-88-0 |
| Bis(4-tert-butylphenyl)iodonium hexafluorophosphate | 0061358-25-6 |
| 1,2-Propanedione, 1-phenyl-, 2-[O-(ethoxycarbonyl)oxime] | 0065894-76-0 |
| Benzoic acid, 4-(dimethylamino)-, 2-butoxyethyl ester | 0067362-76-9 |
| Sulfonium, diphenyl[(phenylthio)phenyl]-, hexafluorophosphate(1-) (1:1) | 0068156-13-8 |
| 1-Propanone, 1-[4-(1,1-dimethylethyl)phenyl]-2-hydroxy-2-methyl- | 0068400-54-4 |
| Sulfonium, diphenyl[4-(phenylthio)phenyl]-, (OC-6-11)-hexafluoroantimonate(1-) (1:1) | 0071449-78-0 |
| Iodonium, bis(4-dodecylphenyl)-, (OC-6-11)-hexafluoroantimonate(1-)(1:1) | 0071786-70-4 |
| 1-Propanone, 2-methyl-1-[(4-methylthio)phenyl]-2-(4-morpholinyl)- | 0071868-10-5 |
| 1H-Azepine-1-propanoic acid, hexahydro-, 2,2-bis[[(1-oxo-2-propenyl)oxy]methyl]butyl ester | 0073003-78-8 |
| Bis(4-diphenylsulfonium)phenyl sulfide bis(hexafluorophosphate) | 0074227-35-3 |
| Diphenyl[(phenylthio)phenyl]sulfonium hexafluorophosphate | 0075482-18-7 |
| Anthracene, 9,10-dibutoxy | 0076275-14-4 |
| 2,4-Diethyl-9H-thioxanthen-9-one | 0082799-44-8 |
| 9H-Thioxanthene-2-carboxylic acid, 9-oxo-, ethyl ester | 0083817-60-1 |
| Methanone, [4-[(4-methylphenyl)thio]phenyl]phenyl- | 0083846-85-9 |
| Phosphinic acid, phenyl(2,4,6-trimethylbenzoyl)-, ethyl ester | 0084434-11-7 |
| Triphenylsulfonium hexafluorophosphate (mono+di)salts | 0086481-78-9 |
| Tryptophan | 000073-22-3 |
| Thiobis(4,1-phenylene)- S,S,S',S'-tetraphenyldisulfonium bishexafluoroantimonate | 0089452-37-9 |
| Triphenylsulfonium hexafluorophosphate | 0104558-95-4 |
| Bis (η-(5)-cyclopentadienyl)-bis(2,6-difluoro-3-[pyrrol-1-yl]-phenyl)titanium | 0125051-32-3 |
| 1-Chloro-4-propoxythioxanthone | 0142770-42-1 |
| Phosphine oxide, bis(2,6-dimethoxybenzoyl)(2,4,4-trimethylpentyl)-(9Cl) | 0145052-34-2 |
| Iodonium, [4-(1-methylethyl)phenyl](4-methylphenyl)-, tetrakis(2,3,4,5,6-pentafluorophenyl)borate(1-) (1:1) | 0178233-72-2 |
| 4,4'-Bis(methylylamino)benzophenone | 0194655-98-6 |
| Iodonium, (4-methylphenyl)[4-(2-methylpropyl)phenyl]-, hexafluorophosphate(1-) | 0344562-80-7 |
| 9H-Thioxanthenium, 10-[1,1'biphenyl]-4-yl-2-(1-methylethyl)-9-oxo, hexafluorophosphate | 0591773-92-1 |
| Oxirane, 2-methyl-, polymer with oxirane, 2-benzoylbenzoate | 1003557-16-1 |
| {a-4-(Dimethylamino)benzoylpoly(oxyethylene)-poly[oxy(1-methylethylene)]-poly(oxyethylene)}4-(dimethylamino)benzoate | 1003557-17-2 |
| 1,3-Di({a-2-(phenylcarbonyl)benzoylpoly[oxy(1-methylethylene)]}oxy)-2,2-bis({a-2-(phenylcarbonyl)benzoylpoly[oxy(1-methylethylene)]}oxymethyl)propane | 1003567-82-5 |
| 1,3-Di({a-[1-chloro-9-oxo-9H-thioxanthen-4-yl)oxy]acetylpoly[oxy(1-methylethylene)]}oxy)-2,2-bis({a-[1-chloro-9-oxo-9H-thioxanthen-4-yl)oxy]acetylpoly[oxy(1-methylethylene)]}oxymethyl)propane | 1003567-83-6 |
| 1,3-Di({-4-(dimethylamino)benzoylpoly[oxy(1-methylethylene)]}oxy)-2,2-bis({-4-(dimethylamino)benzoylpoly[oxy(1-methylethylene)]}oxymethyl) propane | 1003567-84-7 |
| Poly(oxy-1,2-ethanediyl), a-[2-(4-chlorobenzoyl)benzoyl]-w-[[2-(4-chlorobenzoyl)benzoyl]oxy]- | 1007306-69-5 |
| 2-Propenoic acid, 1,1'-[9-[[(1-fluoro-9-oxo-9H-thioxanthen-4-yl)oxy]methyl]-7,12-dimethyl-3,6,8,11,13,16-hexaoxaoctadecane-1,18-diyl] ester | 1253390-33-8 |
| 2,3-Dihydroxy-6-(2-hydroxy-2-methyl-1-oxopropyl)-1,1,3-trimethyl-3-[4-(2-hydroxy-2-methyl-1-oxopropyl)phenyl]-1H-indene | |
| 2-Hydroxy-[4'-(2-hydroxypropoxy)phenyl]-2-methylpropanone | |
| Polyethylene glycol (200) di(β-4[p-acetylphenyl]piperazine) propionate | |
| Polyethylene glycol (200) di(β-4[4-(2-dimethylamino-2-benzyl)butanoylphenyl]piperazine) propionate | |

Photoactive compounds that may also be mentioned include dyes known as "photosensitizing dyes" such as ethyl eosin, eosin Y, fluorescein, rose bengal, methylene blue, erythrosine, phloxime, thionine, riboflavin and methylene green.

According to one particular embodiment of the invention, a combination of photoactive compounds is used.

3. The Light Source:

The process of the invention also uses iii) one or more identical or different light sources, said light sources photoirradiate by electromagnetic waves with wavelengths within the UV region up to the IR region.

The term "photoirradiation with an electromagnetic wave" is understood to mean any exposure of the composition or part of the composition to a light wave during the hair dyeing process. The light spectrum may comprise wavelengths within the UV region (200-400 nm), the visible region (400-745 nm) and the infrared region (745 nm to 3 μm).

Ultraviolet radiation, visible light or infrared radiation may be used. The choice depends on the characteristic absorption of the photoactive compound. If the photoactive compound absorbs in ultraviolet wavelengths, then ultraviolet radiation is used to activate it. If the photoactive compounds absorb in the visible wavelengths, then visible radiation is used. The absorption spectra of the photoactive compounds are available in the literature. For example, riboflavin has a maximum absorption at 430 nm, and therefore a violet or blue light source is used to activate riboflavin.

The amount of light energy varies as a function of the photoactive compounds. Light energy sufficient to activate said photoactive agent simply suffices. Occasionally, daylight suffices. According to a specific form of the invention, the dyeing process is carried out in natural sunlight or natural daylight.

According to another process for dyeing keratin fibres, the source of the photoirradiation is artificial. Mention may be made, for the lamps emitting in the UV region, of those described in Ullmann's Encyclopedia *Ultraviolet and Visible Spectroscopy* 2008, Wiley-VCH Verlag GmbH & Co. KGaA, Weinheim, 10.1002/14356007.b05 383.pub2, point 3.2. Mention may be made, for the lamps in general, of those mentioned in Ullmann's Encyclopedia *Lamps* 2005, Wiley-VCH Verlag GmbH & Co. KGaA, Weinheim 10.1002/14356007.a15 115, and Ullmann's Encyclopedia *Photochemistry* 2005, Wiley-VCH Verlag GmbH & Co. KGaA, Weinheim 10.1002/14356007.a19 573, point 3.2 "light sources".

The lamps used in the process of the invention are in particular incandescent, halogen, fluorescent, mercury or low-pressure lamps, low-pressure lamps, for example sodium or neon lamps, high-pressure lamps, for example mercury lamps, halide lamps, flash lamps, for example xenon flash lamps, fluorescent excimer lamps, such as xenon fluorescent excimer lamps, Light Emitting Diodes or LEDs of 0.01 to 1000 mW, lamps emitting black light or Wood's light, and lasers. Preferentially, the artificial sources originate from mercury lamps, tungsten halogen lamps, white neon tubes, LED lamps or UV lamps emitting at 254 nm or at 365 nm.

4. The Composition of the Dyeing Process

The dye(s) and/or pigment(s) especially of formula (I) as defined previously may be applied directly to keratin fibres in powder form or may be in a liquid composition.

The dye composition that is useful then contains, in a cosmetically acceptable medium, an amount of dyes and/or pigments as defined previously especially of formula (I) as defined previously, generally of between 0.001% and 30% relative to the total weight of the composition.

Preferably, the amount of dyes and/or pigments as defined previously, especially of formula (I), is between 0.01% and 5% by weight relative to the total weight of the composition. By way of example, the dye(s) are in an amount of between 0.01% and 2%.

Preferably, the composition of the dyeing and/or lightening process of the invention is in liquid form and contains one or more direct dyes, in particular cationic direct dyes, of formula (I) as defined previously.

The Medium:

The medium that is suitable for dyeing, also known as the dye support, is a cosmetic medium generally formed from water or a mixture of water and one or more organic solvents or a mixture of organic solvents.

The term "organic solvent" means an organic substance capable of dissolving another substance without chemically modifying it.

4.1. Organic Solvents:

Examples of organic solvents that may be mentioned include $C_1$-$C_4$ lower alkanols, such as ethanol and isopropanol; polyols and polyol ethers, for instance 2-butoxyethanol, propylene glycol, propylene glycol monomethyl ether, diethylene glycol monoethyl ether and monomethyl ether, and also aromatic alcohols, for instance benzyl alcohol or phenoxyethanol, and mixtures thereof.

The solvents are preferably present in proportions preferably of between 1% and 40% by weight approximately and even more preferably between 5% and 30% by weight approximately relative to the total weight of the dye composition.

4.2 the Adjuvants:

The composition comprising the dye(s) and/or pigment(s) especially of formula (I) as defined previously of the process of the invention may also contain various adjuvants conventionally used in hair dye compositions, such as anionic, cationic, nonionic, amphoteric or zwitterionic surfactants or mixtures thereof, anionic, cationic, nonionic, amphoteric or zwitterionic non-thiol and siliceous polymers or mixtures thereof, mineral or organic thickeners, and in particular anionic, cationic, nonionic and amphoteric polymeric associative thickeners, antioxidants, penetrants, sequestrants, fragrances, buffers, dispersants, conditioning agents, for instance volatile or non-volatile, modified or unmodified silicones, film-forming agents, ceramides, preserving agents and opacifiers.

The above adjuvants are generally present in an amount, for each of them, of between 0.01% and 20% by weight relative to the weight of the composition.

Needless to say, a person skilled in the art will take care to select this or these optional additional compound(s) such that the advantageous properties intrinsically associated with the dyeing composition in accordance with the invention are not, or are not substantially, adversely affected by the envisaged addition(s).

4.3 Dyes:

The composition comprising the dye(s) and/or pigment(s) especially of formula (I) as defined previously of the process of the invention preferably represent from 0.001% to 10% by weight approximately relative to the total weight of the dye composition, and even more preferentially from 0.05% to 5% by weight approximately.

In general, the addition salts of the oxidation bases and couplers that may be used in the context of the invention are especially chosen from the salts of addition with an acid, such as the hydrochlorides, hydrobromides, sulfates, citrates, succinates, tartrates, lactates, tosylates, benzenesulfonates, phosphates and acetates, and the salts of addition with a base, such as alkali metal hydroxides, for instance sodium hydroxide, potassium hydroxide, aqueous ammonia, amines or alkanolamines.

According to one particular embodiment, the composition of the process of the invention contains at least one oxidation base and optionally at least one coupler as defined above.

The process of the invention may also use another composition that comprises one or more chemical oxidizing agents. The term "chemical oxidizing agent" means chemical oxidizing agents other than atmospheric oxygen.

The chemical oxidizing agent may be chosen, for example, from hydrogen peroxide, urea peroxide, alkali metal bromates such as sodium bromate, persalts such as perborates and persulfates, and enzymes such as peroxidases and two-electron or four-electron oxidoreductases, for instance uricases, and four-electron oxidases such as laccases. The use of hydrogen peroxide is particularly preferred.

The content of oxidizing agent is generally between 1% and 40% by weight relative to the weight of the composition and preferably between 1% and 20% by weight relative to the weight of the composition.

4.4 The pH:

The pH of the composition comprising the dye(s) and/or pigment(s), especially of formula (I) as defined previously according to the invention, is generally between 2 and 12 approximately and preferably between 3 and 11 approximately. It may be adjusted to the desired value by means of acidifying or basifying agents usually used in the dyeing of keratin fibres, or alternatively using standard buffer systems.

The pH of the composition is preferentially between 6 and 9.

Among the acidifying agents, examples that may be mentioned include mineral or organic acids, for instance hydrochloric acid, orthophosphoric acid, sulfuric acid, carboxylic acids, for instance acetic acid, tartaric acid, citric acid or lactic acid, and sulfonic acids.

Among the basifying agents, examples that may be mentioned include aqueous ammonia, alkali metal carbonates, alkanolamines, such as mono-, di- and triethanolamines and derivatives thereof, sodium hydroxide, potassium hydroxide and the compounds of the following formula (α):

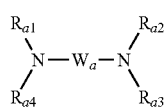

(α)

in which $W_a$ is a linear or branched, preferentially linear, divalent $(C_1-C_{10})$alkylene group, optionally interrupted with one or more heteroatoms such as O, S and $NR_{a1}$ and/or optionally substituted with one or more hydroxyl groups; $R_{a1}$, $R_{a2}$, $R_{a3}$ and $R_{a4}$, which may be identical or different, represent a hydrogen atom or a $C_1-C_4$ alkyl or $C_1-C_4$ hydroxyalkyl radical; preferentially, $W_a$ represents a propylene group.

According to one particular embodiment of the invention, the dye composition contains alkaline agents including at least monoethanolamine.

4.5 Forms of the Composition:

The dye composition comprising the dye(s) and/or pigment(s) especially of formula (I) as defined previously may be in various galenical forms, such as in the form of a liquid, a lotion, a cream or a gel, or in any other form that is suitable for dyeing keratin fibres. It may also be conditioned under pressure in an aerosol can in the presence of a propellant and form a mousse.

4.6 Mode of Application of the Dyes and/or Pigments, Photoactive Compounds and Light Source A subject of the invention is a direct dyeing process which comprises i) the application to keratin materials, in particular keratin fibres such as dark hair, of one or more dyes and/or pigments especially of formula (I) as defined previously and ii) one or more photoactive compounds, and iii) irradiation with one or more light sources of the keratin fibres treated with i) and ii).

According to a particular embodiment of the invention, the process for dyeing and/or lightening keratin fibres uses i) a dye comprising one or more alkenyl or alkynyl groups such as those described in formula (I'a), and irradiation with one or more light sources free of photoactive compounds ii). According to another variant, the process using one or more dyes comprising one or more alkenyl or alkynyl groups such as those described in formula (I'a) also uses ii) one or more photoactive compounds and iii) irradiation of the fibres with one or more light sources. The steps for the application of i) and iii) or i), ii) and iii) may be performed simultaneously or separately.

According to one particular embodiment of the invention, the step of applying or treating keratin fibres with iii) the light source(s) is performed extemporaneously with that of the application or treatment of the keratin fibres with i) one or more dyes and/or pigments especially of formula (I) as defined previously and ii) one or more photoactive compounds.

According to another particular embodiment of the process of the invention, the treatment of fibres with i) one or more dyes and/or pigments especially of formula (I) as defined previously and the step of treating the keratin fibres is performed in two stages. In a first stage, the keratin fibres are treated i) with one or more dyes and/or pigments especially of formula (I) as defined previously combined with ii) one or more photoactive compounds, and then, after a leave-on time, step ii) of irradiation of the keratin fibres with one or more light sources is performed with intermediate rinsing.

In particular, i) the dye(s) and/or pigment(s) especially of formula (I) as defined previously and ii) the photoactive compound(s) are in a dye composition as defined previously, in liquid form. The leave-on time after application of the composition containing the dyes of formula (I) is set at between 5 minutes and 2 hours and preferentially between 15 minutes and 1 hour, such as 30 minutes.

According to another particular embodiment, i) the dye(s) bearing a disulfide, thiol or protected-thiol function especially of formula (I) as defined previously are applied to the keratin fibres, followed by ii) the photoactive compound(s). The leave-on time after application of the dyes of formula (I) and the photoactive compounds is set at between 5 minutes and 2 hours and preferentially between 15 minutes and 1 hour, such as 30 minutes.

The dye(s) and/or pigment(s) i) especially of formula (I) as defined previously and ii) the photoactive compound(s) may be applied directly in powder form, without adjuvant, or in pulverulent form with solid adjuvants, and then, after an optional leave-on time set at between 5 minutes and 2 hours and preferentially between 15 minutes and 1 hour, such as 30 minutes, one or more irradiations using one or more light sources are applied to the keratin fibres. In one variant, the irradiation(s) from one or more light sources are applied extemporaneously to the treatment of the keratin fibres with i) one or more dyes and/or pigments especially of formula (I) as defined previously, and ii) one or more photoactive compounds, i) and ii) being applied in powder form, preferably to wet or moistened keratin fibres.

The application of one or more dyes and/or pigments especially of formula (I) as defined previously and the application of the photoactive compound(s) are generally performed at room temperature. It may, however, be performed at temperatures ranging from 20 to 80° C. and preferentially between 20 and 60° C., and the keratin fibres are then subjected to a treatment with irradiation with one or more light sources.

The fibres may be treated with a straightening iron assisted with water vapour. These irons are those that may be obtained commercially or those of professionals.

According to the invention, the term "water vapour" means "dry" water vapour, i.e. water vapour at atmospheric pressure, originating from water in gaseous form by boiling water in liquid form, using a heating device preferably at a temperature above the boiling point of water, at a temperature that produces water vapour (temperature between 80°

C. and 180° C. and preferably between 85° C. and 150° C.). The water vapour according to the invention is thus different from the saturating vapour of air at atmospheric pressure, also known as the hygrometry of the air, or air humidity.

The temperature of the water vapour is thus preferably greater than the boiling point of liquid water (10° C. at atmospheric pressure). It is thus constituted, at atmospheric pressure, solely of gaseous water; it is a dry vapour (see for example: http://fr.wikipedia.org/wikiVapeur_d'eau).

Preferably, the temperature of the water vapour at atmospheric pressure is greater than 80° C. and more particularly between 85° C. and 110° C. inclusive.

According to another embodiment of the invention, during step ii), a liquid water/water vapour mixture is applied to the keratin fibres. The latter mixture constitutes a mist. said mixture may also contain at least one other gas such as oxygen or nitrogen, mixtures of gases such as air, or other vaporizable compounds.

The temperature of the liquid water/water vapour mixture is preferably greater than or equal to 40° C. and is more particularly between 40° C. and 75° C. approximately.

Preferably, the liquid water/water vapour mixture is placed in contact with the fibre for a time ranging from 1 second to 1 hour and more preferentially from 5 minutes to 15 minutes. Needless to say, the application of said mixture may be repeated several times on the same fibre, each operation taking place for a time as indicated above.

The production of the liquid water/water vapour mixture used according to the invention may take place using any apparatus known per se intended for this purpose. However, according to the present invention, use is preferably made of apparatus comprising at least one water vapour generator directly connected to a hood that diffuses the liquid water/water vapour mixture onto the keratin fibres, in particular human hair. As types of apparatus, use will be made more particularly of the machine sold under the name Micromist® by the company Takara Belmont.

Another means is to arrange the keratin fibres treated beforehand with at least one dye bearing a disulfide, thiol or protected thiol function especially of formula (I) according to step i) as defined previously, over a source of water vapour such as a kettle, a boiling water container or a steam iron, for example the commercially available irons such as Joico K-Pak ReconstRx Vapor Iron and Babyliss Pro230 steam.

The treatment time of the keratin fibres with water vapour is between 5 minutes and 2 hours and preferentially between 15 minutes and 1 hour, such as 30 minutes.

According to another process for dyeing keratin fibres, the composition that comprises at least one dye and/or pigment especially of formula (I) as defined previously is an aqueous composition, this composition being applied to the hair followed by application of a straightening iron that generates water vapour in situ.

According to one variant of the process for dyeing keratin fibres, the composition that comprises at least one dye bearing a disulfide, thiol or protected thiol function especially of formula (I) as defined previously is applied to wet or moistened hair followed by application of a straightening iron that also generates water vapour in situ.

According to one embodiment of the process of the invention that uses one or more dyes bearing a protected thiol function especially of formula (I) as defined previously, the dyes are not deprotected beforehand. After a leave-on time on the keratin fibres as described previously, preferentially 30 minutes, the fibres are treated with water vapour preferentially for 30 minutes.

Preferentially, the process for dyeing keratin fibres does not use a reducing agent.

A treatment with a chemical oxidizing agent may optionally be combined as a post-treatment. Any type of oxidizing agent that is conventional in the field as described previously may be used. Thus, it may be chosen from hydrogen peroxide, urea peroxide, alkali metal bromates, persalts such as perborates and persulfates, and also enzymes, among which mention may be made of peroxidases, 2-electron oxidoreductases such as uricases, and 4-electron oxygenases such as laccases. The use of hydrogen peroxide is particularly preferred. The duration of the optional post-treatment with an oxidizing agent is between 1 second and 40 minutes and preferably between 1 and 10 minutes.

Preferentially, the chemical oxidizing agent(s), when they are present in the dyeing process of the invention, are in very mild concentrations, i.e. less than or equal to 5% by weight and preferentially 1% by weight relative to the total weight of the mixture comprising the dye(s) bearing a disulfide, thiol or protected thiol function especially of formula (I) as defined previously and the chemical oxidizing agent(s). According to one particular embodiment of the invention, the dyeing process does not involve any chemical oxidizing agent.

The application of the composition may be performed on dry hair or may be preceded by moistening of the hair.

According to one particular embodiment of the dyeing process, it is sought to lighten dark keratin fibres, especially with a tone depth of less than or equal to 6 and preferentially less than or equal to 4. To do this, the process for the dyeing and optical lightening of dark keratin fibres uses i) one or more dyes bearing a disulfide, thiol or protected thiol function especially of formula (I) as defined previously, which bear at least one fluorescent chromophore A and/or A' as defined previously; the step of treatment with water vapour ii) being performed either simultaneously or in a subsequent step after respecting a leave-on time between step i) and step ii) as mentioned previously.

Preferentially, the chemical oxidizing agent(s), when they are present in the lightening process according to the invention, are in very mild concentrations, i.e. less than or equal to 5% by weight and preferentially 1% by weight relative to the total weight of the mixture comprising the dye(s) bearing a disulfide, thiol or protected thiol function especially of formula (I) as defined previously and the chemical oxidizing agent(s). According to one particular embodiment of the invention, the dyeing process does not involve any chemical oxidizing agent.

According to a particular embodiment of the invention, the process for dyeing and/or lightening keratin fibres uses a pre-treatment of keratin fibers with reducing agent when the dye i) contain at least one photoreactive groupe chosen from alkenyl or alkynyl groups such as those described in formula (I'a) hereinbefore; and preferably the said process does not use photoinitiator.

According to another particular process of the invention, the process for dyeing and/or lightening keratin fibres do not uses a reducing agent when the dye i) does not contain a photoreactive group chosen from alkenyl or alkynyl groups.

In particular, the dyeing and/or lightening process of the invention that uses i) the dye(s) bearing a disulfide, thiol or protected thiol function especially of formula (I) as defined previously and ii) water vapour under conditions as presented previously is performed without using a reducing agent.

The examples that follow serve to illustrate the invention without, however, having any limiting nature on the scope of said invention.

EXAMPLES

I—Examples of Synthesis

Example 1

Synthetic Scheme

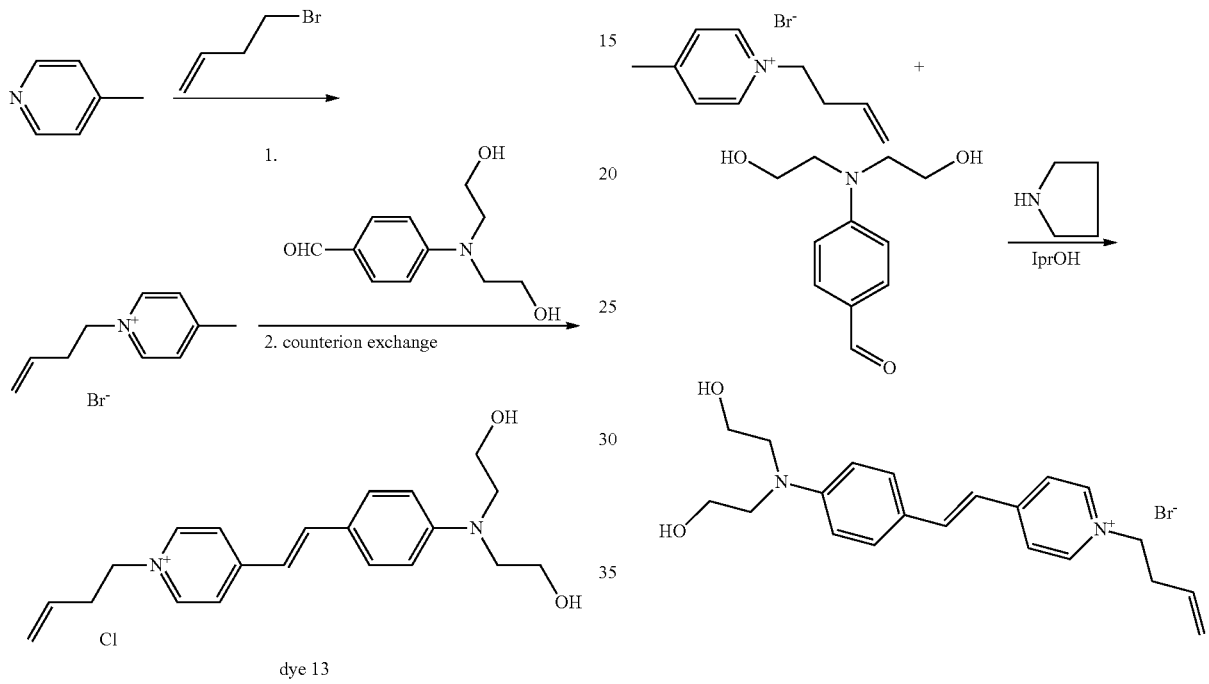

Step 1

4-Picoline (5 ml) is added to a three-necked flask equipped with a magnetic stirrer, a condenser and a bubbler. The alkene is added to the 4-picoline using a dropping funnel. At the end of the addition, the reaction mixture is heated at 80° C. for 2 hours. Ethyl acetate (200 ml) is added and the powder is then triturated to obtain a grey powder (11 g). The analyses are in accordance with the expected structure.

Step 2

The aldehyde is dissolved in 30 ml of isopropanol in a 250 ml three-necked flask equipped with a magnetic stirrer, a thermometer, a condenser and a bubbler. Pyrrolidine (2.02 g) diluted with isopropanol (10 ml) is added and the mixture is left stirring at room temperature (RT) for 15 minutes. Acetic acid (1.71 g) is added and an exotherm from 24° C. to 30° C. is observed with the appearance of white fumes in the reaction mixture. The mixture is allowed to cool to room temperature and the product from step 1 suspended in isopropanol (50 ml) is then added. The beaker containing the suspension is rinsed with isopropanol (10 ml) and added to the reaction mixture. The resulting mixture is stirred at room temperature for 24 hours. The product is evaporated to dryness and then purified by chromatography to obtain a shiny black powder.

Step 3: Counterion Exchange

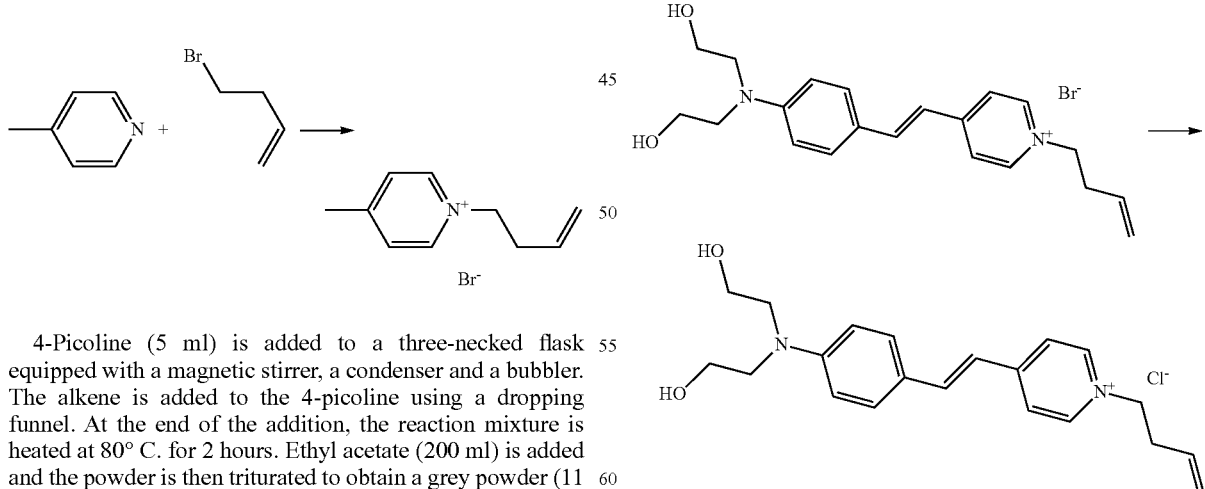

The product bearing a bromide counterion is dissolved in methanol (30 ml) and then placed on a column of silica ($C_{18}$). Water saturated with sodium chloride (500 ml) is passed through, followed by distilled water (500 ml). The product bearing a chloride counterion is desorbed with isopropanol, filtered off and then evaporated to dryness to obtain a shiny black powder (2.9 g). The analyses are in accordance with the expected structure.

II—Example of Dyeing

II-1) Process for Dyeing with Dyes Bearing an Alkenyl Group and Comparative Dyes Structure of the Dyes

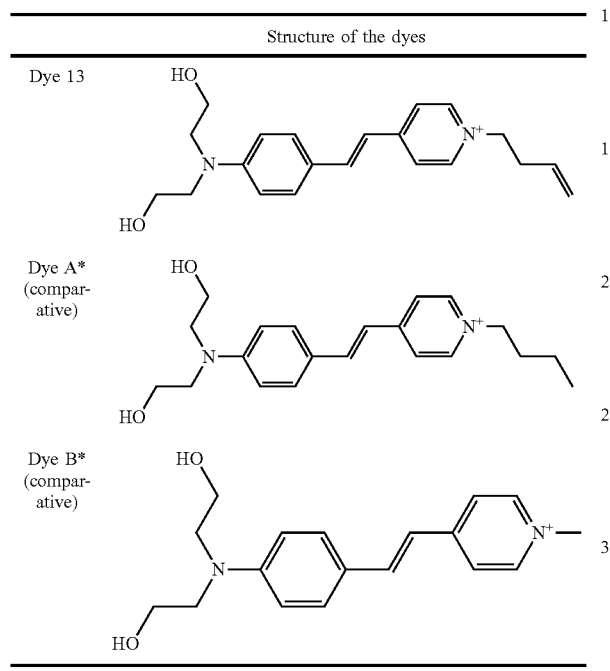

Structure of the dyes

Dye 13

Dye A* (comparative)

Dye B* (comparative)

(*)The synthesis of these comparative dyes is well known to those skilled in the art. Bibliographic references include: Dyes and Pigments (2008), 77(3), 678-685; Optical Materials (Amsterdam, Netherlands) (2008), 30(10), 1607-1615; CN 101424055; Journal of Applied Polymer Science (2009), 113(3), 1448-1453; CN 101424055.

washed with a standard shampoo (0.4 g of shampoo/g of lock). Repetitive shampooing is performed, with drying for 30 minutes under a hood between two shampoo washes.

Results:

After dyeing, the colour of the locks is measured with a Minolta CM2600d spectrocolorimeter (specular components included, 10° angle, illuminant D65) in the CIE L*a*b* system. In this system, L* represents the intensity of the colour, a* indicates the green/red colour axis and b* the blue/yellow colour axis.

ΔE represents the variation in colour between a lock of "pre-shampooed" hair and a lock of "post-shampooed" dyed hair, and is determined from the following formula:

$$\Delta E = \sqrt{(L^*-L_o^*)^2+(a^*-a_o^*)^2+(b^*-b_o^*)^2}$$

in which L*, a* and b* represent the values measured on the "pre-shampooed" lock and $L_o^*$, $a_o^*$ and $b_o^*$ represent the values measured on the "post-shampooed" lock.

The higher the value of ΔE, the less remanent the coloration with respect to successive shampooing.

The colorimetric results obtained are given in the table below.

|  | ΔE measured after 10 shampoo washes |
| --- | --- |
| Dye A (comparative) | 24.69 |
| Dye B (comparative) | 25.06 |
| Dye 13 (invention) | 5.56 |

It is seen from the above table that the coloration of the keratin fibres obtained with dye 13 according to the invention, after 10 shampoo washes, is much more resistant than the colorations produced with the comparative dyes A and B.

II-2) Process for Dyeing with Disulfide Dyes and Comparative Dyes

Comparative tests of dyeing keratin fibres were performed with the following dye:

Structure of the dye (Dye 1)

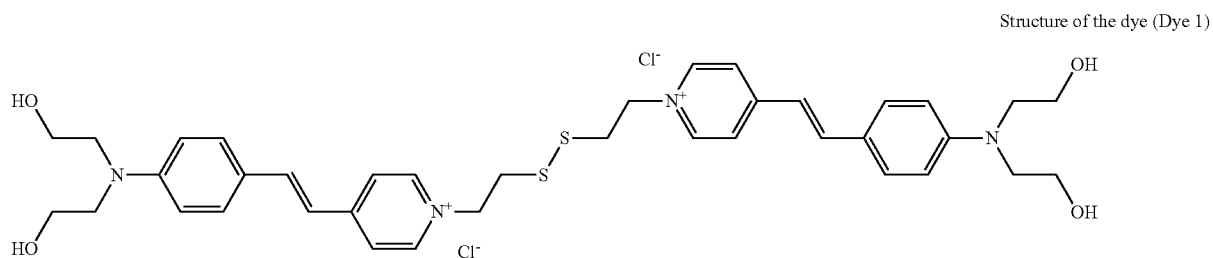 [SMILES: [Cl-] ; OCCN(CCO)c1ccc(/C=C/c2cc[n+](CCSSCC[n+]3ccc(/C=C/c4ccc(N(CCO)CCO)cc4)cc3)cc2)cc1 ; [Cl-]]

Step 1: Pretreatment of Keratin Fibres: Pre-Reduction of Hair

The hair is pre-reduced with a Dulcia Vidal DV2® reducing solution in a ratio of 2 g of DV2 (pure) per lock of 1 g (9:1 V/V) extemporaneously, followed by application to locks of natural grey hair containing 90% white hairs at a rate of 5 g of formula per 1 g of hair, at room temperature for 10 minutes. The locks are then wrung dry, and then dyed.

Step 2: Dyeing of Keratin Fibres

A solution of the dye at 2 g % in distilled water is applied to the pre-reduced hair at a rate of 5 g of formula per 1 g of hair, at room temperature for 30 minutes. During dyeing. The hair is exposed to UVB radiation (wavelength of 312 nm) with a total amount of UVB of 7 J/cm², and the lamp wavelength is 312 nm. The locks are then wrung dry and Two Protocols were Evaluated and Compared Protocol 1: Application of the dye after a reducing treatment (outside the invention as described in patent application EP 1 647 580): The process comprises a pretreatment with a reducing agent capable of reducing the disulfide bonds of the hair. The reducing agent is chosen, for example, from thiols, for example thioglycolic acid. This pretreatment lasts for 15 minutes. The dye composition is applied at room temperature for 30 minutes. The application of the dye composition is followed by an oxidative post-treatment step for several minutes to fix the dyes to the hair. The oxidizing agent may be any oxidizing agent conventionally used in the field, for example hydrogen peroxide. The content of oxidizing agent is generally between 1% and 40% by weight relative to the weight of the ready-to-use composition.

Protocol 2: Application of the dye with a photoactive compound (invention)

For each protocol, two locks are dyed. One lock is exposed to a light source (see below) during the dyeing and one lock is kept protected from light during the dyeing (by covering with aluminium foil).

The light source is a sun simulator: (model 69920, LOT-Oriel, Palaiseau, France). The power of the light is 10 mW/cm$^2$ (UV-A) and 4 mW/cm$^2$ (UV-B).

All the locks (natural hair containing 90% white hairs) are washed before use with an aqueous solution containing 2% by weight of sodium lauryl sulfate. The lock is taken in the hand containing 0.4 g/g of lock of sodium lauryl sulfate solution and the lock is passed between the fingers ten times to simulate shampooing. The lock is then rinsed thoroughly with tap water at 38° C. and then wrung dry to extract the maximum amount of water.

Protocol 1: Application of the Dye Following a Reductive Pretreatment (Comparative)

The locks of hair were reduced with a reducing treatment before applying the dye composition. This pretreatment consists in applying 5 g of L'Oréal Dulcia Vital 2-force1® (9% thioglycolic acid) per 1 g of hair, at room temperature for 15 minutes. The locks are rinsed with water and then drained dry before dyeing.

The dye composition was prepared with the contents of ingredients given in the table below (composition 1):

| Ingredients | Composition 1 |
|---|---|
| Hydroxyethylcellulose Natrosol 250MR | 0.72 g |
| C$_8$/C$_{10}$ Alkyl (50:50) hydroxyethylcellulose CG 110 | 5 g |
| Benzyl alcohol | 4 g |
| Polyethylene glycol 400 | 4 g |
| Dye 1 | 0.5 g |
| Water | qs 100 g |

Composition 1 is applied to natural hair containing 90% white hairs, at a rate of 5 g of composition per 1 g of hair, at room temperature for 30 minutes. The locks are rinsed with water, drained dry and then soaked for 5 minutes in a hydrogen peroxide solution (10 vol.: 5 g of composition per 1 g of hair). The locks are then rinsed, washed with shampoo and dried under a hood for 30 minutes.

Protocol 2: Application of Dye with a Photoactive Compound (Invention)

The dye composition 2 was prepared with the contents of ingredients given in the table below:

| Ingredients | Composition 2 |
|---|---|
| Hydroxyethylcellulose Natrosol 250MR | 0.72 g |
| C$_8$/C$_{10}$ Alkyl (50:50) hydroxyethylcellulose CG 110 | 5 g |
| Benzyl alcohol | 4 g |
| Polyethylene glycol 400 | 4 g |
| Dye 1 | 0.5 g |
| 4-(2-Hydroxyethoxy)phenyl-(2-hydroxy-2-propyl) ketone Photoactive compound | 0.5 g |
| Water | qs 100 g |

Composition 2 is applied to natural hair containing 90% white hairs, at a rate of 5 g of composition per 1 g of hair, at room temperature for 30 minutes.

The locks are then drained dry, and then washed with shampoo and dried under a hood for 30 minutes.

Repetitive Shampooing Protocol

All the locks (natural hair containing 90% white hairs) are washed before use with aqueous solution containing 2% by weight of sodium lauryl sulfate. The lock is taken in the hand containing 0.4 g/g of lock of sodium lauryl sulfate solution and the lock is passed between the fingers ten times to simulate shampooing. The lock is then rinsed thoroughly with tap water at 38° C. and then drained dry to extract the maximum amount of water. Repetitive shampooing is performed, with drying for 30 minutes under a hood between two shampoo washes.

Measurements of the Visibility of the Coloration and of the Remanence of the Visibility After dyeing, the colour of the locks is measured with a Minolta CM2600d spectrocolorimeter (specular components included, 10° angle, illuminant D65) in the CIE L*a*b* system. In this system, L* represents the intensity of the colour, a* indicates the green/red colour axis and b* the blue/yellow colour axis.

The higher the value of L*, the less intense the coloration.

ΔE shampoo represents the variation in colour between a lock of dyed hair before repetitive shampooing and a lock of dyed hair after repetitive shampooing, and is determined from the following formula:

$$\Delta E\text{shampoo} = \sqrt{(L_o^* - L_1^*)^2 + (a_o^* - a_1^*)^2 + (b_o^* - b_1^*)^2}$$

in which $L_0^*$, $a_0^*$ and $b_0^*$ represent the values measured on the "pre-repetitive shampooing" lock and $L_1^*$, $a_1^*$ and $b_1^*$ represent the values measured on the "post-repetitive shampooing" lock.

The higher the value of ΔEshampoo, the less remanent the coloration with respect to successive shampooing.

Results

The colorimetric results obtained are given in the table below.

| Dyeing protocol | L* before repetitive shampooing | $\Delta E_{shampoo}$ |
|---|---|---|
| protocol 1 without light | 31.98 | 8.38 |
| protocol 1 with light | 29.06 | 10.67 |
| protocol 2 without light | 29.83 | 7.32 |
| protocol 2 with light (invention) | 28.42 | 4.71 |

The results show that:
- the coloration obtained using protocol 1 and protocol 2 with or without exposure to light are of similar intensity (L*).
- the coloration obtained using protocol 2 with exposure to light and after 10 shampoo washes (repetitive shampooing) is much more resistant than the colorations performed using the comparative protocols.

During the coloration and shampooing using protocol 1, an unpleasant odour is noted. During the coloration and shampooing using protocol 2, no odour is noted.

The invention claimed is:
1. A method for dyeing keratin fibers comprising:
   (i) applying to the fibers at least one dye and/or one pigment;
   (ii) applying to the fibers at least one photoinitiator; and
   (iii) exposing said keratin fibers to at least one light source wherein said at least one light source includes light emitted by diodes, optionally emitting one or more electromagnetic waves with a wavelength ranging from 10 nm in the ultraviolet (UV) region to 100 μm in the infrared (IR) region;

wherein the at least one dye and/or pigment contains at least one photoreactive or photolabile group;

wherein the steps may be performed together or separately; and wherein when the at least one dye and/or pigment contains at least one alkenyl or alkynyl photoreactive group, the presence of the photoinitiator is optional.

2. The method of claim 1, wherein the at least one dye and/or pigment is chosen from the direct dyes of formula (I) below:

       (I)

the organic or mineral acid or base salts thereof, optical isomers thereof, geometrical isomers and tautomers thereof, and solvates thereof;

wherein:
$A_1$ represents a radical containing at least one anionic, cationic, zwitterionic or neutral colored chromophore;

$R_{a1}$ represents a group chosen from:
i) optionally substituted $(C_4$-$C_{20})$alkenyl or optionally substituted $(C_4$-$C_{20})$alkynyl;

$X_1$ is chosen from:
linear or branched, saturated or unsaturated divalent $C_1$-$C_{30}$ hydrocarbon-based chains, optionally interrupted and/or optionally terminated at one or both of its ends with one or more divalent groups or combinations thereof chosen from:
—N(R)—; —N$^+$(R)(R')—, Q$^-$; —O—; —S—; —S(O)—, —S(O)$_2$—, —C(O)—; —S(O)$_2$— with R and R', independently chosen from hydrogen atoms and $C_1$-$C_4$ alkyl, hydroxy($C_1$-$C_8$)alkyl or amino($C_1$-$C_8$)alkyl radicals, and Q$^-$ represents an organic or mineral anionic counterion;

aromatic or non-aromatic, saturated or unsaturated, fused or non-fused (hetero)cyclic radicals optionally comprising one or more identical or different, optionally substituted heteroatoms; and p is chosen from an integer equal to 0 or 1.

3. The method of claim 2, wherein the at least one dye and/or one pigment is chosen from the direct dyes of formula (I) wherein the chromophore $A_1$ is chosen from those derived from (poly)azo, hydrazono dyes, (poly)methine dyes, and naphthalimides.

4. The method of claim 2, wherein the at least one dye and/or one pigment is chosen from the direct dyes of formula (I) wherein the chromophore $A_1$ is fluorescent and chosen from those derived from (poly)methine dyes, comprising:
the (poly)methines of formulae (XVIIIa) and (XIXa):

       (XVIIIa)

       (XIXa)

wherein:
W$^+$ is chosen from a cationic heterocyclic or heteroaryl group;
W'$^+$ representing a divalent heterocyclic or heteroaryl radical as defined for W$^+$;
Ar is chosen from an aryl group, optionally substituted with i) one or more halogen atoms; ii) one or more groups ($C_1$-$C_8$)alkyl, iii) one or more hydroxyl groups; iv) one or more ($C_1$-$C_8$)alkoxy groups; v) one or more hydroxy($C_1$-$C_8$)alkyl groups, vi) one or more amino or (di)($C_1$-$C_8$)alkylamino groups, vii) one or more acylamino groups; viii) one or more heterocycloalkyl groups;

Ar' is a divalent aryl radical as defined for Ar;

m' represents an integer between 1 and 4 inclusive;

$R^c$ and $R^d$ are independently chosen from hydrogen atoms or optionally substituted group $(C_1$-$C_8$)alkyls, or alternatively $R^c$ contiguous with W or W' and/or $R^d$ contiguous with Ar or Ar' form, with the atoms that bear them, a (hetero)cycloalkyl;

Q$^-$ is an organic or mineral anionic counterion; and (*) represents the part of the chromophore linked to the rest of formula (I).

5. The method of claim 2, wherein the at least one dye and/or pigment is chosen from the direct dyes of formula (I) wherein p is equal to 1, at least one of the radical $X_1$ represents the following sequence:

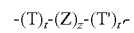

said sequence being linked in formula (I), as follows:

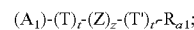

wherein:
T and T' are independently chosen from one or more radicals or combinations thereof chosen from: —S(O)$_2$—; —O—; —S—; —N(R)—; —N$^+$(R)(R$^o$)—, Q$^-$; —C(O)—; wherein R and R$^o$ are independently chosen from hydrogen atoms, $C_1$-$C_4$ alkyl, $C_1$-$C_4$ hydroxyalkyl or aryl($C_1$-$C_4$)alkyl radicals and Q$^-$ represents an organic or mineral anionic counterion;

and a cationic or non-cationic, monocyclic heterocycloalkyl or heteroaryl radical;

the indices t and t' are independently chosen from 0 or 1;

Z represents:
—(CR$_1$R$_2$)$_m$— with m being an integer between 1 and 8 inclusive and $R_1$ and $R_2$, independently chosen from hydrogen atoms or group $(C_1$-$C_4$)alkyl, $(C_1$-$C_4$)alkoxy, hydroxyl, cyano, carboxyl or (di)($C_1$-$C_4$)(alkyl)aminos, said alkyl radicals optionally forming, with the nitrogen atom that bears them, a 5- to 7-membered heterocycle, optionally comprising another nitrogen or non-nitrogen heteroatom;

—(CH$_2$CH$_2$O)$_q$— or —(OCH$_2$CH$_2$)$_q$— wherein q is an integer between 1 and 15 inclusive; or a divalent arylene, ($C_1$-$C_4$)alkylaryl or aryl($C_1$-$C_4$) alkyl radical being optionally substituted with at least one group SO$_3$M with M representing a hydrogen atom, an alkali metal or an ammonium group, the ammonium being substituted with one or more identical or different, linear or branched ($C_1$-$C_4$)alkyl radicals, optionally substituted with one or more hydroxyl groups; and z is 0 or 1.

6. The method of claim 2, wherein the at least one dye and/or pigment are chosen from the direct dyes of formulae (1a) to (1n) below:

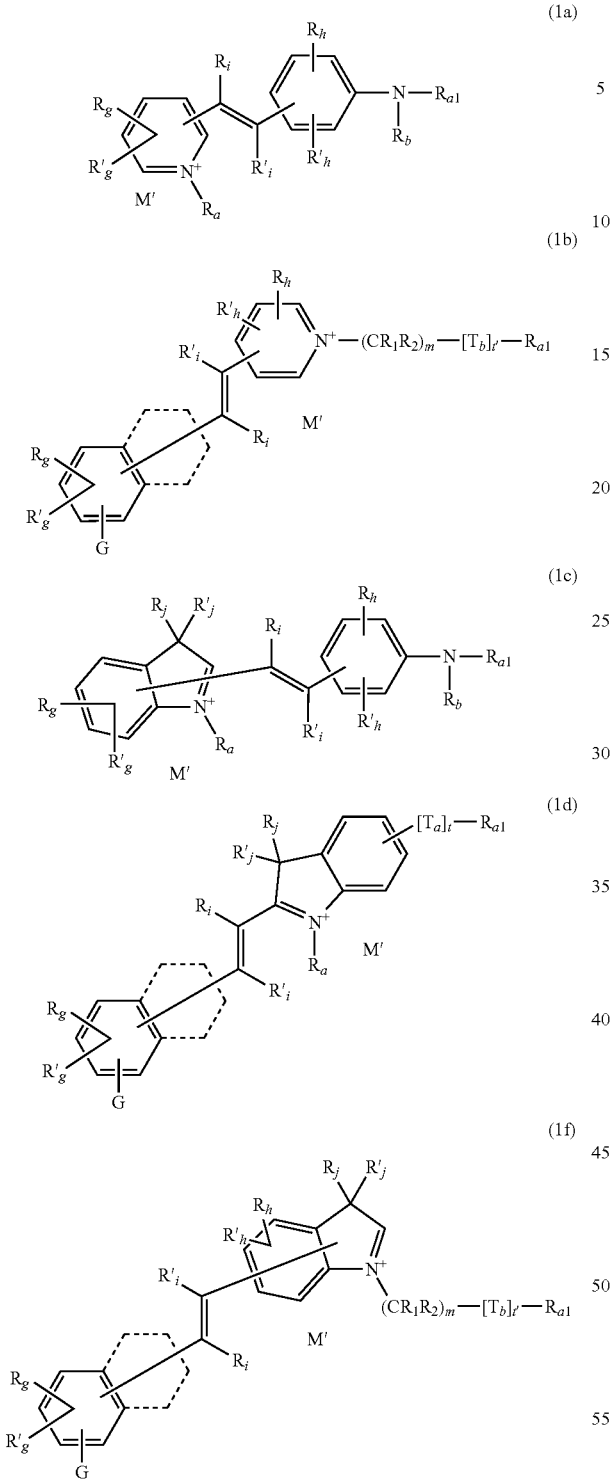

and the organic or mineral acid or base salts, optical isomers, geometrical isomers and tautomers thereof and solvates thereof;

wherein:

$R_{a1}$ represents a group chosen from:
  i) optionally substituted $(C_4-C_{20})$alkenyl or optionally substituted $(C_4-C_{20})$alkynyl;

$X_1$ is chosen from:
  linear or branched, saturated or unsaturated divalent $C_1-C_{30}$ hydrocarbon-based chains, optionally interrupted and/or optionally terminated at one or both of its ends with one or more divalent groups or combinations thereof chosen from: —N(R)—; —N$^+$(R)(R')—, Q$^-$; —O—; —S—; —S(O)—, —S(O)$_2$—, —C(O)—; —S(O)$_2$— with R and R', independently chosen from hydrogen atoms and $C_1-C_4$ alkyl, hydroxy($C_1$-$C_8$)alkyl or amino($C_1$-$C_8$)alkyl radicals, and Q$^-$ represents an organic or mineral anionic counterion;
  aromatic or non-aromatic, saturated or unsaturated, fused or non-fused (hetero)cyclic radicals optionally comprising one or more identical or different, optionally substituted heteroatoms;

p is chosen from an integer equal to 0 or 1;

G is chosen from a group —NR$_c$R$_d$ or $(C_1-C_6)$alkoxy;

$R_a$ and $R'_a$, are independently chosen from optionally substituted $(C_1-C_6)$alkyl groups;

$R_b$ is chosen from a hydrogen atom or an optionally substituted $C_1-C_6$ alkyl group;

$R_c$ and $R_d$ are independently chosen from hydrogen atoms, aryl($C_1-C_4$)alkyl or $(C_1-C_6)$alkoxy groups or $(C_1-C_6)$alkyl groups which are optionally substituted;

or two adjacent radicals $R_c$ and $R_d$, borne by the same nitrogen atom, together form a heterocyclic or heteroaryl group;

$R_g$, $R'_g$, $R_h$ and $R'_h$, are independently chosen from hydrogen atoms, halogen atoms, di($C_1-C_4$)(alkyl)amino, cyano, carboxyl, hydroxyl or trifluoromethyl groups, acylamino, $(C_1-C_4)$alkoxy, (poly)hydroxy($C_2-C_6$)alkoxy, $(C_1-C_4)$alkylcarbonyloxy, $(C_1-C_4)$alkoxycarbonyl, $(C_1-C_4)$alkylcarbonylamino, acylamino, carbamoyl or $(C_1-C_4)$alkylsulfonylamino radicals, aminosulfonyl radicals, or $(C_1-C_{16})$alkyl radicals optionally substituted with a group chosen from $(C_1-C_6)$alkoxy, hydroxyl, cyano, carboxyl and di($C_1-C_4$)(alkyl)amino, or the two alkyl radicals borne by the nitrogen atom of the amino group form a 5- to 7-membered heterocycle optionally comprising another nitrogen or non-nitrogen heteroatom;

or alternatively two groups $R_g$ and $R'_g$; $R_h$ and $R'_h$ borne by two adjacent carbon atoms together form a benzo or indeno ring, a fused heterocycloalkyl or fused heteroaryl group; the benzo, indeno, heterocycloalkyl or heteroaryl ring being optionally substituted with a halogen atom, a (di)($C_1-C_4$)(alkyl)amino, nitro, cyano, carboxyl, hydroxyl or trifluoromethyl group, an acylamino, $(C_1-C_4)$alkoxy, (poly)hydroxy($C_2-C_4$)alkoxy, $(C_1-C_4)$alkylcarbonyloxy, $(C_1-C_4)$alkoxycarbonyl or $(C_1-C_4)$alkylcarbonylamino radical, an acylamino, carbamoyl or $(C_1-C_4)$alkylsulfonylamino radical, an aminosulfonyl radical, or a $(C_1-C_{16})$alkyl radical optionally substituted with: a group chosen from $(C_1-C_6)$alkoxy, hydroxyl, cyano, carboxyl and (di)($C_1-C_4$)(alkyl)amino, or alternatively the two alkyl radicals borne by the nitrogen atom of the amino group form a 5- to 7-membered heterocycle optionally comprising another nitrogen or non-nitrogen heteroatom or alternatively when G represents —NR$_c$R$_d$ two groups $R_c$ and $R'_g$; $R_d$ and $R_g$; together form a saturated heteroaryl or heterocycle, optionally substituted with one or more groups $(C_1-C_6)$alkyl;

$R_i$, $R_j$, $R'_j$ and $R'_i$ are independently chosen from hydrogen atoms, or group $C_1-C_4$ alkyls;

or alternatively $R_i$ with $R_g$, $R'_i$ with $R_h$ borne by two adjacent atoms, together form a (hetero)cycloalkyl group, particularly for (1a) and (1 b), $R_i$ with $R_g$ or $R'_i$ with $R_h$ form a cycloalkyl;

$R_s$ represents a sulfonate radical $(O)_2S(O^-)$—, $M^+$ or a carboxylate radical —$C(O)O^-$, $M^+$ with $M^+$ representing an organic or mineral cationic counterion;

the amino groups of the compounds (1m) and (1n) are linked to the carbon atoms of the phenyl group in position 2, 3 or 4;

$R^e$, $R^f$, $R^g$ and $R^h$ are independently chosen from hydrogen atoms or $C_1-C_6$ alkyl groups which are optionally substituted;

$R_1$, $R_2$, $R_3$ and $R_4$ independently chosen from hydrogen atoms or a group $(C_1-C_4)$alkyl, $(C_1-C_{12})$ alkoxy, hydroxyl, cyano, carboxyl or $(di)(C_1-C_4)$(alkyl)aminos, said alkyl radicals optionally forming, with the nitrogen atom that bears them, a 5- to 7-membered heterocycle, optionally comprising another nitrogen or non-nitrogen heteroatom;

t and t' independently chosen from 0 or 1;

$T_a$ and $T_b$ independently chosen from one or more radicals or combinations thereof chosen from —$S(O)_2$—, —O—, —S—, —N(R)—, —$N^+(R)(R^o)$-$M^-$, —$C(O)$—, wherein R, $R^o$, independently chosen from hydrogen atoms or radicals $(C_1-C_4)$alkyl, hydroxy $(C_1-C_4)$alkyl; or an aryl$(C_1-C_4)$alkyl, and $M^-$ represents an organic or mineral anionic counterion;

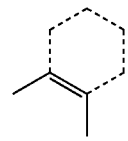

represents an aryl or heteroaryl group fused to the phenyl ring; or alternatively is absent from the phenyl ring;

m and n independently chosen from an integer between 0 and 10 inclusive with m+n representing an integer between 1 and 10; and M' represents an organic or mineral anionic counterion.

7. The process of claim 1, wherein the at least one dye and/or pigment is chosen from the following compounds:

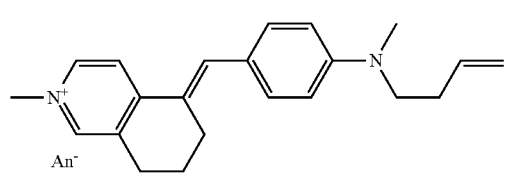

1

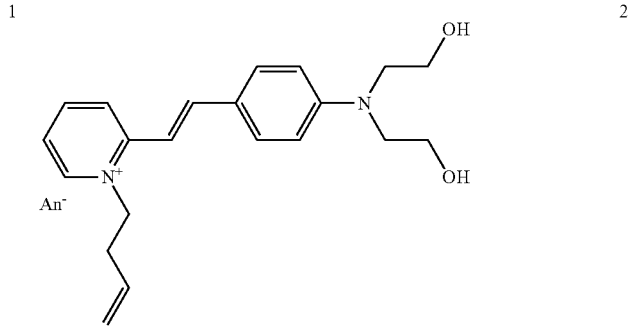

2

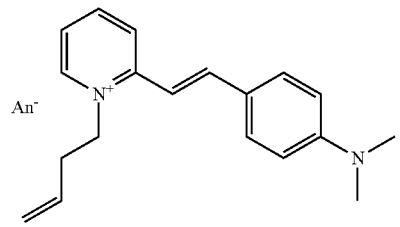

3

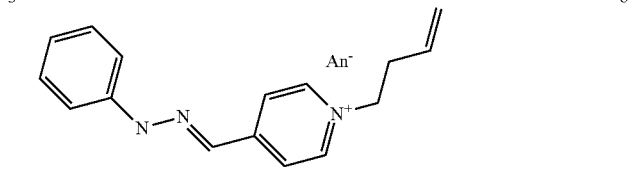

8

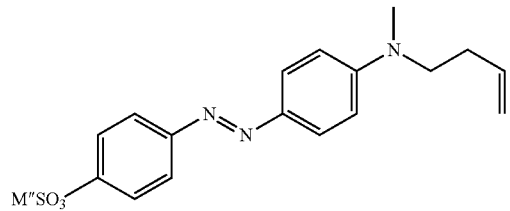

9

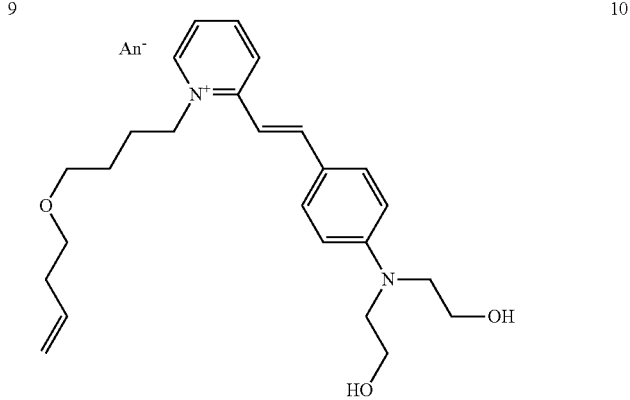

10

11
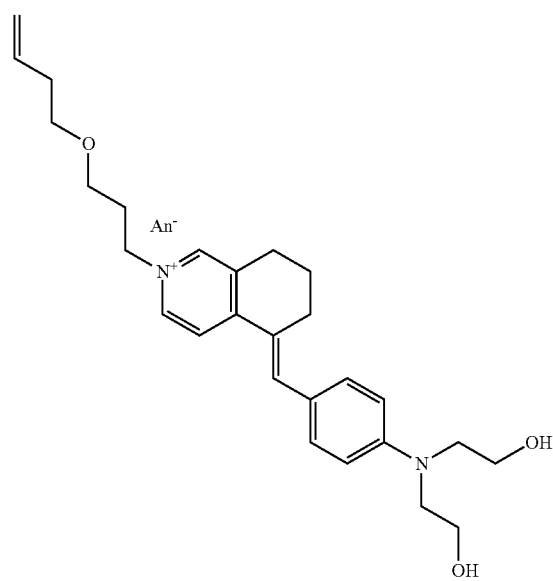
12
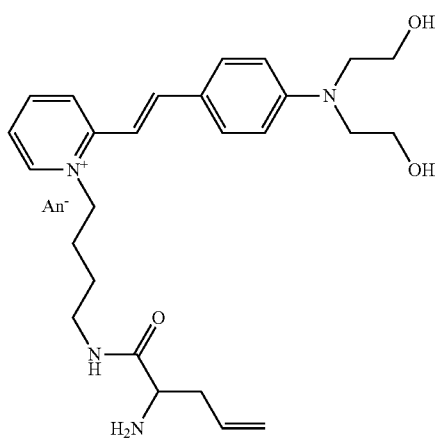
13
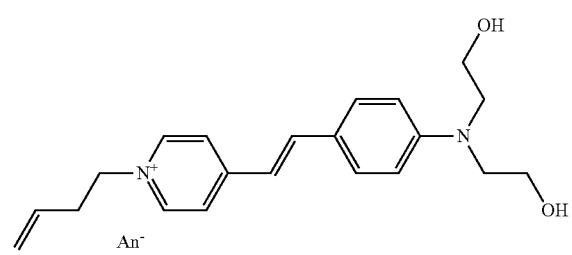
14
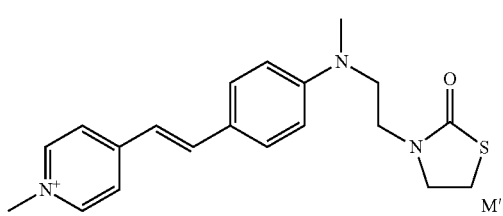
15
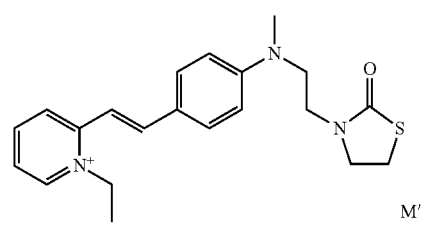
16
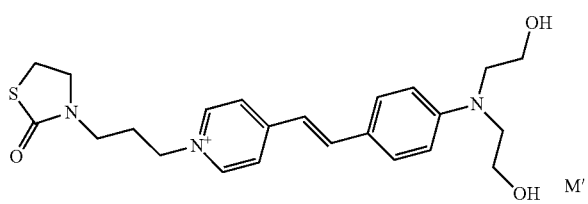
17
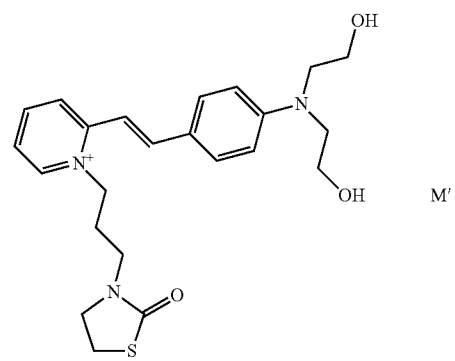
18
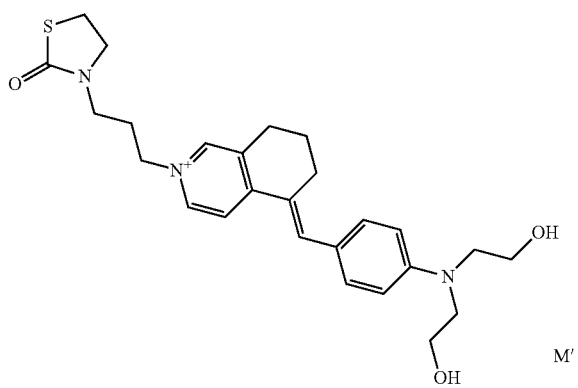

-continued
19
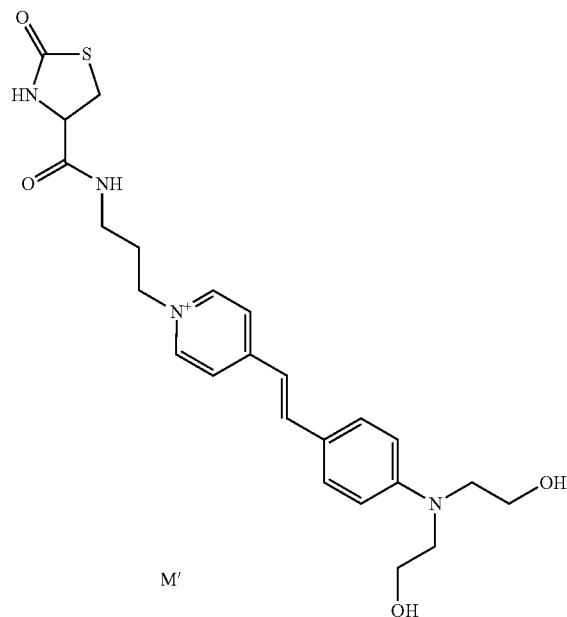
M'
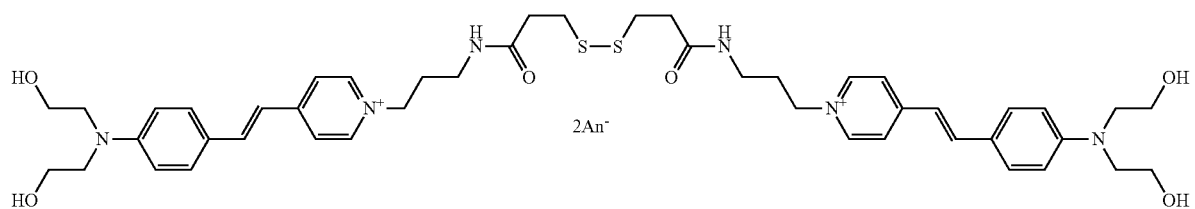
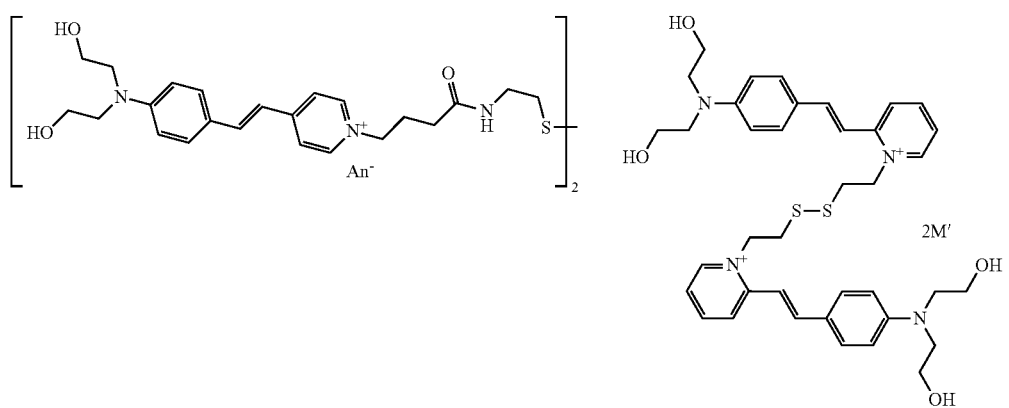

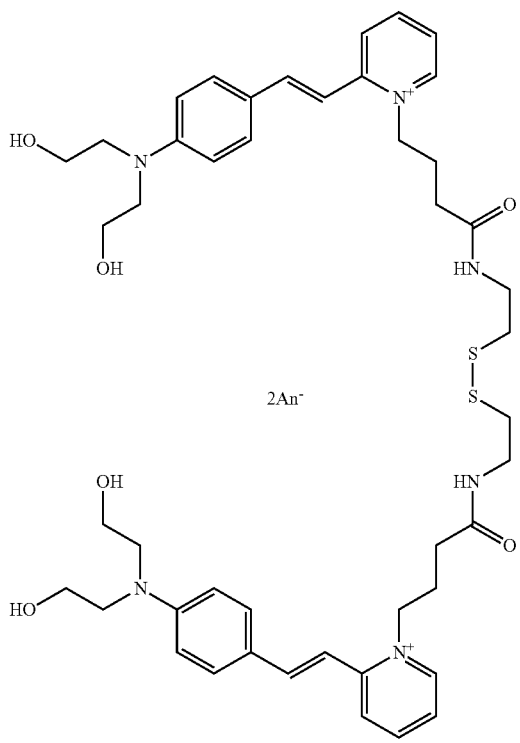

wherein An⁻ and M' are independently chosen from anionic counterions.

8. The method of claim 1, wherein the photoactive compounds are chosen from the compounds of formula (VI), and organic or mineral acid salts thereof, optical or geometrical isomers or tautomers thereof, and solvates thereof:

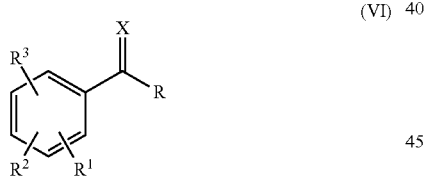

(VI)

wherein:
R represents a group chosen from:
i) $(C_1-C_{10})$alkyl, which is optionally substituted;
ii) $(C_1-C_{10})$alkoxy, which is optionally substituted;
iii) hydroxyl;
iv) optionally substituted (hetero)aryl;
v) (hetero)cycloalkyl, which is optionally substituted;
vi) $R^4-(X)_n-C(X)-(X)_{n'}$- with $R^4$ representing an optionally substituted $(C_1-C_{10})$alkyl, optionally substituted (hetero)aryl, or optionally substituted (hetero)cycloalkyl group, n and n' independently chosen from 0 or 1;
vii) $R_cR_dP(X)$— with $R_c$ representing an optionally substituted $(C_1-C_{10})$alkyl or optionally substituted (hetero)aryl group, and $R_d$ representing an optionally substituted (hetero)aryl group;
viii) or alternatively $R^1$ with R ortho to the group C(X)—R form, together with the atoms that bear them, a (hetero)cycle fused to the phenyl or (hetero)aryl fused to the phenyl, optionally substituted, with one or more oxo or thioxo groups;

$R^1$, $R^2$ or $R^3$ are independently chosen from hydrogen atoms, halogen atoms, optionally substituted $(C_1-C_{10})$ alkyl groups, $(C_1-C_{10})$alkoxy optionally substituted especially with a hydroxyl group, optionally substituted (hetero)aryl, optionally substituted (hetero)cycloalkyl, carboxyl, cyano, nitro, nitroso, —S(O)$_p$—OM with p equal to 1 or 2, M representing a hydrogen atom or an alkali metal or alkaline-earth metal, $R^4R^5N$—; $R^4$—$(X)_n$—C(X)—$(X)_{n'}$- with $R^4$, n and n' independently chosen from 0 or 1, $R^5$ is as defined for $R^4$ or alternatively $R^4$ and $R^5$ form, together with the nitrogen atom that bears them, an optionally substituted heterocycloalkyl or heteroaryl, which may be identical or different, being equal to 0 or 1; hydroxyl; or thiol;
or alternatively contiguous R and $R^1$ form, together with the carbon atoms that bear them, an optionally unsaturated and optionally substituted (hetero)cycloalkyl group;
or alternatively two contiguous substituents $R^1$, $R^2$ together form a group derived from maleic anhydride; and
X is independently chosen from oxygen or sulfur atoms or a group NR⁵ with R⁵ as defined previously.

9. The method of claim 1, wherein the at least one photoinitiator is chosen from the following compounds:
benzophenone, 2-methylbenzophenone, 3-methylbenzophenone, 4-methylbenzophenone, methyl 2-benzoylbenzoate, 4-ethyl 4-(dimethylamino)benzoate, 2-ethylhexyl p-(dimethylamino)benzoate, 1-[4-(2-hydroxyethoxy)phenyl]-2-hydroxy-2-methyl-1-propan-1-one, 2-(dimethylamino)-1-[4-(4-morpholinyl)phenyl]-2-(phenylmethyl)-1-butanone, 2-(dimethylamino)-2-[(4-methylphenyl)methyl]-1-[4-(4-morpholinyl)phenyl]-1-butanone, ethyl 2-[2-oxo-2- phenylacetoxyethoxy]oxyphenylacetate, 2-[2-hydroxyethoxy]ethyl oxyphenylacetate, hydroxy-1-(4-(4-(2-hydroxy-2-methylpropionyl)benzyl)phenyl-2-methyl-2-propanone, 4,4'-bis(diethylamino)benzophenone, (1-hydroxycyclohexyl)phenylmethanone, phenyl(2,4,6-trimethylphenyl)methanone, 4-phenylbenzophenone, 2-(dimethylamino)ethyl benzoate, 2,2-diethoxyacetophenone, 2-hydroxy-2-methyl-1-phenyl-1-propanone, 2,2-dimethoxy-2-phenylacetophenone, methyl 2-benzoylbenzoate, 2-benzyl-2-(dimethylamino)-4-morpholinobutyrophenone, 1-phenyl-2-[O-(ethoxycarbonyl)oxime] 1,2-propanedione, 4-(dimethylamino)-2-butoxyethyl benzoate, 1-[4-(1,1-dimethylethyl)phenyl]-2-hydroxy-2-methyl-1-propanone, 2-methyl-1-[(4-methylthio)phenyl]-2-(4-morpholinyl)-1-propanone; and organic or mineral acid salts thereof, optical or geometrical isomers or tautomers thereof, and solvates thereof.

10. The method of claim 1, wherein the at least one light source emitting one or more electromagnetic waves with wavelengths of between 10 nm in the UV region and 100 μm in the IR region comprise natural sunlight or daylight; lamps emitting in the UV region, incandescent lamps, halogen lamps, fluorescent lamps, mercury lamps, low-pressure lamps, high-pressure lamps, halide lamps, flash lamps, fluorescent excimer lamps, light-emitting diodes of 50 to 1000 mW, lamps emitting black light or Wood's light, and lasers.

11. The method of claim 1, which does not use at least one of a reducing agent and a chemical oxidizing agent.

12. The method of claim 1, further comprising a pretreatment of keratin fibers with reducing agent when the dye contains at least one photoreactive group chosen from alkenyl or alkynyl groups.

13. The method of claim 1, wherein a reducing agent is not employed when the dye does not contain a photoreactive group chosen from alkenyl or alkynyl groups.

* * * * *